(12) United States Patent
Hatakeyama et al.

(10) Patent No.: US 12,262,980 B2
(45) Date of Patent: Apr. 1, 2025

(54) BIO-ELECTRODE COMPOSITION, BIO-ELECTRODE, METHOD FOR MANUFACTURING BIO-ELECTRODE, AND SILICON MATERIAL PARTICLE

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 861 days.

(21) Appl. No.: 17/470,897

(22) Filed: Sep. 9, 2021

(65) Prior Publication Data
US 2022/0079461 A1    Mar. 17, 2022

(30) Foreign Application Priority Data

Sep. 15, 2020   (JP) ................. 2020-154751
Dec. 21, 2020   (JP) ................. 2020-211787

(51) Int. Cl.
*A61B 5/25*      (2021.01)
*A61B 5/024*     (2006.01)

(52) U.S. Cl.
CPC ............ *A61B 5/02444* (2013.01); *A61B 5/25* (2021.01); *A61B 2562/0209* (2013.01)

(58) Field of Classification Search
CPC .............. A61B 5/02444; A61B 5/25; A61B 2562/0209; A61B 5/263; A61B 5/28;
(Continued)

(56) References Cited

U.S. PATENT DOCUMENTS

| 5,981,680 A | 11/1999 | Petroff et al. |
| 2002/0177039 A1 | 11/2002 | Lu et al. |

(Continued)

FOREIGN PATENT DOCUMENTS

| EP | 2688133 A1 | 1/2014 |
| EP | 3 594 262 A1 | 1/2020 |

(Continued)

OTHER PUBLICATIONS

Feb. 16, 2022 Extended European Search Report issued in European Application No. 21195834.3.

(Continued)

*Primary Examiner* — Mark Kopec
*Assistant Examiner* — Jaison P Thomas
(74) *Attorney, Agent, or Firm* — Oliff PLC

(57) ABSTRACT

A bio-electrode composition contains particles having surfaces with an N-carbonyl sulfonamide salt shown by the following general formula (1). $R^1$ represents a linear, branched, or cyclic alkylene group having 1 to 20 carbon atoms and optionally having an aromatic group, ether group, or ester group, or an arylene group having 6 to 10 carbon atoms. Rf represents a linear, branched, or cyclic alkyl group having 1 to 4 carbon atoms, or an aryl group having 6 to 10 carbon atoms, and optionally has a fluorine atom. $M^+$ represents an ion selected from the group consisting of lithium, sodium, potassium, and silver ions. This invention provides a bio-electrode composition capable of forming a living body contact layer for a bio-electrode which is excellent in electric conductivity and biocompatibility, lightweight, and manufacturable at low cost, and prevents significant reduction in electric conductivity even when wetted with water or dried.

(Continued)

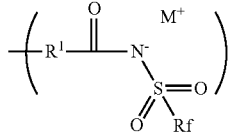

(1)

23 Claims, 4 Drawing Sheets

(58) Field of Classification Search
CPC .............. A61B 5/0533; A61B 5/265; A61B 2562/0215; A61B 2562/125; A61B 5/256; A61B 5/268; A61B 2562/164; C08K 2003/0806; C08K 3/041; C08K 3/08; C08K 5/435; C08K 3/36; C08K 9/04; C08K 3/04; C08K 3/34; C08K 5/548; C08K 9/06; Y02E 60/50; H01B 1/122; H01B 1/124; C08L 83/04; C08L 33/04; C08L 33/14; C08L 75/04; C08G 77/12; C08G 77/20

See application file for complete search history.

(56) References Cited

U.S. PATENT DOCUMENTS

| | | | |
|---|---|---|---|
| 2002/0188069 A1 | 12/2002 | Sugo et al. | |
| 2008/0118860 A1 | 5/2008 | Harada et al. | |
| 2009/0061358 A1 | 3/2009 | Ohashi et al. | |
| 2015/0188189 A1 | 7/2015 | Armand et al. | |
| 2015/0275060 A1 | 10/2015 | Kuroda et al. | |
| 2016/0155530 A1* | 6/2016 | Someya | A61B 5/6846 156/60 |
| 2017/0190586 A1* | 7/2017 | Yanagita | C09C 1/3081 |
| 2017/0275510 A1 | 9/2017 | Quan et al. | |
| 2019/0209740 A1 | 7/2019 | Hatakeyama et al. | |
| 2019/0387990 A1* | 12/2019 | Hatakeyama | A61B 5/257 |
| 2020/0015699 A1* | 1/2020 | Hatakeyama | A61B 5/25 |
| 2020/0060614 A1* | 2/2020 | Hatakeyama | C08G 77/28 |
| 2020/0113464 A1* | 4/2020 | Hatakeyama | A61B 5/25 |
| 2022/0110566 A1* | 4/2022 | Hatakeyama | C09D 151/085 |

FOREIGN PATENT DOCUMENTS

| | | |
|---|---|---|
| GB | 2 218 097 A | 11/1989 |
| JP | H05-095924 A | 4/1993 |
| JP | 2002-332305 A | 11/2002 |
| JP | 2003-225217 A | 8/2003 |
| JP | 2004-033468 A | 2/2004 |
| JP | 2004-527902 A | 9/2004 |
| JP | 2005-320418 A | 11/2005 |
| JP | 2008-111103 A | 5/2008 |
| JP | 2009-080474 A | 4/2009 |
| JP | 2011-079946 A | 4/2011 |
| JP | 2015-003839 A | 1/2015 |
| JP | 2015-019806 A | 2/2015 |
| JP | 2015-100673 A | 6/2015 |
| JP | 2015-193803 A | 11/2015 |
| JP | 2016-011338 A | 1/2016 |
| JP | 2016-065238 A | 4/2016 |
| JP | 2020-002342 A | 1/2020 |
| JP | 2020-006069 A | 1/2020 |
| JP | 2020-033224 A | 3/2020 |
| WO | 2013/039151 A1 | 3/2013 |
| WO | 2015/186596 A1 | 12/2015 |

OTHER PUBLICATIONS

Jun. 28, 2024 Extended European Search Report issued in European Patent Application No. 21195834.3.
Jul. 28, 2023, Office Action issued in Korean Patent Application No. 10-2021-0120846.
Long et al., "Polymer electrolytes for lithium polymer batteries," Journal of Materials Chemistry A, 2016, vol. 4, pp. 10038-10069.
Snyder et al., "Ion Conductivity of Comb Polysiloxane Polyelectrolytes Containing Oligoether and Perfluoroether Sidechains," Journal of The Electrochemical Society, 2003, vol. 150, No. 8, pp. A1090-A1094.
Jun. 28, 2024 Office Action issued in European Patent Application No. 21195834.3.

\* cited by examiner

[FIG. 1]
1
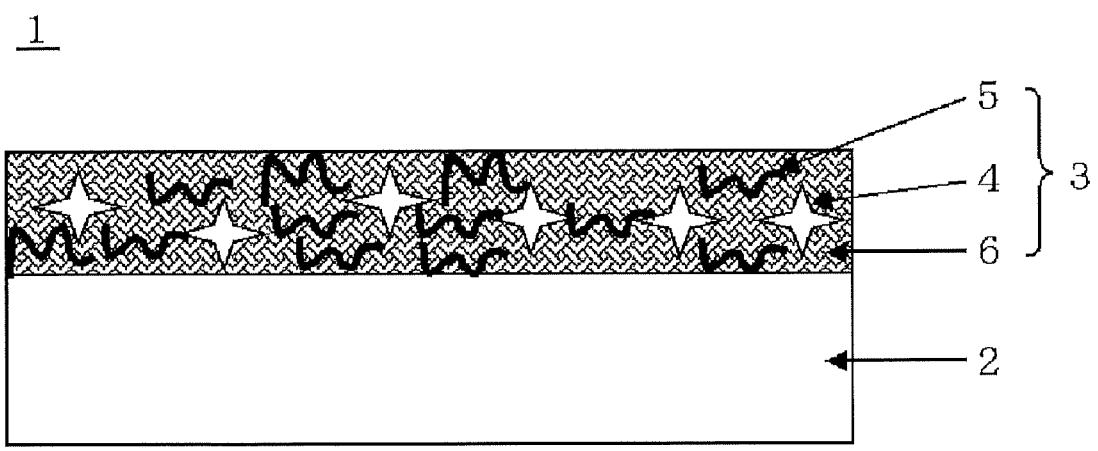
[FIG. 2]
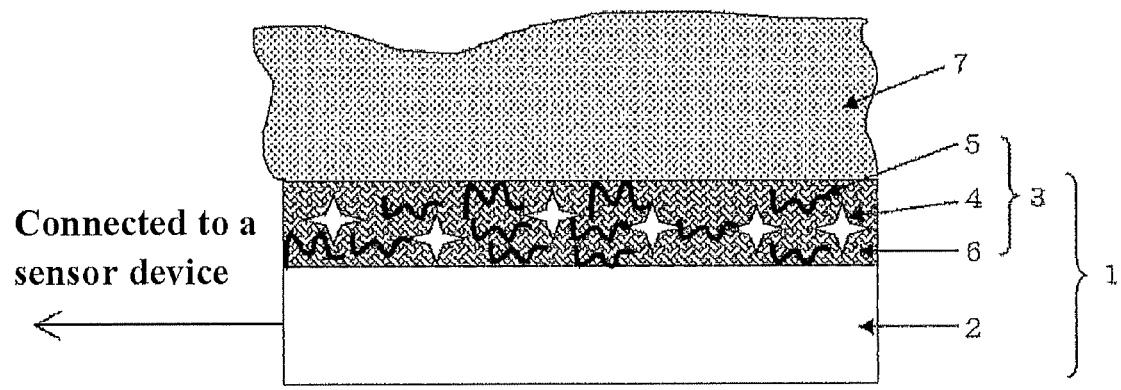
Connected to a sensor device

[FIG. 3]
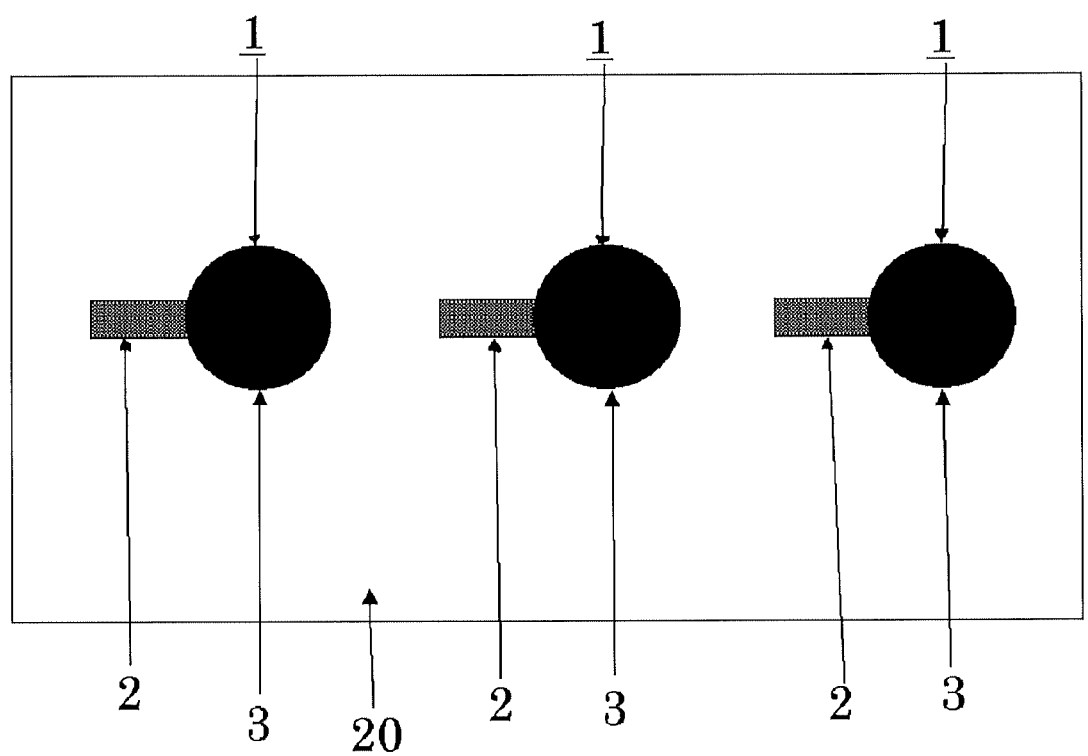

[FIG. 4]
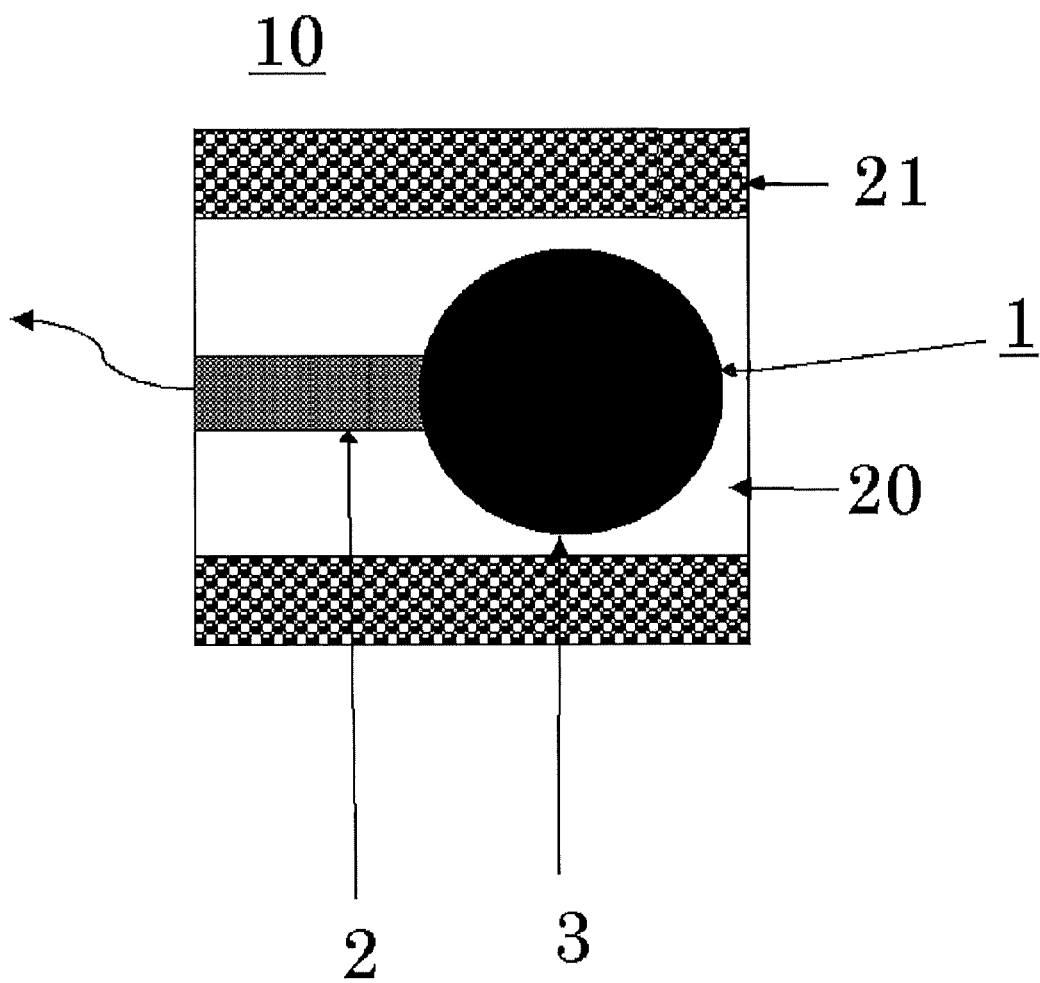

[FIG. 5]
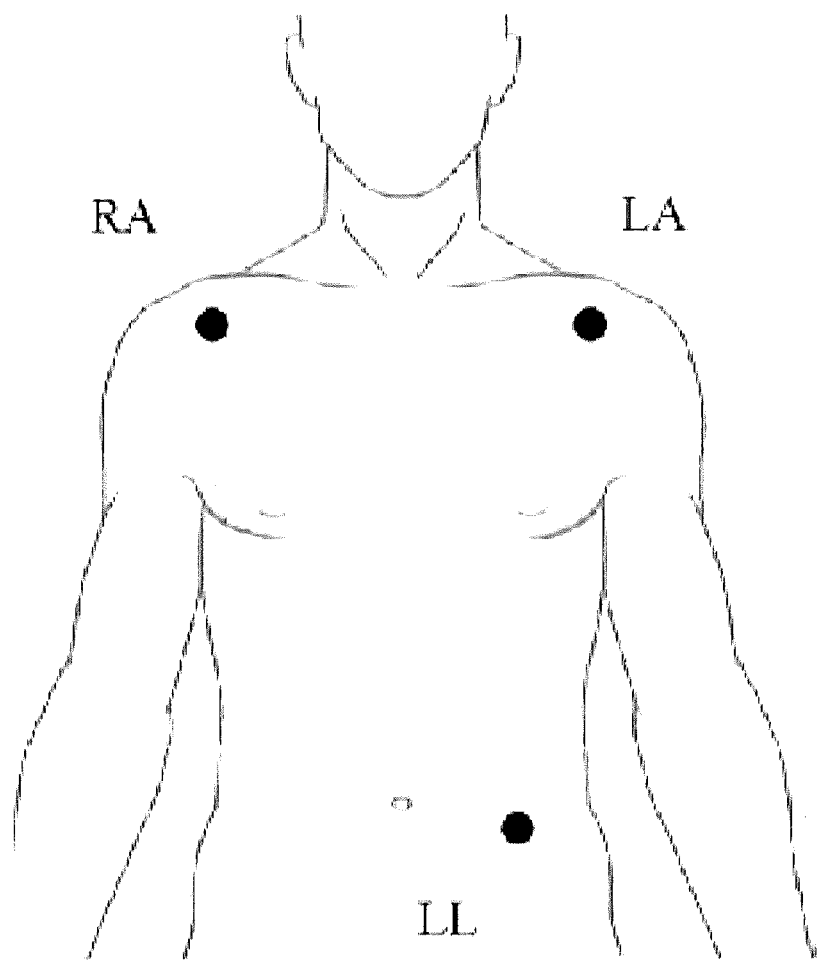
[FIG. 6]
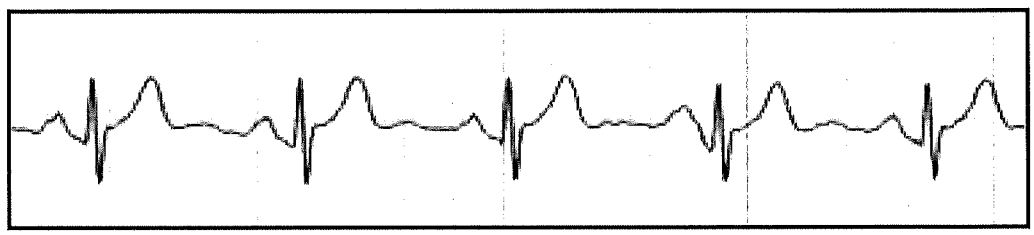

BIO-ELECTRODE COMPOSITION, BIO-ELECTRODE, METHOD FOR MANUFACTURING BIO-ELECTRODE, AND SILICON MATERIAL PARTICLE

TECHNICAL FIELD

The present invention relates to: a bio-electrode that is used in contact with the skin of a living body and capable of detecting physical conditions such as heart rate by an electric signal transmitted from the skin; a method for manufacturing the bio-electrode; and a bio-electrode composition and silicon material particles desirably used for a bio-electrode.

BACKGROUND ART

A recent growing popularity of Internet of Things (IoT) has accelerated the development of wearable devices, such as watches and eye-glasses that allow for Internet access. Even in the fields of medicine and sports, wearable devices for constantly monitoring the user's physical state are increasingly demanded, and such technological development is expected to be further encouraged.

In the field of medicine, use of wearable devices has been examined for monitoring the state of human organs by sensing extremely weak current, such as an electrocardiogram which detects an electric signal to measure the motion of the heart. The electrocardiogram measurement is conducted by attaching an electrode coated with an electro-conductive paste to a body, but this is a single (not continuous), short-time measurement. On the other hand, development of the above medical wearable device is aimed at device for continuously monitoring the health condition for a few weeks. Accordingly, a bio-electrode used in a medical wearable device is required to make no changes in electric conductivity even in long-time use and cause no skin allergy. In addition to these, it is also required that a bio-electrode is light-weight and can be produced at low cost.

Medical wearable devices are classified into two types: a type which is directly attached to body and a type which is incorporated into clothes. As the type which is attached to a body, it has been proposed a bio-electrode using water-soluble gel containing water and electrolyte, which are materials of the foregoing electro-conductive paste (Patent Document 1). The water-soluble gel contains sodium, potassium, or calcium as the electrolyte in a water-soluble polymer for retaining water, and converts changes of ion concentration from skin into electricity. On the other hand, as the type which is incorporated into clothes, it has been proposed a means to use cloth in which an electro-conductive polymer such as PEDOT-PSS (poly-3,4-ethylenedioxythiophene-polystyrenesulfonate) or silver paste is incorporated into the fibers for electrodes (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of the electro-conductive polymer, and further cause peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. The metal nanowire, however, can cause skin allergies since they are thin material with sharp tips. Even if these electrode materials themselves cause no allergic reaction in the manners described above, the biocompatibility may be degraded depending on the shape of a material and its inherent stimulation, thereby making it hard to satisfy both electric conductivity and biocompatibility.

Although metal films seem to function as excellent bio-electrodes thanks to extremely high electric conductivity, this is not always the case. Upon heartbeat, the human skin releases not only extremely weak current, but also sodium ion, potassium ion, and calcium ion. It is thus necessary to convert changes in ion concentration into current. Noble metals, however, are difficult to ionize and are inefficient in converting ions from skin to current. Therefore, the resulting bio-electrode using a noble metal is characterized by high impedance and high resistance to the skin during electrical conduction.

Meanwhile, the use of a battery containing an ionic liquid has been examined (Patent Document 6). Advantageously, the ionic liquid is thermally and chemically stable, and has excellent electric conductivity, providing wider battery applications. However, an ionic liquid having smaller molecular weight as shown in Patent Document 6 unfortunately dissolves into water. When a bio-electrode containing such an ionic liquid is used, the ionic liquid is extracted from the bio-electrode by sweating, which not only lowers the electric conductivity, but also causes rough dry skin as a result of the skin soaking with the liquid.

Batteries using a lithium salt of polymer type sulfonimide have also been examined (Non-Patent Document 1). Lithium has been applied to batteries because of their high ionic mobility. However, this is not a bio-compatible material. Additionally, lithium salts of fluorosulfonate have been examined in a form of a pendant on silicone (Non-Patent Document 2).

The bio-electrode fails to obtain biological information if it is apart from the skin. A change in contact area solely affects the quantity of electricity traveling through the electrode, and hence affects the baseline of an electrocardiogram (electric signal). Accordingly, in order to stably detect electric signals from the body, the bio-electrode is required to be in constant contact with the skin and make no changes in contact area. For this reason, the bio-electrode is preferably adherent. Moreover, the bio-electrode is required to have stretchability and flexibility so that the bio-electrode can follow changes in skin expansion or folding.

There has been examined a bio-electrode composed of: silver chloride at a portion which comes into contact with skin; and silver deposited at a portion through which electricity is conducted to a device. Solid silver chloride has neither adhesive strength to skin nor stretchability, so that the ability to collect biological signals is lowered particularly when the user moves. For this reason, a laminate film of silver chloride and silver is used as a bio-electrode with a water-soluble gel deposited between the bio-electrode and the skin. In this case, the aforementioned deterioration occurs when the gel is dried.

Recently, surface-modified functional silica has been developed. For example, a silicone rubber material containing silica having phosphonium salt in a pendant form on the surface has been proposed for antistatic application of a toner for printer (Patent Document 7). The silica surface is modified through reaction of the silica surface with a trialkoxysilane compound having phosphonium salt.

CITATION LIST

Patent Literature

Patent Document 1: WO 2013-039151 A1
Patent Document 2: JP 2015-100673 A
Patent Document 3: JP H05-095924 A
Patent Document 4: JP 2003-225217 A
Patent Document 5: JP 2015-019806 A
Patent Document 6: JP 2004-527902 A
Patent Document 7: JP 2020-033224 A Non Patent Literature Non Patent Document 1: J. Mater. Chem. A, 2016, 4, p 10038-10069
Non Patent Document 2: J. of the Electrochemical Society, 150(8), A1090-A1094 (2003)

SUMMARY OF INVENTION

Technical Problem

The present invention has been made to solve the above problems. An object of the present invention is to provide: a bio-electrode composition capable of forming a living body contact layer for a bio-electrode which is excellent in electric conductivity and biocompatibility, light-weight, and manufacturable at low cost, and which prevents significant reduction in the electric conductivity even when the bio-electrode is wetted with water or dried; a bio-electrode including a living body contact layer formed of the bio-electrode composition; and a method for manufacturing the bio-electrode.

Solution to Problem

To achieve the object, the present invention provides a bio-electrode composition comprising
(A) particles having surfaces with an N-carbonyl sulfonamide salt, wherein
the N-carbonyl sulfonamide salt is shown by the following general formula (1),

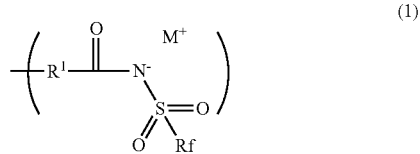

wherein $R^1$ represents a linear, branched, or cyclic alkylene group having 1 to 20 carbon atoms and optionally having an aromatic group, an ether group, or an ester group, or an arylene group having 6 to 10 carbon atoms; Rf represents a linear, branched, or cyclic alkyl group having 1 to 4 carbon atoms, or an aryl group having 6 to 10 carbon atoms, and optionally has a fluorine atom; and $M^+$ represents an ion selected from the group consisting of a lithium ion, a sodium ion, a potassium ion, and a silver ion.

Such a bio-electrode composition makes it possible to provide a bio-electrode composition capable of forming a living body contact layer for a bio-electrode which is excellent in electric conductivity and biocompatibility, light-weight, and manufacturable at low cost, and which prevents significant reduction in the electric conductivity even when wetted with water or dried.

The particles preferably have diameters of 2 nm to 50 μm.

Moreover, the particles are preferably any of silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolinium oxide particles, indium oxide particles, molybdenum oxide particles, and scandium oxide particles.

Such particles are suitably usable.

Further, the component (A) preferably comprises a reaction product between an alkoxysilane compound shown by the following general formula (2) and silicon material particles selected from the group consisting of silica particles, Si particles, SiO particles, SiC particles, and composites thereof,

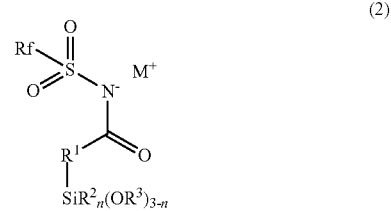

wherein $R^1$, Rf, and $M^+$ are as defined above; $R^2$ and $R^3$ are identical to or different from each other and each represent a hydrogen atom, or a linear, branched, or cyclic alkyl group having 1 to 10 carbon atoms; and "n" represents 0 or 1.

More preferably, the component (A) is a reaction product between 100 parts by mass of the silicon material particles and 5 parts by mass or more of the alkoxysilane compound shown by the general formula (2).

Such bio-electrode compositions have a pendant of an N-carbonyl sulfonamide salt on the surfaces of the silicon material particles, so that the permeability through the skin and the stimulus to the skin are reduced. This makes it possible to more surely prevent the composition from permeating the skin and causing allergies. Further, the N-carbonyl sulfonamide salt attached on the silicon material particle surfaces forms ion conduction path on the silicon material particle surfaces, and can increase the sensitivity of the bio-electrode.

The bio-electrode composition preferably further comprises a component (B) which is an adhesive resin.

The component (B) is preferably one or more selected from the group consisting of a silicone resin, a (meth) acrylate resin, and a urethane resin.

Such materials enable constant adhesion to skin and stable electric-signal collection for a long time.

Moreover, the component (B) preferably comprises diorganosiloxane having an alkenyl group, and organohydrogenpolysiloxane having an SiH group.

Further, the component (B) preferably further comprises a silicone resin having an $SiO_2$ unit and an $R_xSiO_{(4-x)/2}$ unit, wherein R represents a substituted or unsubstituted monovalent hydrocarbon group having 1 to 10 carbon atoms, and "X" represents a number in a range of 2.5 to 3.5.

Such materials can be suitably used in the bio-electrode composition.

The bio-electrode composition preferably further comprises a component (C) which is a polymer compound having an ionic repeating unit.

The ionic repeating unit preferably comprises a repeating unit-c having a structure selected from the group consisting of salts of ammonium, sodium, potassium, and silver formed with any of fluorosulfonic acid, fluorosulfonimide, and N-carbonyl-fluorosulfonamide.

The ionic repeating unit preferably has a structure shown by any of the following general formulae (3)-1 to (3)-4,

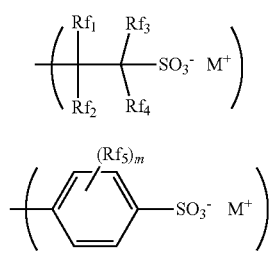
(3)-1

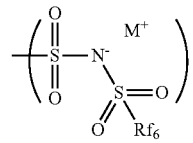
(3)-2

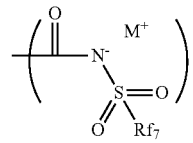
(3)-3

(3)-4 wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, and have at least one fluorine atom; $M^+$ represents an ion selected from the group consisting of an ammonium ion, a sodium ion, a potassium ion, and a silver ion; and "m" represents an integer of 1 to 4.

Moreover, the ionic repeating unit preferably comprises at least one repeating unit selected from the group consisting of repeating units-c1 to -c7 shown by the following general formula (3),

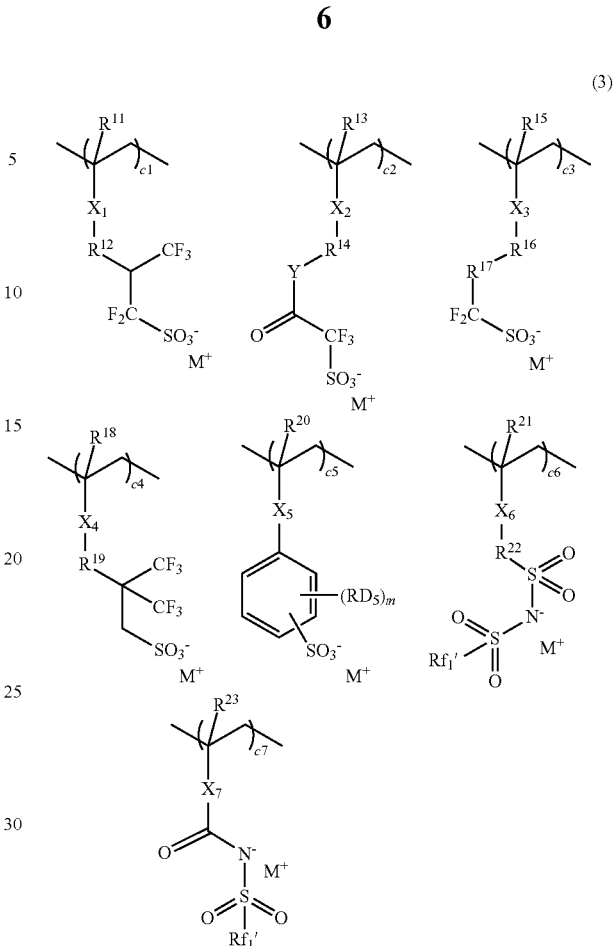
(3)

wherein $R^{11}$, $R^{13}$, $R^{15}$, $R^{18}$, $R^{20}$, $R^{21}$, and $R^{23}$ each independently represent a hydrogen atom or a methyl group; $R^{12}$, $R^{14}$, $R^{16}$, $R^{19}$, and $R^{22}$ each independently represent a single bond, or a linear, branched, or cyclic hydrocarbon group having 1 to 12 carbon atoms, the hydrocarbon group optionally having either or both of an ester group and an ether group; $R^{17}$ represents a linear or branched alkylene group having 1 to 4 carbon atoms, and one or two hydrogen atoms in $R^{17}$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a $—NR^{29}—$ group; $R^{29}$ represents a hydrogen atom, or a linear or branched alkyl group having 1 to 4 carbon atoms; $Rf_1'$ represents a fluorine atom or a trifluoromethyl group; $Rf_5$ represents a fluorine atom, or a linear or branched alkyl group having 1 to 4 carbon atoms and at least one fluorine atom; "m" represents an integer of 1 to 4; c1, c2, c3, c4, c5, c6, and c7 satisfy $0 \le c1 \le 1.0$, $0 \le c2 \le 1.0$, $0 \le c3 \le 1.0$, $0 \le c4 \le 1.0$, $0 \le c5 \le 1.0$, $0 \le c6 \le 1.0$, $0 \le c7 \le 1.0$, and $0 \le c1+c2+c3+c4+c5+c6+c7 \le 1.0$; and $M^+$ represents an ion selected from the group consisting of an ammonium ion, a sodium ion, a potassium ion, and a silver ion.

When the bio-electrode composition contains a polymer compound having such repeating units, the effects of the present invention can be further enhanced.

The bio-electrode composition preferably further comprises a component (D) which is a carbon powder and/or a metal powder.

The carbon powder is preferably one or both of carbon black and carbon nanotube.

The metal powder is preferably a powder of a metal selected from the group consisting of gold, silver, platinum, copper, tin, titanium, nickel, aluminum, tungsten, molybdenum, ruthenium, chromium, and indium.

More preferably, the metal powder is a silver powder.

Such materials further improve the electric conductivity.

The bio-electrode composition preferably further comprises a component (E) which is an organic solvent.

Such a material makes the coating property of the bio-electrode composition further favorable.

Furthermore, the present invention provides a bio-electrode comprising an electro-conductive base material and a living body contact layer formed on the electro-conductive base material, wherein the living body contact layer is a cured product of the above-described bio-electrode composition.

The inventive bio-electrode is excellent in electric conductivity and biocompatibility, light-weight, and manufacturable at low cost. Even when wetted with water or dried, the bio-electrode prevents significant reduction in the electric conductivity.

Moreover, the electro-conductive base material preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the inventive bio-electrode, such electro-conductive base materials are particularly suitably usable.

Furthermore, the present invention provides a method for manufacturing a bio-electrode having an electro-conductive base material and a living body contact layer formed on the electro-conductive base material, comprising:

applying the above-described bio-electrode composition onto the electro-conductive base material; and curing the bio-electrode composition to form the living body contact layer.

According to the inventive method for manufacturing a bio-electrode, it is possible to easily manufacture a bio-electrode which is excellent in electric conductivity and biocompatibility, light-weight, and manufacturable at low cost, and which prevents significant reduction in the electric conductivity even when the bio-electrode is wetted with water or dried.

Moreover, the electro-conductive base material used in the method for manufacturing a bio-electrode preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the inventive method for manufacturing a bio-electrode, such electro-conductive base materials are particularly suitably usable.

Additionally, the present invention provides a silicon material particle comprising an N-carbonyl sulfonamide salt shown by the following general formula (1) on a surface of the silicon material particle,

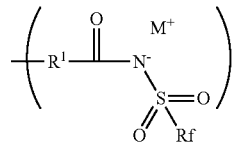

wherein $R^1$ represents a linear, branched, or cyclic alkylene group having 1 to 20 carbon atoms and optionally having an aromatic group, an ether group, or an ester group, or an arylene group having 6 to 10 carbon atoms; Rf represents a linear, branched, or cyclic alkyl group having 1 to 4 carbon atoms, or an aryl group having 6 to 10 carbon atoms, and optionally has a fluorine atom; and $M^+$ represents an ion selected from the group consisting of a lithium ion, a sodium ion, a potassium ion, and a silver ion.

Through modification of the silicon material particle with such an N-carbonyl-sulfonamide group, the resulting silicon material particles become a particularly useful component of a bio-electrode composition capable of forming a living body contact layer for a bio-electrode which enables high-sensitive and efficient conduction of ions released from skin and electric signals to a device (i.e., excellent in electric conductivity), which causes no allergy even when the bio-electrode is attached to skin for a long period (i.e., excellent in biocompatibility), and which prevents significant reduction in the electric conductivity even when the bio-electrode is wetted with water or dried.

The silicon material particle is preferably selected from the group consisting of silica particles, Si particles, SiO particles, SiC particles, and composites thereof.

Such particles are suitably utilizable.

Advantageous Effects of Invention

As described above, the inventive bio-electrode composition containing particles, such as silicon material particles, having an N-carbonyl-sulfonamide group on the surfaces makes it possible to form a living body contact layer for a bio-electrode that is capable of efficiently conducting electric signals from skin to a device (i.e., excellent in electric conductivity), free from the risk of causing allergies even when the bio-electrode is worn on skin for a long period (i.e., excellent in biocompatibility), light-weight, manufacturable at low cost, and free from significant reduction of the electric conductivity even when the bio-electrode is wetted with water or dried. The electric conductivity can be further enhanced by additionally adding an ionic polymer compound and/or an electro-conductive powder (carbon powder, metal powder). A bio-electrode having particularly high adhesive strength and high stretchability can be produced by combination with a resin that has adhesion and stretchability. Moreover, the stretchability and the adhesion to skin can be enhanced using additives, etc. The stretchability and the adhesion can also be adjusted by appropriately controlling the composition of the resin or the thickness of the living body contact layer.

With the above-described particles such as silicon material particles having an N-carbonyl sulfonamide salt on the surfaces, the inventive bio-electrode is allowed to achieve both of electric conductivity and biocompatibility, and is also allowed to have adhesion. Thus, it is possible to keep the contact area with skin constant and to stably obtain electric signals from skin with high sensitivity.

Additionally, the inventive method for manufacturing a bio-electrode enables simple and low-cost manufacturing of the inventive bio-electrode, which is excellent in electric conductivity and biocompatibility, light-weight, and free from significant reduction of the electric conductivity even when it is wetted with water or dried.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3 is a schematic view of printed bio-electrodes prepared in Examples of the present invention;

FIG. 4 is a schematic view of one of the bio-electrodes prepared in Examples of the present invention, the bio-electrode being cut out and provided with an adhesive layer thereon;

FIG. 5 is a view showing locations where electrodes and earth are attached on a human body in measuring biological signals in Examples of the present invention; and FIG. 6 shows one of electrocardiogram waveforms obtained using the bio-electrodes in Examples of the present invention.

DESCRIPTION OF EMBODIMENTS

As noted above, it has been desired to develop: a bio-electrode composition that can form a living body contact layer for a bio-electrode which is excellent in electric conductivity and biocompatibility, light-weight, and manufacturable at low cost, and which prevents significant reduction in the electric conductivity even when wetted with water or dried; a bio-electrode including a living body contact layer formed of the bio-electrode composition; and a method for manufacturing the bio-electrode.

The surface of skin releases extremely weak current and ions of sodium, potassium, and calcium in accordance with heartbeat. A bio-electrode has to convert the increase and decrease of these ions released from skin to electric signals. Accordingly, the bio-electrode requires a material that is excellent in ionic conductivity to transmit the increase and decrease of ions.

The present inventors have noticed ionic liquids as a material that is highly ionic conductive. Ionic liquids are characterized by high thermal and chemical stability as well as excellent electric conductivity, thereby having been widely used for battery applications. Known ionic liquids include hydrochloric acid salt, hydrobromic acid salt, hydroiodic acid salt, trifluoromethanesulfonic acid salt, nonafluorobutanesulfonic acid salt, bis(trifluoromethanesulfonyl)imide acid salt, hexafluorophosphate salt, and tetrafluoroborate salt of sulfonium, phosphonium, ammonium, morpholinium, pyridinium, pyrrolidinium, and imidazolium; etc. However, these salts (particularly, the ones with low molecular weight) are generally liable to hydrate, thereby resulting in such disadvantage that a salt is extracted with perspiration or by washing to lower the electric conductivity of a bio-electrode in which the living body contact layer is formed from any bio-electrode compositions containing these salts. In addition, the tetrafluoroborate salt is highly toxic, and the other salts are highly water-soluble to easily permeate into skin, thereby causing an issue of rough dry skin (i.e., highly irritative to skin).

In neutralized salts formed from highly acidic acids, the ions are strongly polarized to improve the ionic conductivity. This is why lithium salts of bis(trifluoromethanesulfonyl) imidic acid and tris(trifluoromethanesulfonyl)methide acid show high ionic conductivity as a lithium ion battery. On the other hand, the higher acidity of the acid makes the salt have stronger irritation to a body. That is, ionic conductivity and irritation to a body are in relation of trade-off. However, a salt applied to a bio-electrode has to achieve both higher ionic conductivity and lower irritation to a body.

A salt compound decreases its permeability through skin and irritation to the skin as the molecular weight is larger or the structure is of higher order in three dimensions. Accordingly, a salt compound bonded to particles such as silicon material particles is ideal because of the larger three-dimensional structure at the molecular level. Thus, the present inventors have conceived to synthesize particles, such as silicon material particles, having surfaces with a salt of ionic N-carbonyl-sulfonamide group.

Further, the present inventors have found that when this salt is mixed with, for example, a silicone-based, acrylic-based, or urethane-based adhesive (resin), the use of this mixture enables constant adhesion to skin and stable electric-signal collection for a long term.

Moreover, the inventors have found that higher ionic conductivity is required to form a bio-electrode with higher sensitivity, and incorporating an ionic polymer is effective for this purpose; the resulting bio-electrode functions as a highly sensitive bio-electrode with lower impedance. These findings have led to the completion of the present invention.

Specifically, the present invention is a bio-electrode composition comprising (A) particles having surfaces with an N-carbonyl sulfonamide salt, wherein the N-carbonyl sulfonamide salt is shown by the following general formula (1),

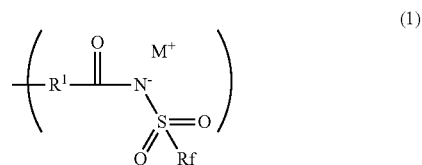

wherein $R^1$ represents a linear, branched, or cyclic alkylene group having 1 to 20 carbon atoms and optionally having an aromatic group, an ether group, or an ester group, or an arylene group having 6 to 10 carbon atoms; Rf represents a linear, branched, or cyclic alkyl group having 1 to 4 carbon atoms, or an aryl group having 6 to 10 carbon atoms, and optionally has a fluorine atom; and $M^+$ represents an ion selected from the group consisting of a lithium ion, a sodium ion, a potassium ion, and a silver ion.

Hereinafter, the present invention will be described in detail, but the present invention is not limited thereto.

<Bio-Electrode Composition>

It is essential that the inventive bio-electrode composition should contain particles having surfaces with an N-carbonyl sulfonamide salt shown by the general formula (1). This bio-electrode composition may contain an adhesive resin in addition to (A) the particles having an N-carbonyl sulfonamide salt on the surfaces. The bio-electrode composition can further contain an ionic polymer and/or an electro-conductive powder (carbon powder, metal powder), and can further contain an organic solvent etc.

The particles are preferably silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolium oxide particles, indium oxide particles, molybdenum oxide particles, or scandium oxide particles. Among these, silicon material particles are particularly preferably used.

Hereinbelow, each component will be described in more details. Note that, in the following description, the particles having an N-carbonyl sulfonamide salt on the surfaces is also referred to as "component (A)", an adhesive resin as "component (B)", an ion polymer as "component (C)", an electro-conductive powder as "component (D)", an organic solvent as "component (E)", and other additive(s) as "component (F)".

[Component (A)]

The inventive bio-electrode composition contains the component (A) (particles having an N-carbonyl sulfonamide salt on the surfaces) as (A) an ionic material (salt). The ionic material (salt) is blended as a conductive material in the bio-electrode composition, and is particles, preferably silicon material particles, having on the surfaces a salt of lithium, sodium, potassium, or silver formed with an N-carbonylsulfonamide shown by the following general formula (1). Hereinafter, description will be given of silicon material particles, but the particles are not limited to silicon material particles.

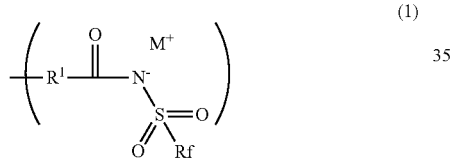

(1)

In the formula, $R^1$ represents a linear, branched, or cyclic alkylene group having 1 to 20 carbon atoms and optionally having an aromatic group, an ether group, or an ester group, or an arylene group having 6 to 10 carbon atoms. Rf represents a linear, branched, or cyclic alkyl group having 1 to 4 carbon atoms, or an aryl group having 6 to 10 carbon atoms, and optionally has a fluorine atom. $M^+$ represents an ion selected from the group consisting of a lithium ion, a sodium ion, a potassium ion, and a silver ion.

The silicon material particles having an N-carbonyl sulfonamide salt on the surfaces can be obtained as silicon material particles having a salt bonded on the surfaces through reaction between an alkoxysilane compound shown by the following general formula (2) and silicon material particles.

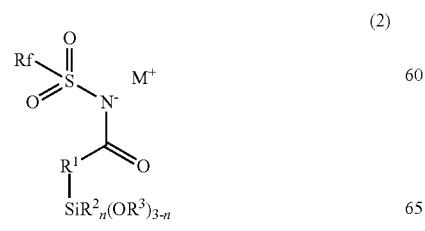

(2)

In the formula, $R^1$, Rf, and $M^+$ are as defined above. $R^2$ and $R^3$ are identical to or different from each other and each represent a hydrogen atom, or a linear, branched, or cyclic alkyl group having 1 to 10 carbon atoms. "n" represents 0 or 1.

Specific examples of the compound shown by the general formula (2) can include the following.

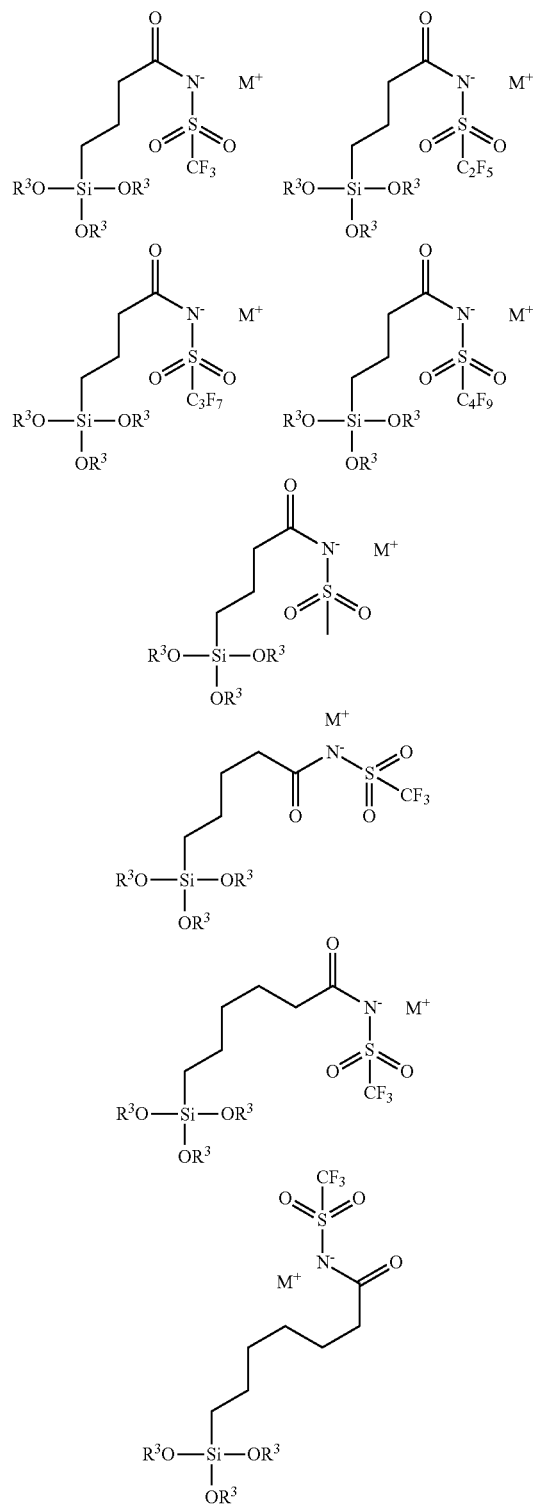

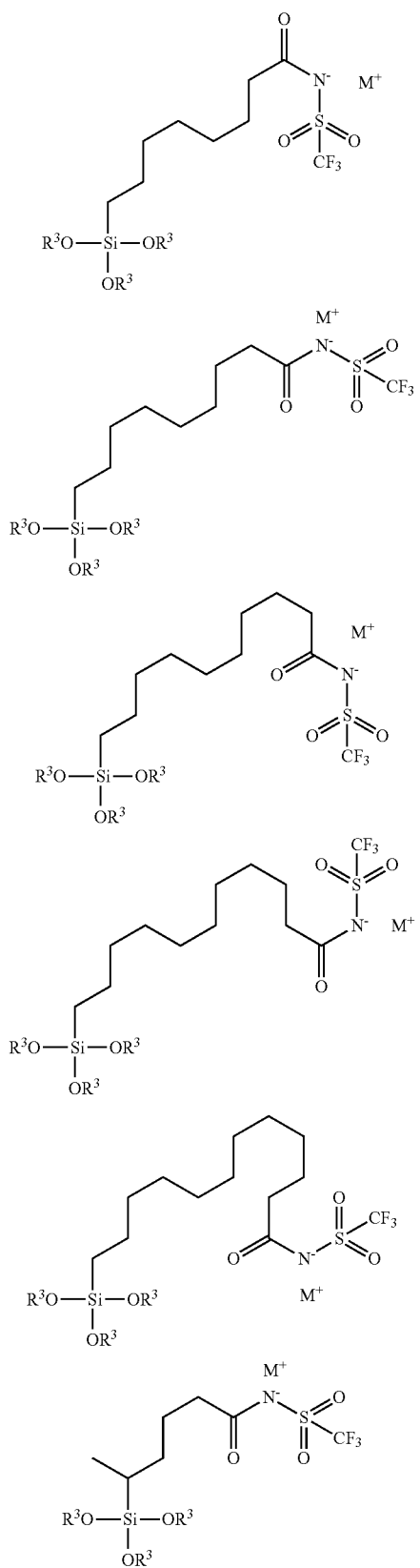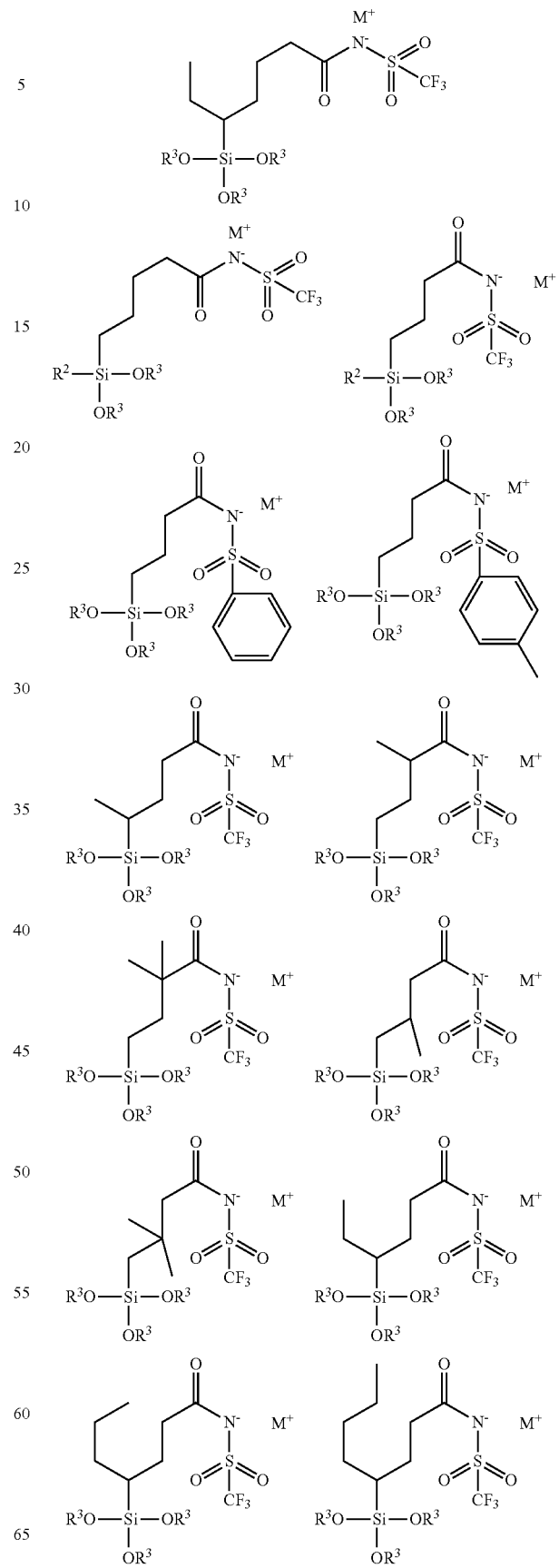

-continued
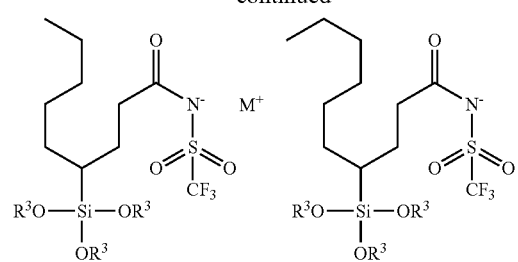
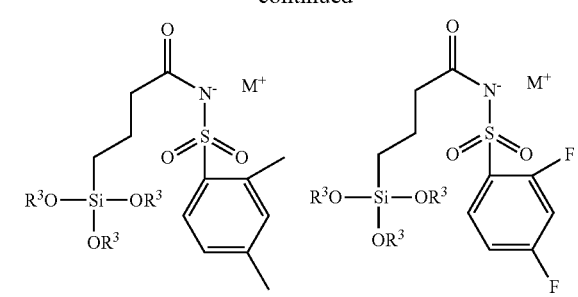
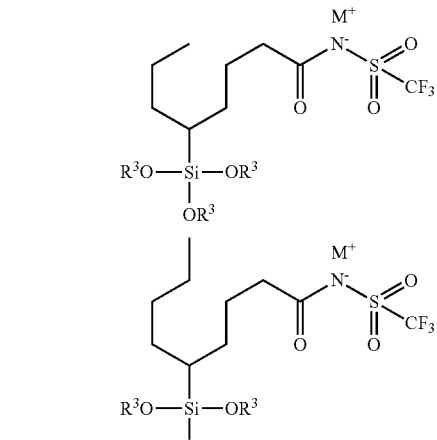
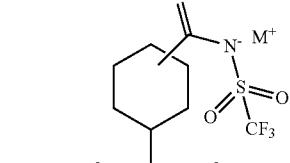
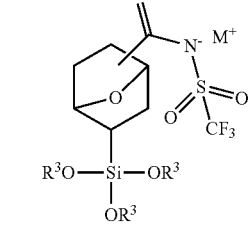
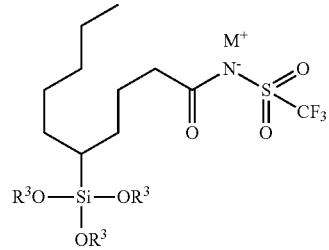
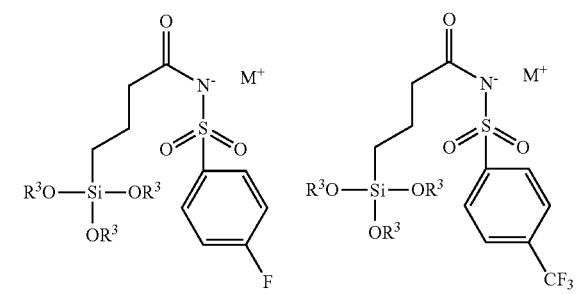
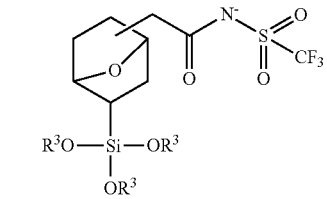
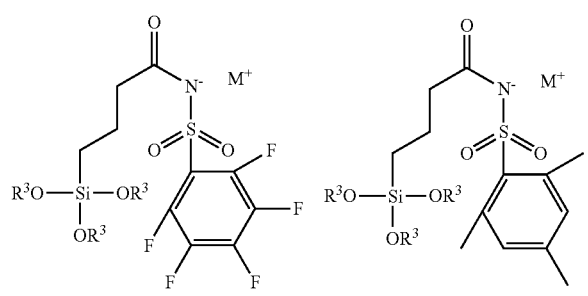
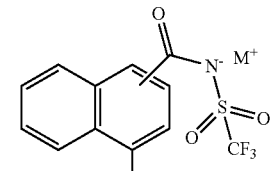
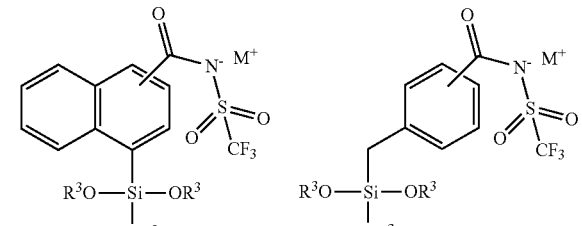

-continued

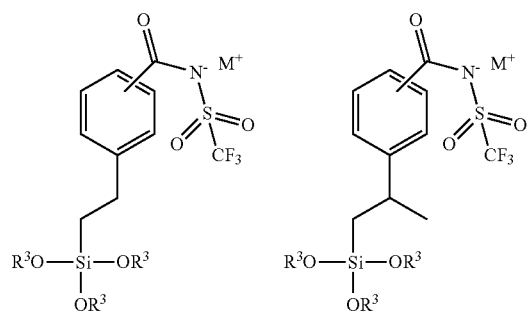

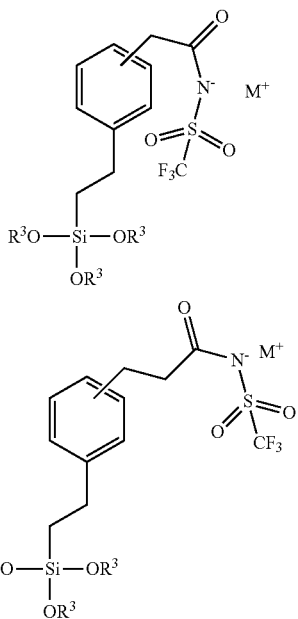

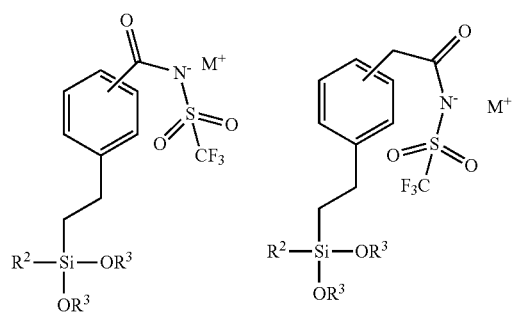

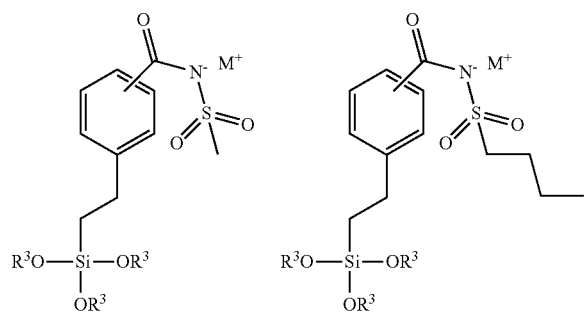

-continued

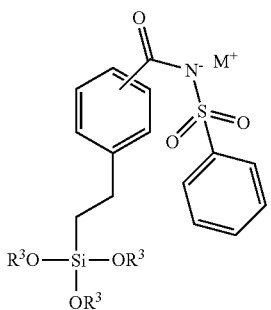

In these formulae, M+ is as defined above.

The surfaces of the silicon material particles are covered with a silanol group, so that the hydrophilicity is high. The modification with an N-carbonyl-sulfonamide group makes the resulting silicon material particles a particularly useful component of the bio-electrode composition capable of forming a living body contact layer for a bio-electrode which enables high-sensitive and efficient conduction of ions released from skin and electric signals to a device (i.e., excellent in electric conductivity), which causes no allergy even when the bio-electrode is attached to the skin for a long period (i.e., excellent in biocompatibility), and which prevents significant reduction in the electric conductivity even when the bio-electrode is wetted with water or dried.

The component (A) of the inventive bio-electrode composition is, for example, a reaction product between silicon material particles and an alkoxysilane compound of an N-carbonyl sulfonamide salt shown by the general formula (2). Moreover, such silicon material particles may be reacted with, in addition to the alkoxysilane compound shown by the general formula (2), another alkoxysilane compound, a silazane compound such as hexamethyldisilazane or hexaethyldisilazane, and a chlorosilane compound. Specific examples of the alkoxysilane compound other than that shown by the general formula (2) can include the following.

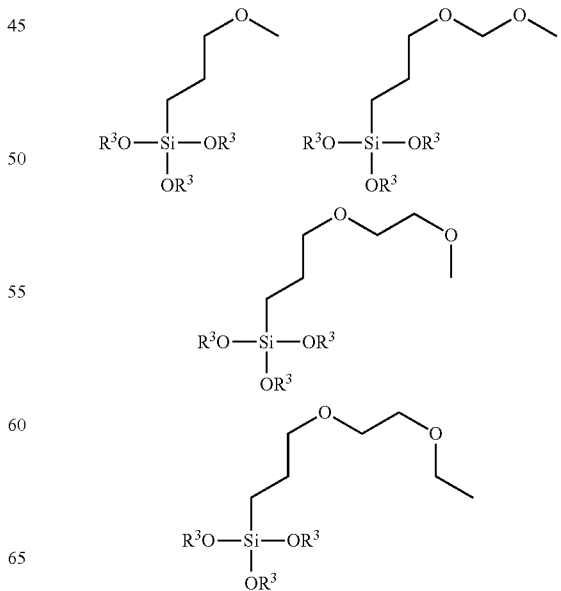

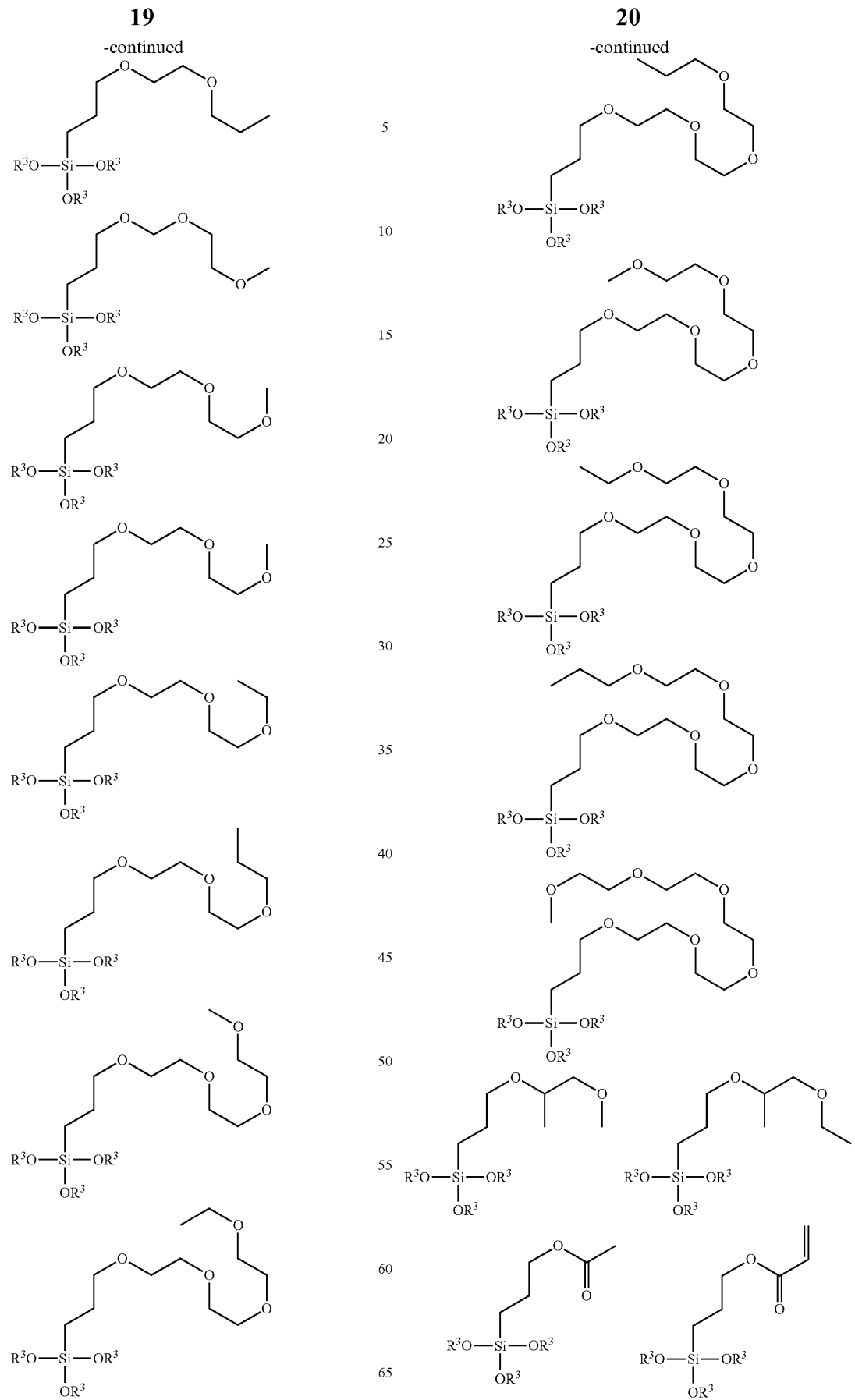

-continued
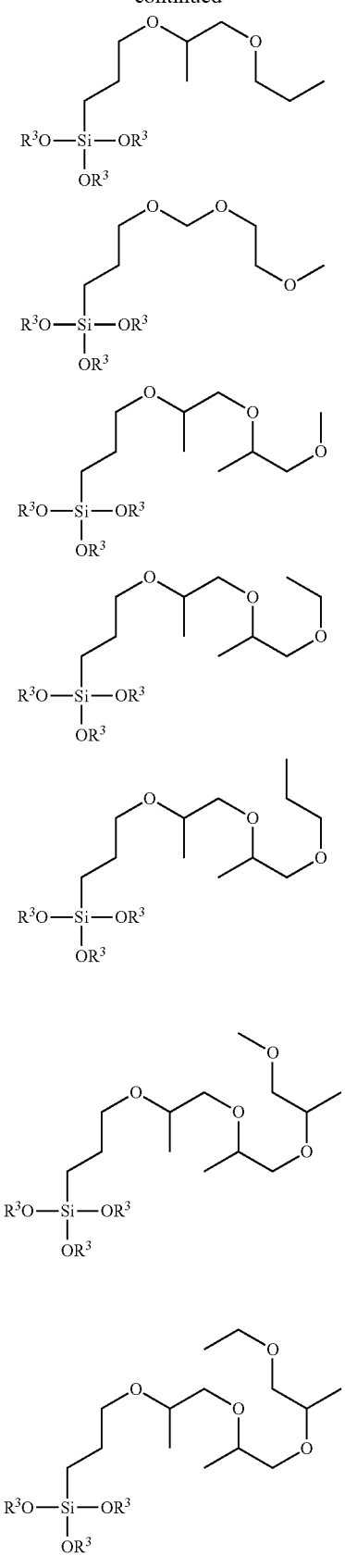
-continued
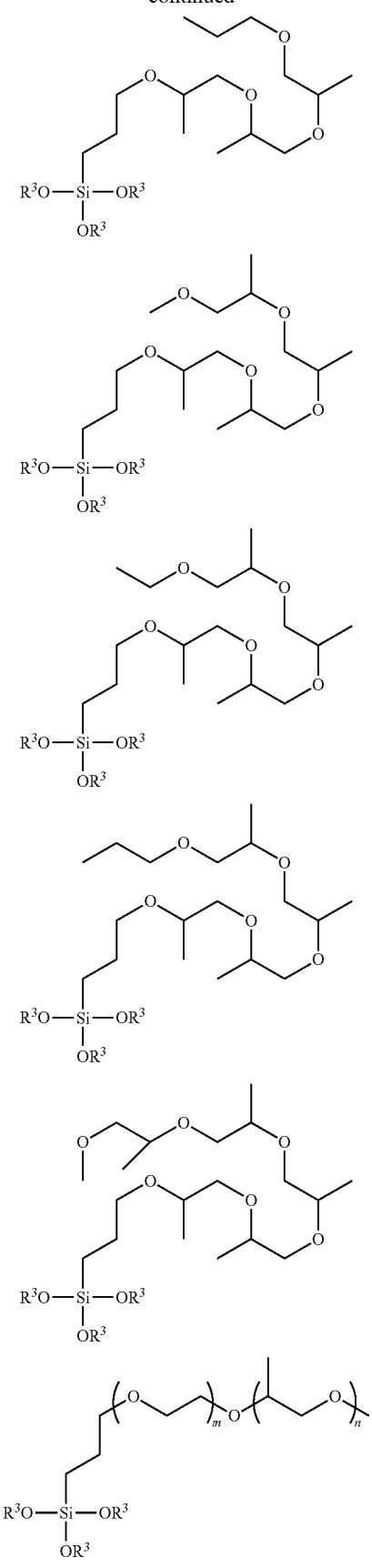

-continued
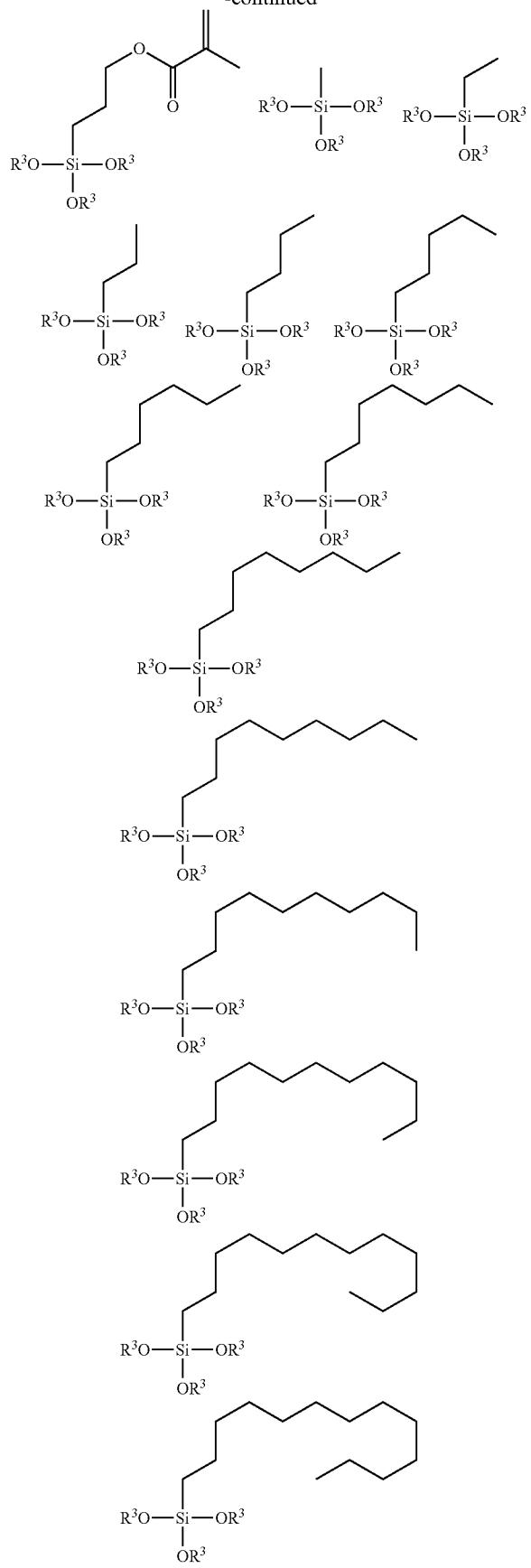
-continued
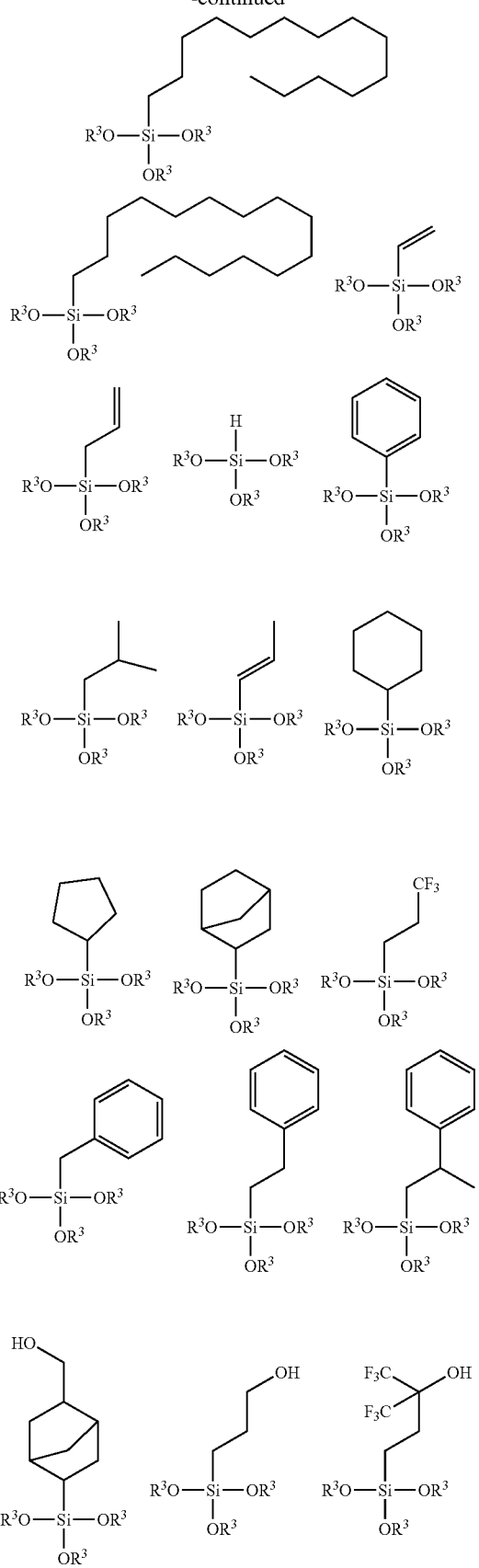

-continued
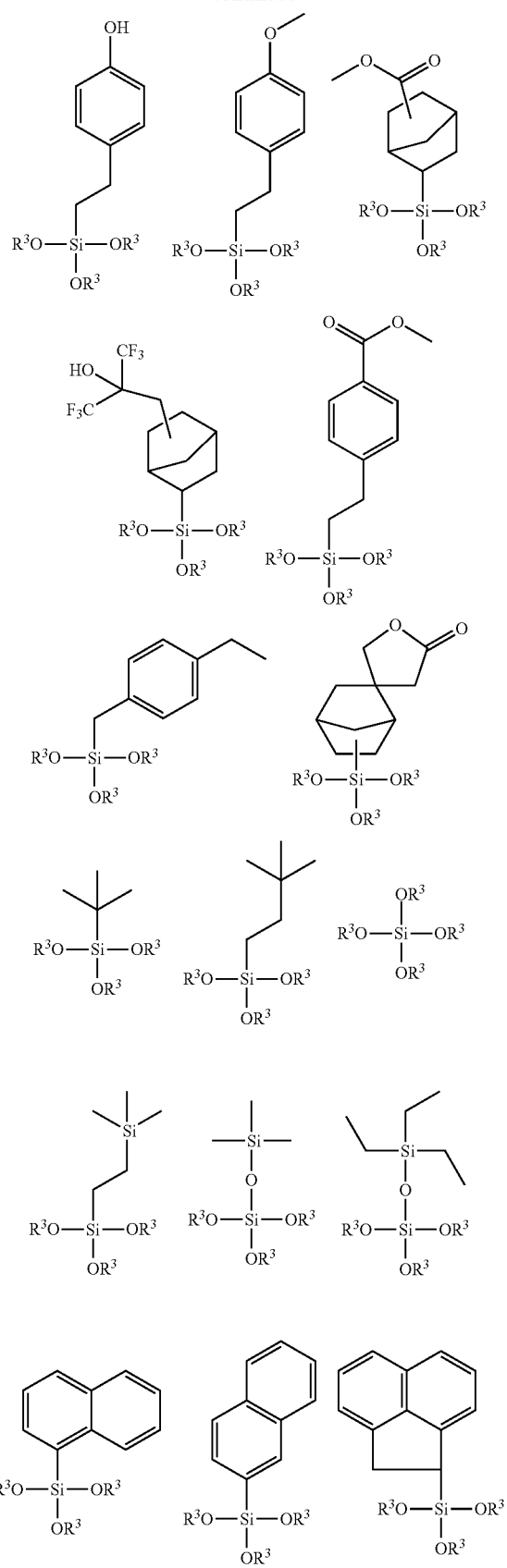
-continued
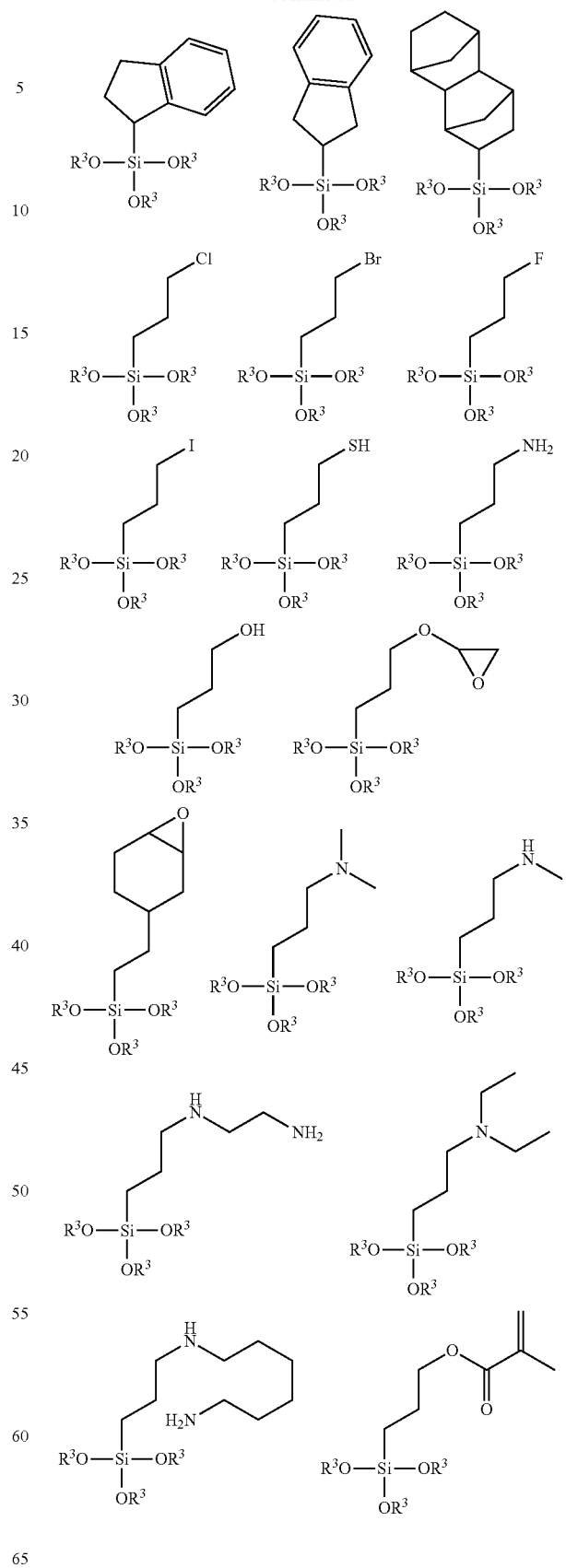

-continued

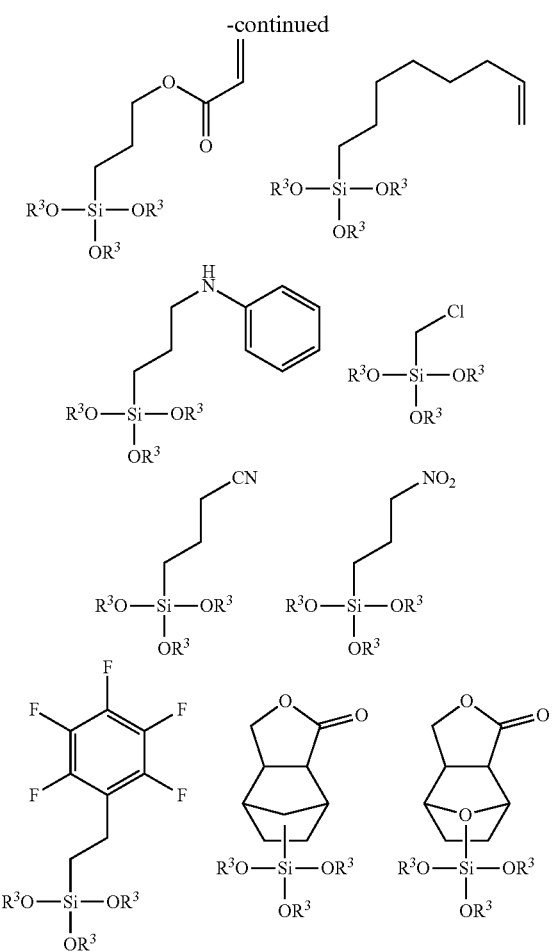

R³ is as defined above. "m" and "n" each represent an integer of 0 to 100.

As one method for synthesizing the silicon material particles as the component (A) having an N-carbonyl sulfonamide salt in a pendant form on the surfaces, a precursor trialkoxysilane and silicon material particles are subjected to condensation reaction. As a method for synthesizing the precursor compound shown by the general formula (2), the precursor compound can be obtained by hydrosilylation reaction between an N-carbonyl sulfonamide salt having a double bond and a trialkoxysilane compound having an Si—H group in the presence of a platinum catalyst. This synthesis method is specifically disclosed in JP 2020-6069 A.

The compound obtained in this manner can be shown by the following general formula (2).

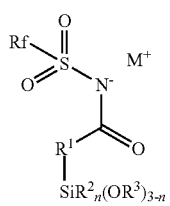

(2)

In the formula, R¹, Rf, and M⁺ are as defined above. R² and R³ are identical to or different from each other and each represent a hydrogen atom, or a linear, branched, or cyclic alkyl group having 1 to 10 carbon atoms. "n" represents 0 or 1.

As the reaction method between the trialkoxysilane and silicon material particles, it is possible to employ, for example, the methods disclosed in paragraphs [0065] to [0073] of JP 2020-33224 A and in WO 2015-186596 A1. The component (A) is preferably obtained by reacting 5 parts by mass or more of the alkoxysilane compound shown by the general formula (2) relative to 100 parts by mass of the silicon material particles.

Having a pendant of an N-carbonyl sulfonamide salt on the surfaces of the silicon material particles reduces the permeability through the skin and the irritation to the skin. Thus, the composition can be more surely prevented from permeating the skin and causing allergies.

Further, attaching an N-carbonyl sulfonamide salt to the silicon material particle surfaces forms ion conduction path on the silicon material particle surfaces, and can increase the sensitivity as a bio-electrode.

The silicon material particles in the state of primary particles have a median diameter (D50) within a range of preferably 2 nm to 50 μm, more preferably 3 nm to 30 μm, further preferably 4 nm to 20 μm. Note that, in the present invention, particle diameters can be determined by a laser diffraction method.

The synthesis method of the silicon material particles is not particularly limited, and may be either dry or wet synthesis method. Examples of the silicon material particles can include powders of silica particles, elemental silicon (Si), silicon monoxide (SiO), silicon carbide (SiC), silicon oxycarbide, silicate, etc. Among these, preferable silicon material particles are any of silica particles, Si particles, SiO particles, and SiC particles, or silicon material powder selected from composites thereof. Alternatively, the silicon material particles may be silicon particles having silica attached on the surfaces as disclosed in JP 2015-3839 A. The shape of the silicon material particles may be any of spherical, elliptical, irregular, hollow, and porous shapes. Meanwhile, the insides of the silicon material particles may be a metal or resin. It is also possible to use particles obtained by treating silicone particle surfaces with ozone or oxygen plasma to convert the surfaces into silica compound. When porous silicon material particles are treated with an alkoxysilane containing an N-carbonyl sulfonamide salt shown by the general formula (2), the N-carbonyl sulfonamide salt-containing alkoxysilane permeates and is attached to not only the surfaces but also the insides of the silicon material particles in some cases. In this manner, the N-carbonyl sulfonamide salt does not always have to be attached only to the surfaces of the silicon material particles.

The inventive particles having an N-carbonyl sulfonamide salt on the surfaces are promising materials not only for bio-electrode applications but also for negative electrode materials of ion batteries. Particularly, when the N-carbonyl sulfonamide salt-containing alkoxysilane is combined with silicon powder, the N-carbonyl sulfonamide salt can suppress the deformation of the silicon powder due to intercalation of ions which move in and out when charging and discharging are repeated.

In the inventive bio-electrode composition, the component (A) is blended in an amount of preferably 0.1 to 300 parts by mass, more preferably 1 to 200 parts by mass, relative to 100 parts by mass of the component (B). Additionally, one kind of the component (A) may be used alone, or two or more kinds thereof may be used in mixture.

In some cases, not all of trialkoxysilanes of N-carbonyl sulfonamide salt shown by the general formula (2) are consumed in the reaction with the silicon material particles. In this case, trialkoxysilanes of N-carbonyl sulfonamide salt condense with each other to form a silsesquioxane as described in JP 2020-6069 A. Even when a silsesquioxane having the N-carbonyl sulfonamide salt is mixed, this does not lower the performance as a bio-electrode, or does not increase the irritation to skin.

[Component (B)]

Besides the component (A), the inventive bio-electrode composition can contain the component (B), which is an adhesive resin. The component (B) blended in the bio-electrode composition is a component compatibilized (well mixed) with the ionic particle material (A) (N-carbonyl sulfonamide salt particles) to prevent elution of the salt, and this component also functions to hold an electric conductivity improver such as a carbon powder and a metal powder, and exhibit adhesion. Note that the component (B) may be any resin other than the component (A), and is preferably either or both of a thermosetting resin and a photo-curable resin, particularly preferably one or more resins selected from the group consisting of a silicone resin (silicone-based resin), a (meth)acrylate resin (acrylic-based resin), and a urethane resin (urethane-based resin).

Examples of the adherent (adhesive) silicone-based resin include an addition reaction-curable (addition-curable) type and a radical crosslinking reaction-curable (radical curable) type. As the addition reaction-curable type, it is possible to use one that contains diorganosiloxane having an alkenyl group(s), an MQ resin having $R_3SiO_{0.5}$ and $SiO_2$ units, organohydrogenpolysiloxane having multiple SiH groups, a platinum catalyst, an addition-reaction inhibitor, and an organic solvent, for example, described in JP 2015-193803A. As the radical crosslinking reaction-curable type, it is possible to use one that contains diorganopolysiloxane with or without an alkenyl group, an MQ resin having $R_3SiO_{0.5}$ and $SiO_2$ units, organic peroxide, and an organic solvent, for example, described in JP 2015-193803A. Here, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols, and improves adhesive strength by addition of it, but does not bind to the polysiloxane in molecular level because it is not crosslinkable. The adhesive strength can be increased by integrating the polysiloxane and the resin as described above.

The silicone-based resin may contain modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the component (A) in the silicone resin. The modified siloxane may be modified at any part such as one terminal, both terminals, or a side chain of the siloxane.

As the adherent acrylic-based resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane-based resin, it is possible to use one having a urethane bond with a polyether bond, a polyester bond, a polycarbonate bond, or a siloxane bond described in JP 2016-065238A, for example.

In the inventive bio-electrode composition, the adhesive resin of the component (B) preferably has high compatibility with the component (A) to prevent lowering of the electric conductivity due to separation of the component (A) from the living body contact layer. In the inventive bio-electrode composition, the resin of the component (B) preferably has high adhesion to the electro-conductive base material to prevent peeling of the living body contact layer from the electro-conductive base material. In order to increase the adhesion to the electro-conductive base material and the compatibility with the salt, a use of a resin with high polarity as the resin of the component (B) is effective. Examples of such a resin include resin having one or more moieties selected from an ether bond, an ester bond, an amide bond, an imide bond, a urethane bond, a thiourethane bond, and a thiol group: a polyacrylic resin, a polyamide resin, a polyimide resin, a polyurethane resin, a polythiourethane resin; etc. On the other hand, the living body contact layer is to be contacted with a living body, thereby being susceptible to perspiration. Accordingly, in the inventive bio-electrode composition, the resin of the component (B) preferably has high repellency and is hardly hydrolyzed. To make the resin of the component (B) be highly repellent and hardly hydrolyzed, the use of a silicon-containing resin is effective.

The silicon atom-containing polyacrylic resin includes a polymer that has a silicone main chain and a polymer that has a silicon atom(s) on the side chain, either of which can be suitably used. As the polymer that has a silicone main chain, silsesquioxane, siloxane having a (meth)acrylpropyl group, or the like can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680B, for example. Such polyamide silicone resins can be synthesized by combining, for example, a silicone or non-silicone compound having amino groups at both terminals and a non-silicone or silicone compound having carboxyl groups at both terminals.

It is also possible to use polyamic acid before cyclization thereof, which is obtained by reacting carboxylic anhydride and amine. The carboxyl group of the polyamic acid may be crosslinked by using a crosslinking agent such as an epoxy type and an oxetane type. It is also possible to esterify the carboxyl group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-cross-linked as described in JP 2005-320418A. It is also possible to photo-crosslink a polymer having both of a siloxane bond(s) and a urethane bond(s), with the terminal having a (meth)acrylate group(s).

The silicon atom-containing polythiourethane resin can be obtained by reaction of a compound having a thiol group(s) and a compound having an isocyanate group(s), provided that either of them contains a silicon atom(s). It can also be photo-cured if (meth)acrylate groups are contained at the terminals.

The silicone-based resin can be improved in compatibility with the foregoing salt by adding modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R_3SiO_{0.5}$ and $SiO_2$ units, and the organohydrogenpolysiloxane having multiple SiH groups.

As will be described later, the living body contact layer is a cured product of the bio-electrode composition. The curing improves the adhesion of the living body contact layer to both of skin and the electro-conductive base material. The curing means is not particularly limited, and common means can be used, including crosslinking reaction by either or both of heat and light, or with an acid catalyst or a base catalyst, for example. The crosslinking reaction can be performed, for example, by appropriately selecting methods described in "Kakyou han-nou handbook (handbook of crosslinking reaction)", Chapter 2, pages 51-371, Yasuharu Nakayama, Maruzen Publishing Co., Ltd. (2013).

The diorganosiloxane having an alkenyl group(s) and the organohydrogenpolysiloxane having multiple SiH groups can be crosslinked through an addition reaction with a platinum catalyst (component (F)).

Examples of the platinum catalyst include platinum-based catalysts such as chloroplatinic acid, alcohol solution of chloroplatinic acid, reaction product of chloroplatinic acid and alcohol, reaction product of chloroplatinic acid and an olefin compound, reaction product of platinic chloride and vinyl group-containing siloxane, a platinum-olefin complex, and a complex of platinum and vinyl group-containing siloxane; platinum group metal-based catalysts such as a rhodium complex and a ruthenium complex; etc. These catalysts may be used after dissolved or dispersed in alcohol solvent, hydrocarbon solvent, or siloxane solvent.

Note that the platinum catalyst is added in an amount preferably within 5 to 2,000 ppm, particularly preferably 10 to 500 ppm, relative to 100 parts by mass of the resin of the component (B).

When the addition-curable silicone resin is used, an addition-reaction inhibitor (component (F)) may be added. This addition-reaction inhibitor is added as a quencher to prevent the action of the platinum catalyst in the solution and under a low temperature circumstance after forming the coating film and before heat curing. Specific examples of the addition-reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The addition-reaction inhibitor is added in an amount preferably within 0 to 10 parts by mass, particularly preferably 0.05 to 3 parts by mass, relative to 100 parts by mass of the resin of the component (B).

Examples of the method for photo-curing the component (B) include: a method of adding a photoradical generator (component (F)) to generate radical by light, together with using a resin having a (meth)acrylate terminal(s) or an olefin terminal(s) or adding a crosslinking agent with the terminal (s) being (meth)acrylate, olefin, or a thiol group(s); and a method of adding a photo-acid generator (component (F)) to generate acid by light, together with using a resin or a crosslinking agent having an oxirane group(s), an oxetane group(s), or a vinyl ether group(s).

Examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type (component (F)). Examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane]hydrochloride, 2,2'-azobis(4-methoxy-2,4-dimethylvaleronitrile), 2,2'-azobis (cyclohexane-1-carbonitrile), 1[(1-cyano-1-methylethyl) azo]formamide, 2,2'-azobis[2-methyl-N-(2-hydroxyethyl) propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dicumyl peroxide, etc.

Examples of the photo-acid generator include sulfonium salt, iodonium salt, sulfonyldiazomethane, N-sulfonyloxyimide, oxime-O-sulfonate type acid generators, etc. Specific examples of the photo-acid generator include ones described in paragraphs [0122] to [0142] of JP 2008-111103A, and in JP 2009-080474A.

Note that the radical generator or the photo-acid generator is added in an amount preferably within 0.1 to 50 parts by mass relative to 100 parts by mass of the resin of the component (B).

Above all, the resin of the component (B) more preferably contains diorganosiloxane having an alkenyl group, and organohydrogenpolysiloxane having an SiH group. Particularly preferably, the resin of the component (B) further contains a silicone resin having an $SiO_2$ unit and an $R_xSiO_{(4-x)/2}$ unit, where R represents a substituted or unsubstituted monovalent hydrocarbon group having 1 to 10 carbon atoms, and "X" represents a number in a range of 2.5 to 3.5.

[Component (C)]

The inventive bio-electrode composition can also contain the component (C), which is a polymer compound having an ion component as a repeating unit (ionic repeating unit), in order to further enhance the ionic conductivity.

The ionic repeating unit preferably contains a repeating unit-c having a structure selected from the group consisting of salts of ammonium, sodium, potassium, and silver formed with any of fluorosulfonic acid, fluorosulfonimide, and N-carbonyl-fluorosulfonamide.

Further, the ionic repeating unit preferably has a structure shown by any of the following general formulae (3)-1 to (3)-4.

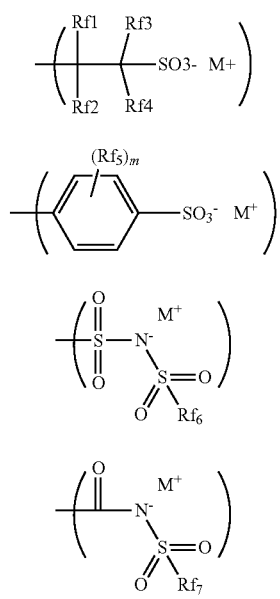

In the formulae, $Rf_1$ and $Rf_2$ each represent a hydrogen atom, a fluorine atom, an oxygen atom, a methyl group, or a trifluoromethyl group. When $Rf_1$ and $Rf_2$ represent an oxygen atom, the single oxygen atom represented by $Rf_1$ and $Rf_2$ bonds to a single carbon atom to form a carbonyl group. $Rf_3$ and $Rf_4$ each represent a hydrogen atom, a fluorine atom, or a trifluoromethyl group. At least one of $Rf_1$ to $Rf_4$ is a fluorine atom or a trifluoromethyl group. $Rf_5$, $Rf_6$, and $Rf_7$ each represent a fluorine atom, or a linear or branched alkyl group having 1 to 4 carbon atoms, and have at least one fluorine atom. $M^+$ represents an ion selected from the group consisting of an ammonium ion, a sodium ion, a potassium ion, and a silver ion. "m" represents an integer of 1 to 4.

Further, the ionic repeating unit is preferably selected from c1 to c7 in the following general formula (3

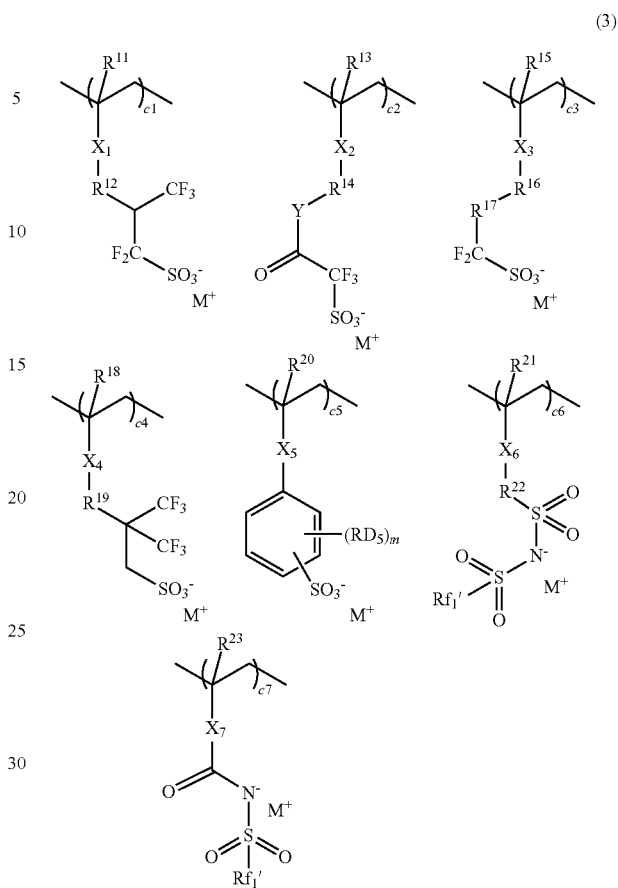

In the formula, $R^{11}$, $R^{13}$, $R^{15}$, $R^{18}$, $R^{20}$, $R^{21}$, and $R^{23}$ each independently represent a hydrogen atom or a methyl group. $R^{12}$, $R^{14}$, $R^{16}$, $R^{19}$, and $R^{22}$ each independently represent a single bond, or a linear, branched, or cyclic hydrocarbon group having 1 to 12 carbon atoms. The hydrocarbon group optionally has either or both of an ester group and an ether group. $R^{17}$ represents a linear or branched alkylene group having 1 to 4 carbon atoms, and one or two hydrogen atoms in $R^{17}$ are optionally substituted with a fluorine atom. $X_1$, $X_2$, $X_3$, $X_4$, $X_6$, and $X_7$ each independently represent any of a single bond, a phenylene group, a naphthylene group, an ether group, an ester group, and an amide group. $X_5$ represents any of a single bond, an ether group, and an ester group. Y represents an oxygen atom or a $—NR^{29}—$ group. $R^{29}$ represents a hydrogen atom, or a linear or branched alkyl group having 1 to 4 carbon atoms. $Rf_1'$ represents a fluorine atom or a trifluoromethyl group. $Rf_5$ represents a fluorine atom, or a linear or branched alkyl group having 1 to 4 carbon atoms and at least one fluorine atom. "m" represents an integer of 1 to 4. c1, c2, c3, c4, c5, c6, and c7 satisfy $0 \leq c1 \leq 1.0$, $0 \leq c2 \leq 1.0$, $0 \leq c3 \leq 1.0$, $0 \leq c4 \leq 1.0$, $0 \leq c5 \leq 1.0$, $0 \leq c6 \leq 1.0$, $0 \leq c7 \leq 1.0$, and $0 \leq c1+c2+c3+c4+c5+c6+c7 \leq 1.0$. $M^+$ represents an ion selected from the group consisting of an ammonium ion, a sodium ion, a potassium ion, and a silver ion.

Monomers for obtaining the ionic repeating unit selected from c1 to c7 in the general formula (3) are specifically disclosed in paragraphs [0062] to [0111] of JP 2020-002342 A. Monomers copolymerized therewith, copolymerization ratios, polymerization methods, molecular weights, etc. disclosed in paragraphs [0112] to [0135] can be adopted herein.

[Component (D)]

The inventive bio-electrode composition can further contain the component (D), which is an electro-conductive powder. The electro-conductive powder is not particularly limited, as long as the powder has electric conductivity. The electro-conductive powder is preferably a carbon powder (carbon material) or a metal powder. Although the inventive bio-electrode composition contains the component (A) (the particles having an N-carbonyl sulfonamide salt on the surfaces) as an ionic material (salt), the electric conductivity can be further enhanced by additionally adding such an electro-conductive powder (carbon powder, metal powder). Incidentally, hereinafter, the electro-conductive powder may also be referred to as "electric conductivity improver".

[Carbon Powder]

A carbon material (carbon powder) can be added as an electric conductivity improver. Examples of the carbon material include carbon black, carbon nanotube, carbon fiber, etc. The carbon nanotube may be either single layer or multilayer, and the surface may be modified with an organic group(s). The carbon material is added in an amount preferably within 1 to 50 parts by mass relative to 100 parts by mass of the resin of the component (B).

[Metal Powder]

The inventive bio-electrode composition preferably contains a metal powder selected from the group consisting of gold, silver, platinum, copper, tin, titanium, nickel, aluminum, tungsten, molybdenum, ruthenium, chromium, and indium as the component (D) in order to improve electron conductivity. The metal powder is added in an amount preferably within 1 to 50 parts by mass relative to 100 parts by mass of the resin of the component (B).

As the kind of the metal powder, gold, silver, and platinum are preferable from the viewpoint of electric conductivity; and silver, copper, tin, titanium, nickel, aluminum, tungsten, molybdenum, ruthenium, and chromium are preferable from the viewpoint of cost. From the viewpoint of biocompatibility, noble metals are preferable. From comprehensive viewpoint including the above, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of not more than 5 g/cm$^3$, and a specific surface area of not less than 0.5 m$^2$/g. Both of a metal powder and a carbon material (carbon powder) can be added as the electric conductivity improver.

[Silicon Powder]

The inventive bio-electrode composition may contain a silicon powder to enhance ion reception sensitivity. Examples of the silicon powder include powders of silicon, silicon monoxide, or silicon carbide. The particle diameter of the powder is preferably smaller than 100 μm, more preferably 1 μm or less. Since finer particles have a larger surface area, the resulting bio-electrode can receive a larger amount of ions and has higher sensitivity. The silicon powder is added in an amount preferably within 1 to 50 parts by mass relative to 100 parts by mass of the resin of the component (B).

[Lithium Titanate Powder]

The inventive bio-electrode composition may contain a lithium titanate powder to enhance ion reception sensitivity. Examples of the lithium titanate powder include powders containing a compound shown by molecular formulae $Li_2TiO_3$, $LiTiO_2$, or $Li_4Ti_5O_{12}$ with a spinel structure. The lithium titanate powder preferably has a spinel structure. It is also possible to use carbon-incorporated lithium titanate particles. The particle diameter of the powder is preferably smaller than 100 μm, more preferably 1 μm or less. Since finer particles have a larger surface area, the bio-electrode can receive a larger amount of ions, and has higher sensitivity. The aforementioned powders may be composite powders with carbon. The lithium titanate powder is added in an amount preferably within 1 to 50 parts by mass relative to 100 parts by mass of the resin of the component (B).

[Component (E)]

Further, the inventive bio-electrode composition may contain the component (E), which is an organic solvent. Specific examples of the organic solvent include: aromatic hydrocarbon solvents, such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvents, such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3- dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvents, such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvents, such as 3-methoxybutanol, 3-methyl-3-methoxybutanol, 1-methoxy-2-propanol, and 1-ethoxy-2-propanol; ether solvents, such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvents, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvents, such as γ-butyrolactone; etc.

Note that the organic solvent is added in an amount preferably within 10 to 50,000 parts by mass relative to 100 parts by mass of the resin of the component (B). When the inventive bio-electrode composition contains the component (E) of an organic solvent, the bio-electrode composition has further favorable coating property.

[Component (F)]

The inventive bio-electrode composition can further contain a component (F) which is an additive, as necessary. The additive is different from the above-described components (A) to (E), and is not particularly limited. Examples of the additive can include: components that can enhance the stretchability or adhesion of a cured product of the bio-electrode composition, such as tackifier; components for promoting or suppressing the curing reaction, such as radical generator, photo-acid generator, platinum catalyst, and addition-reaction inhibitor as described in the section of the component (B); moisture-holding components, such as polyether, polyglycerin, polyglycerin ester, polyether silicone, and polyglycerin silicone; salts for enhancing the ionic conductivity, such as sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaine.

[Tackifier]

The inventive bio-electrode composition may also contain a tackifier in order to have adhesion to a living body. Examples of such a tackifier include silicone resin, non-crosslinkable siloxane, non-crosslinkable poly(meth)acrylate, non-crosslinkable polyether, etc. Although the inventive bio-electrode composition can optionally contain an adhesive resin as the component (B), adding such a tackifier can attain further preferable adhesion to a living body.

[Silicone Compound having Polyglycerin Structure]

The inventive bio-electrode composition may contain a silicone compound having a polyglycerin structure to enhance the sensitivity to ions released from skin and the ionic conductivity by enhancing the moisture-holding property of the film. The silicone compound having a polyglycerin structure is blended in an amount of preferably 0.01 to 100 parts by mass, more preferably 0.5 to 60 parts by mass, relative to 100 parts by mass of a total of the components (A) and (B). Additionally, one kind of the silicone compound having a polyglycerin structure may be used alone, or two or more kinds thereof may be used in mixture.

The silicone compound having a polyglycerin structure is preferably shown by any of the following general formulae (4) and (5).

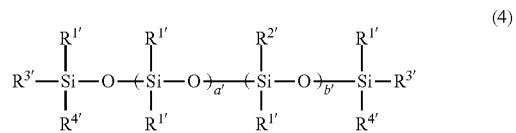

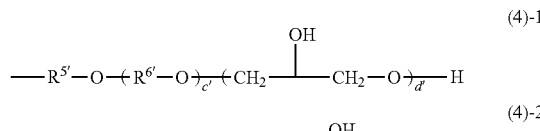

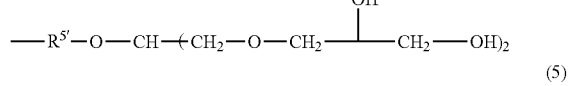

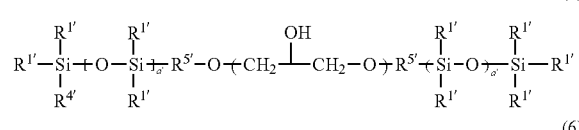

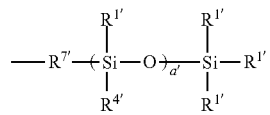

In the formulae (4) and (5), each $R^{1'}$ is identical to or different from one another, and independently represents a hydrogen atom, a phenyl group, a linear or branched alkyl group having 1 to 50 carbon atoms, or a silicone chain shown by a general formula (6), and optionally contains an ether group. $R^{2'}$ represents a group having a polyglycerin group structure shown by a formula (4)-1 or (4)-2. Each $R^{3'}$ is identical to or different from the other, and independently represents the $R^{1'}$ group or the $R^{2'}$ group. Each $R^{4'}$ is identical to or different from the other, and independently represents the $R^{4'}$ group, the $R^{2'}$ group, or an oxygen atom. When $R^{4'}$ represents an oxygen atom, the two $R^{4'}$ moieties bond to each other and optionally constitute an ether group to form a ring together with silicon atoms. Each a' is identical to or different from one another and represents 0 to 100, b' represents 0 to 100, and a'+b' is 0 to 200. Nevertheless, when b' is 0, at least one $R^{3'}$ is the $R^{2'}$ group. In the formulae (4)-1 and (4)-2, $R^{5'}$ represents an alkylene group having 2 to 10 carbon atoms or an aralkylene group having 7 to 10 carbon atoms. $R^{6'}$ and $R^{7'}$ each represent an alkylene group having 2 to 6 carbon atoms, but $R^{7'}$ may represent an ether bond. c' represents 0 to 20. d' represents 1 to 20.

Examples of such a silicone compound having a polyglycerin structure can include the following.

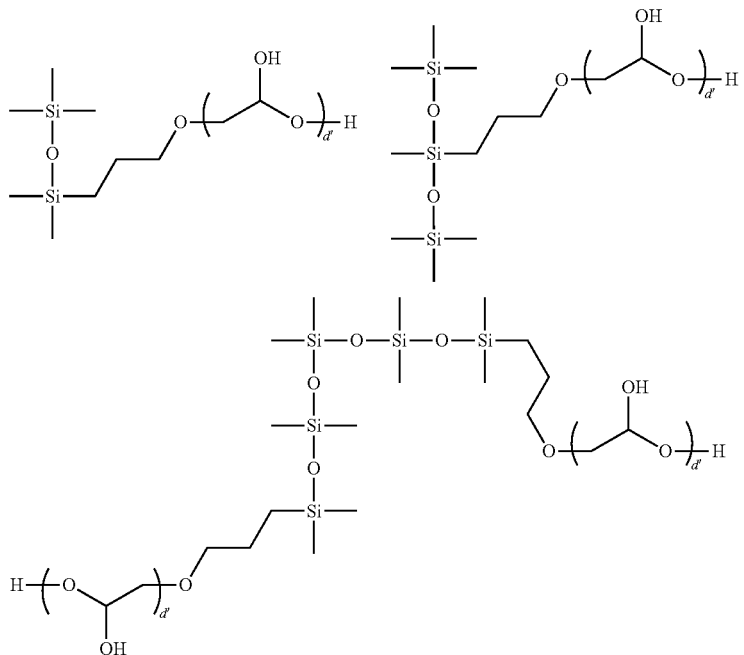

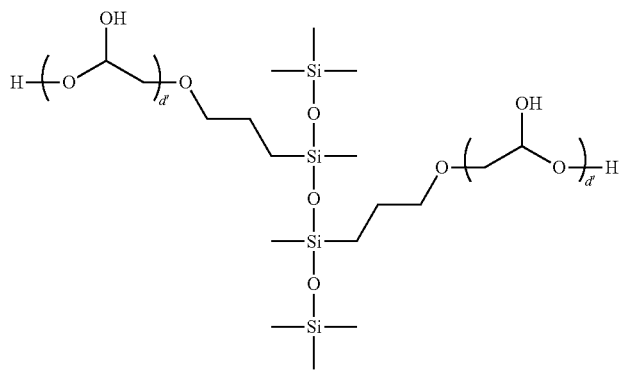

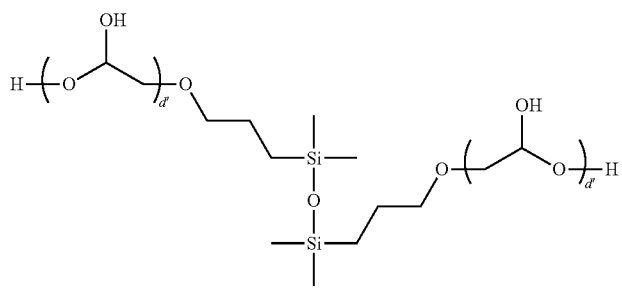

-continued
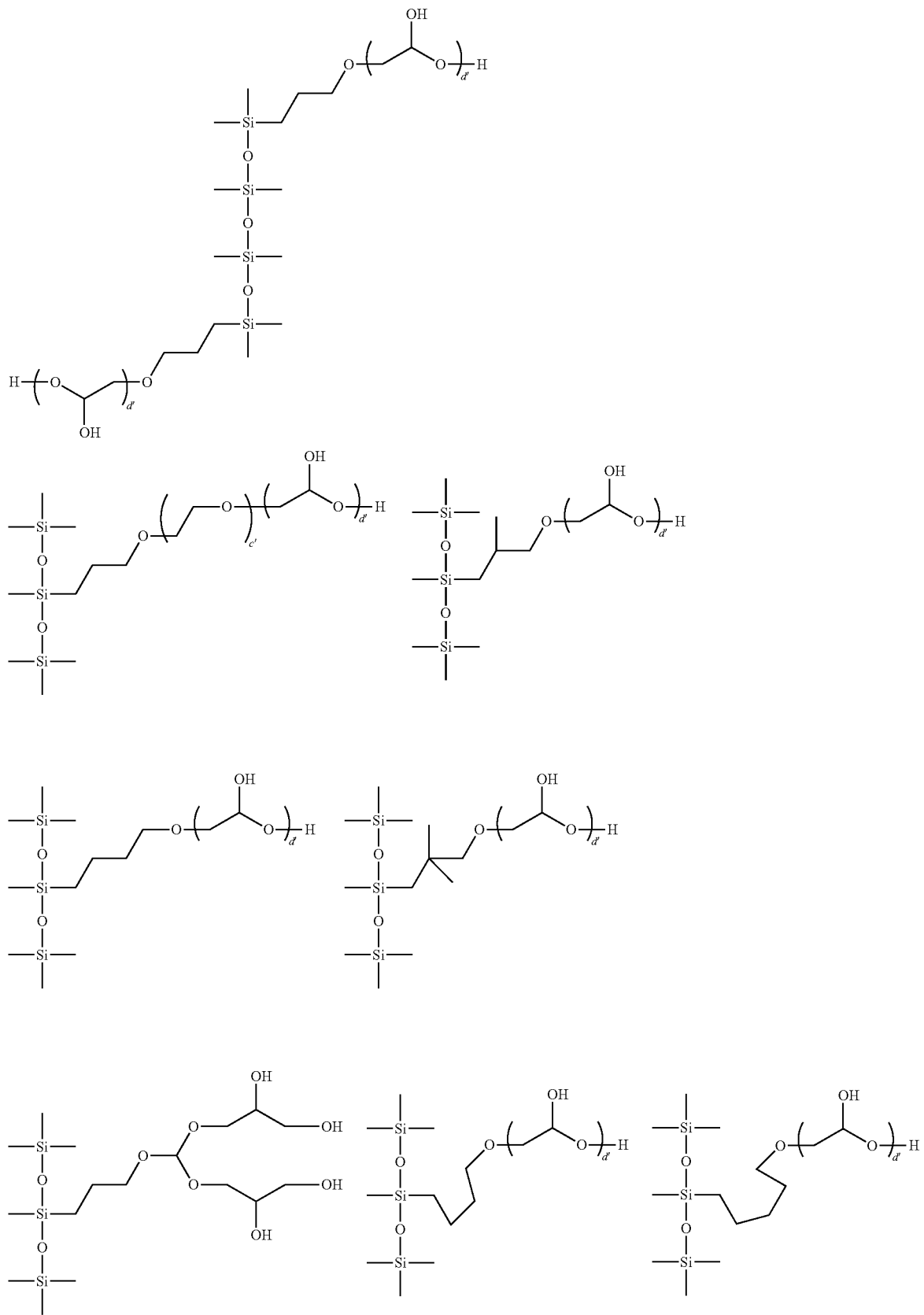

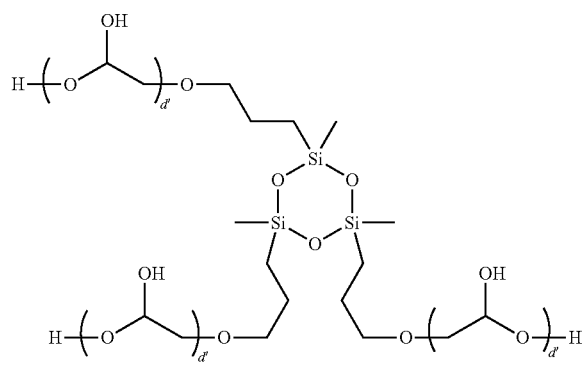
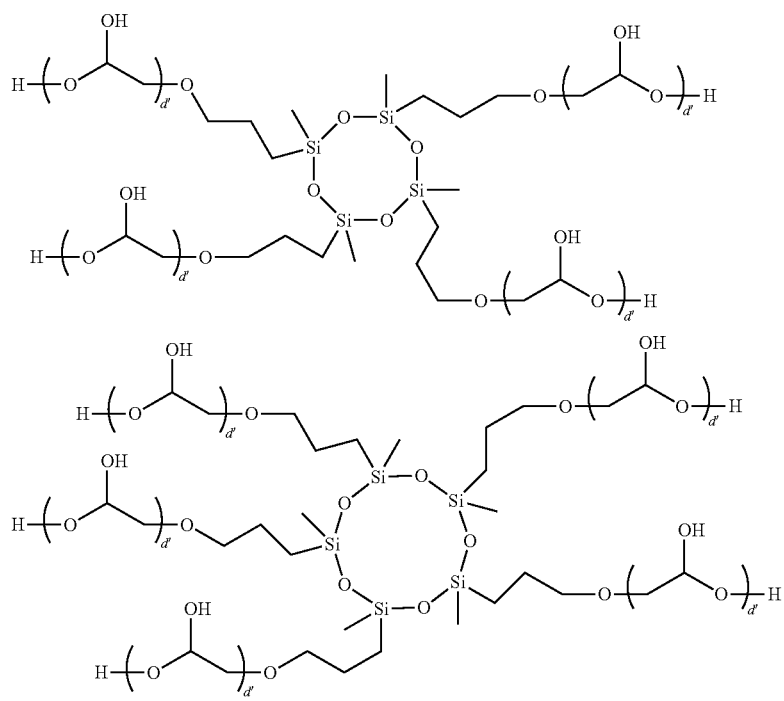
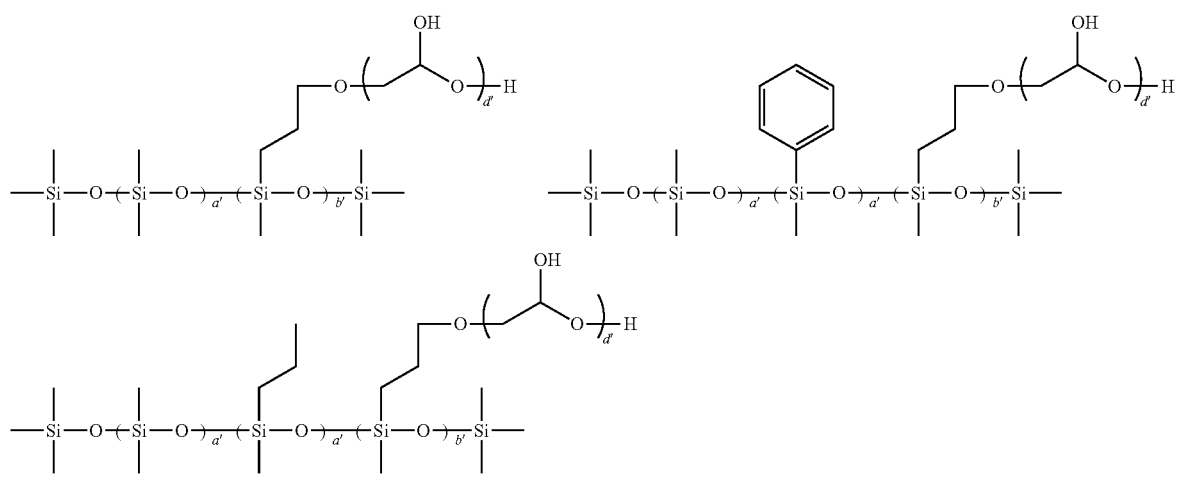

-continued
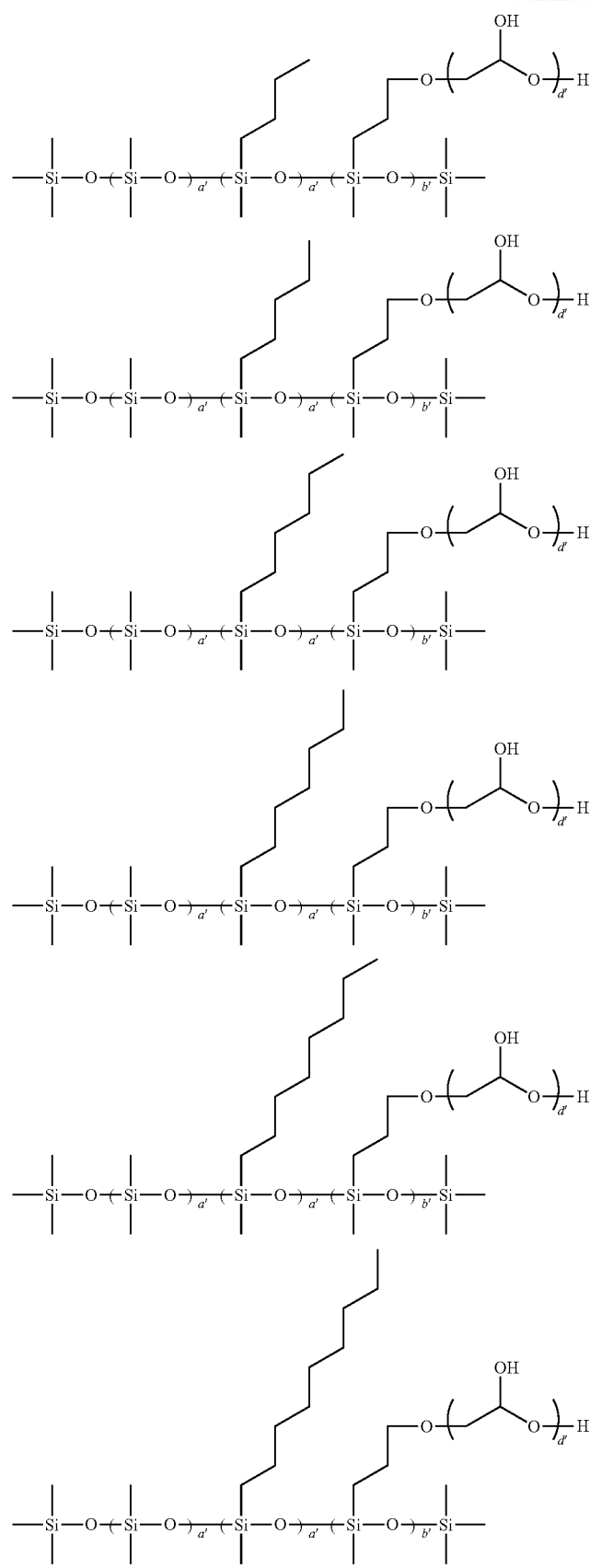

-continued
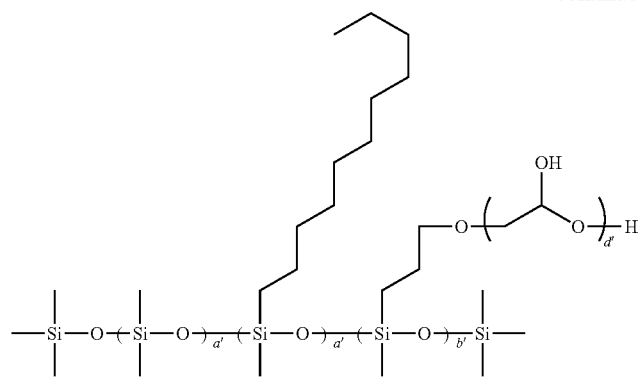
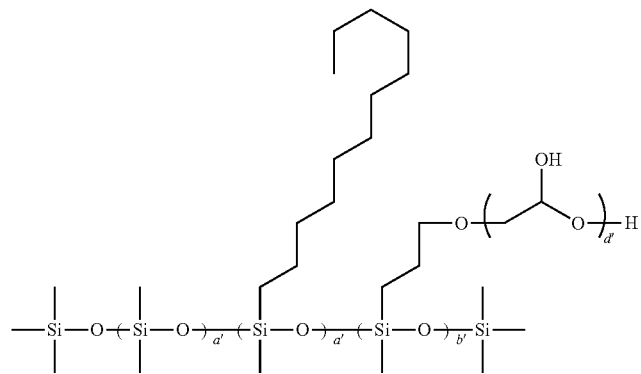
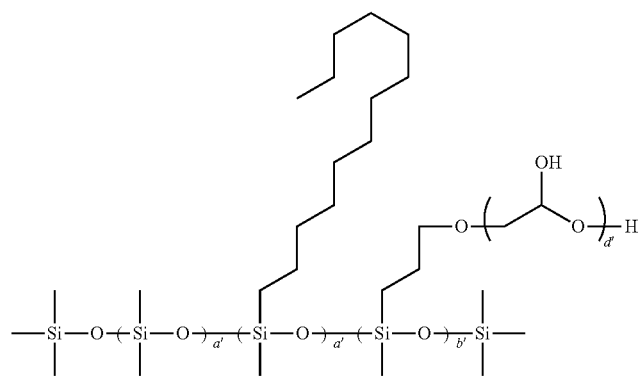
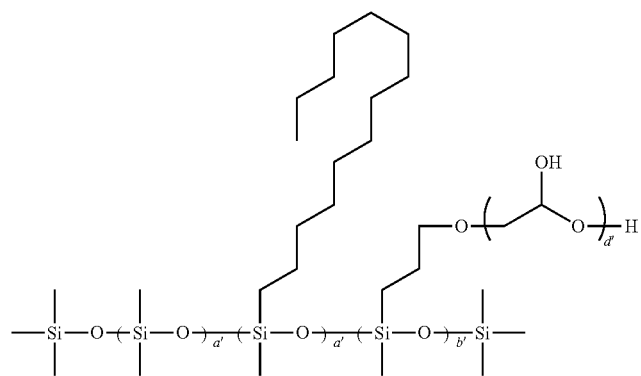

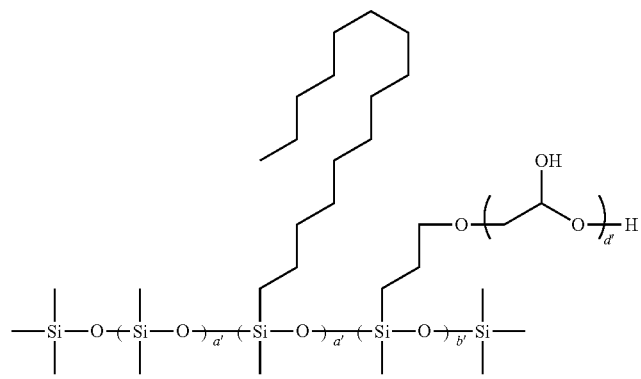
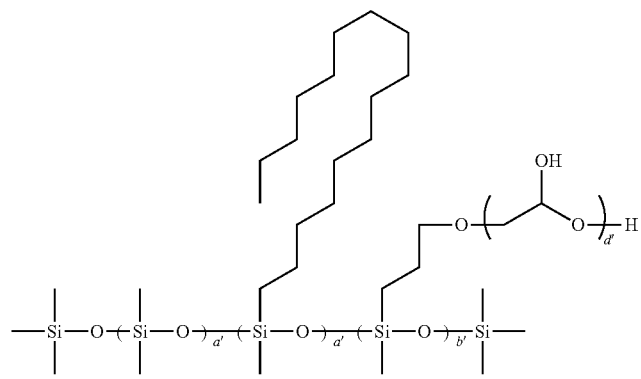
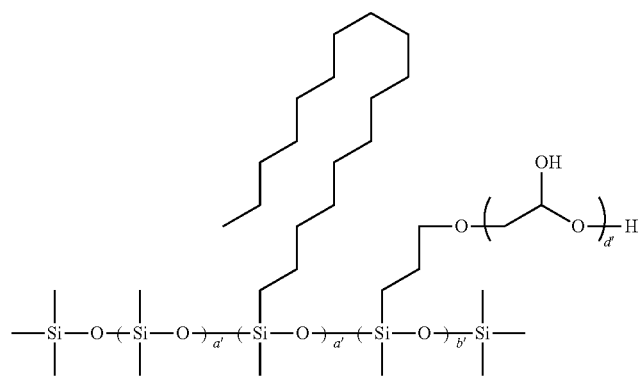
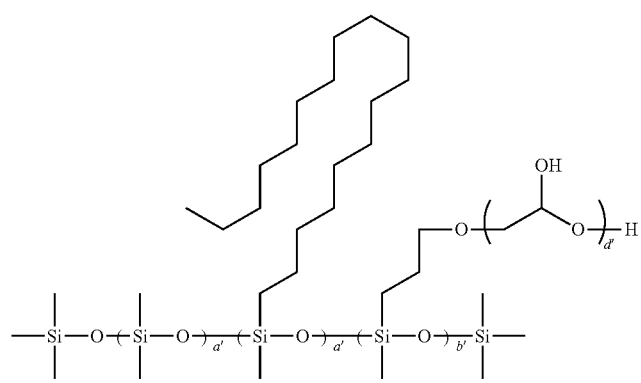

-continued
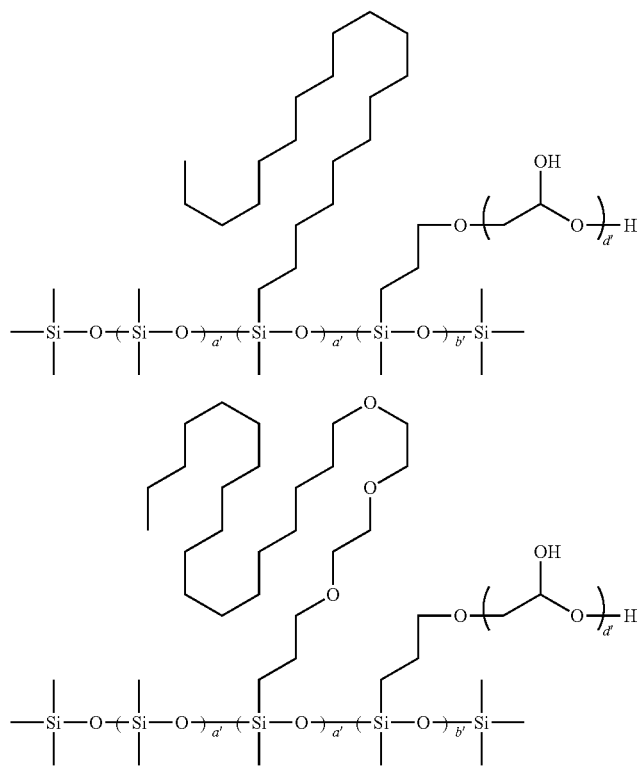
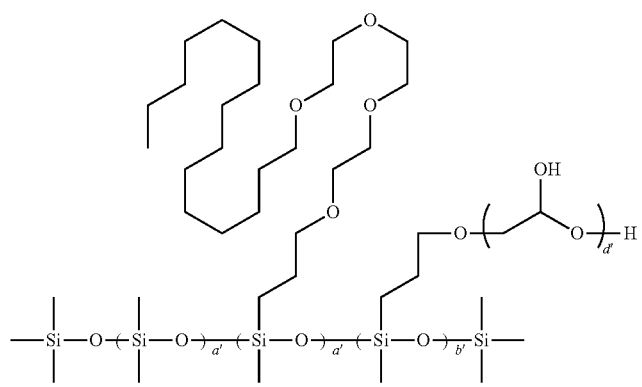
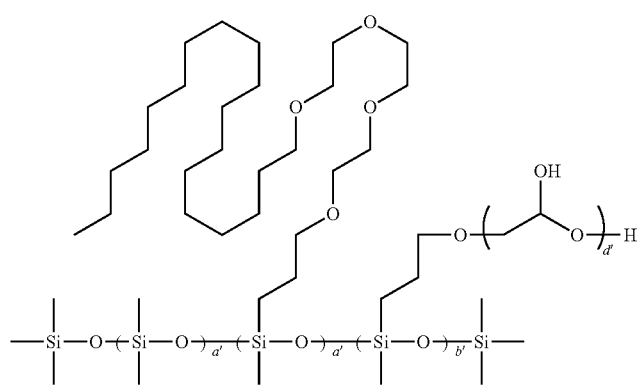

-continued
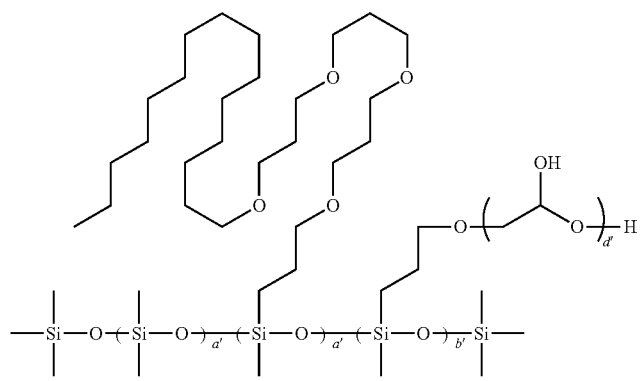
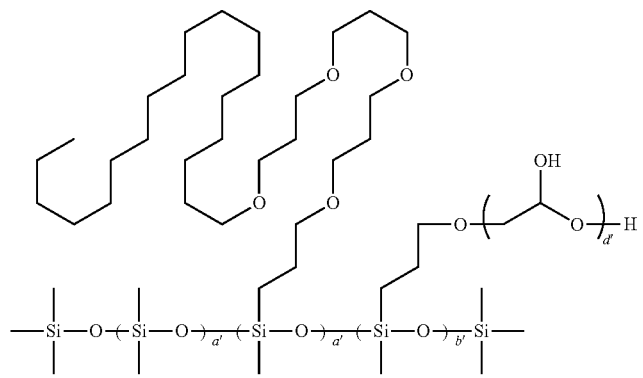
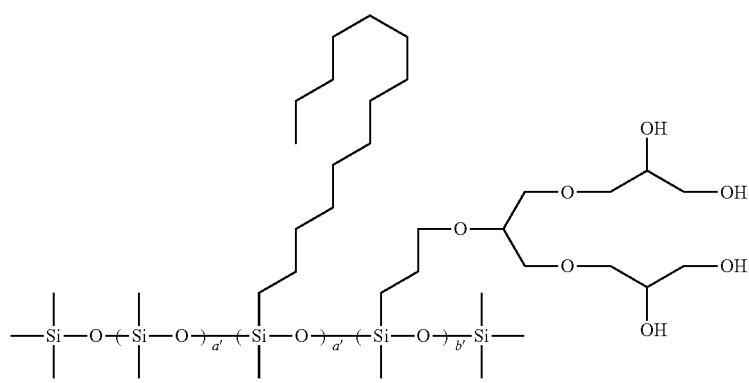
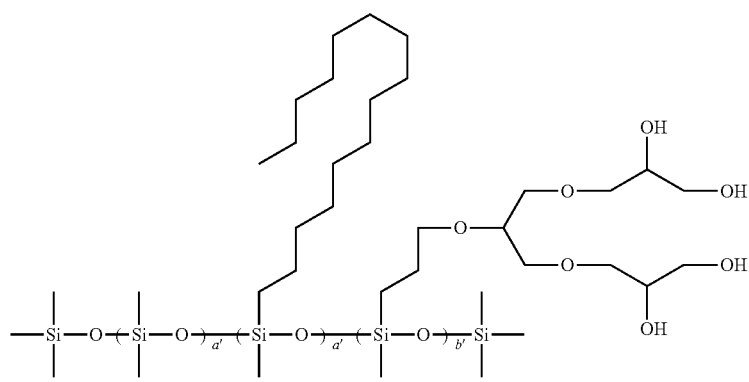

-continued
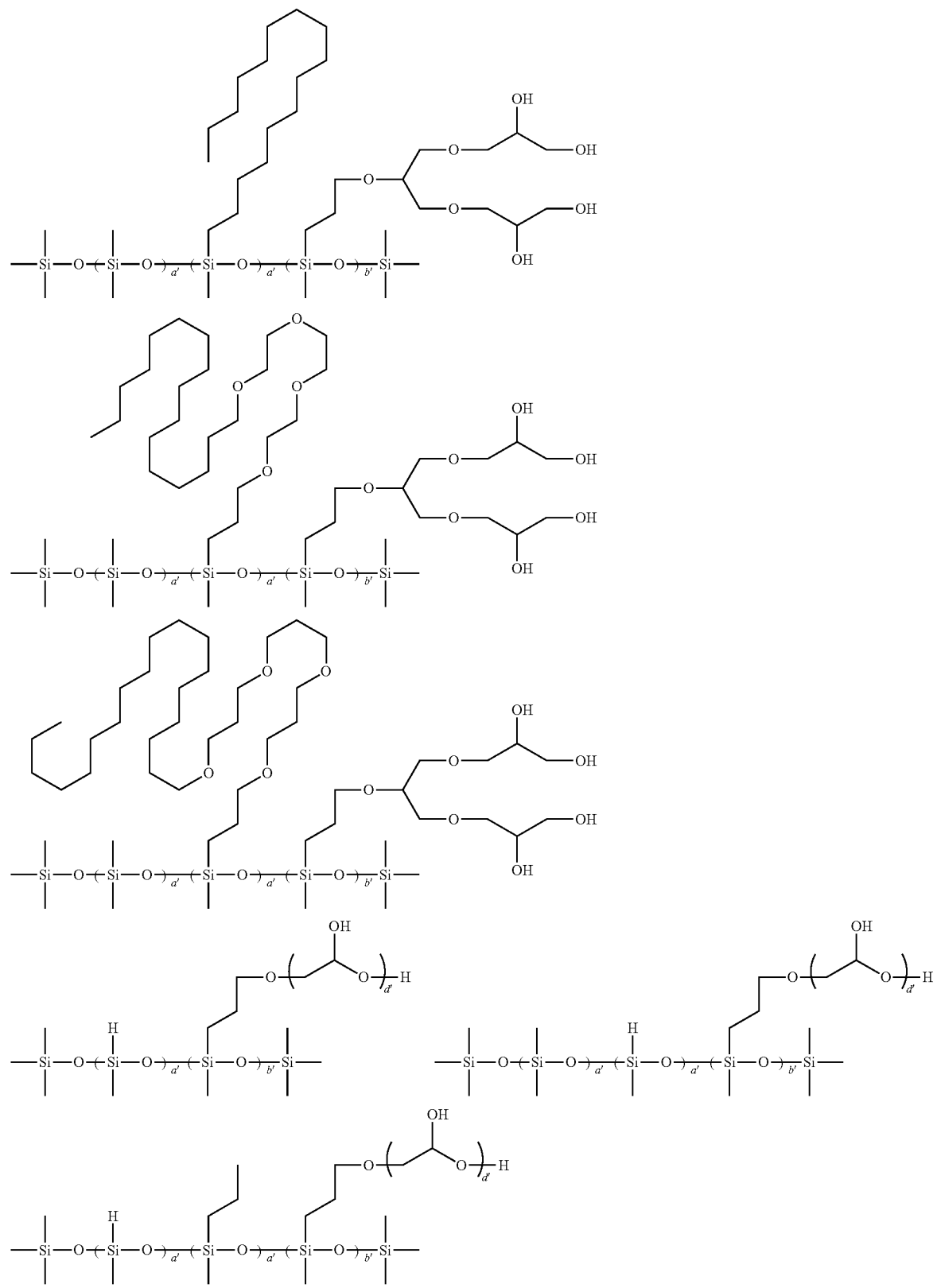

-continued
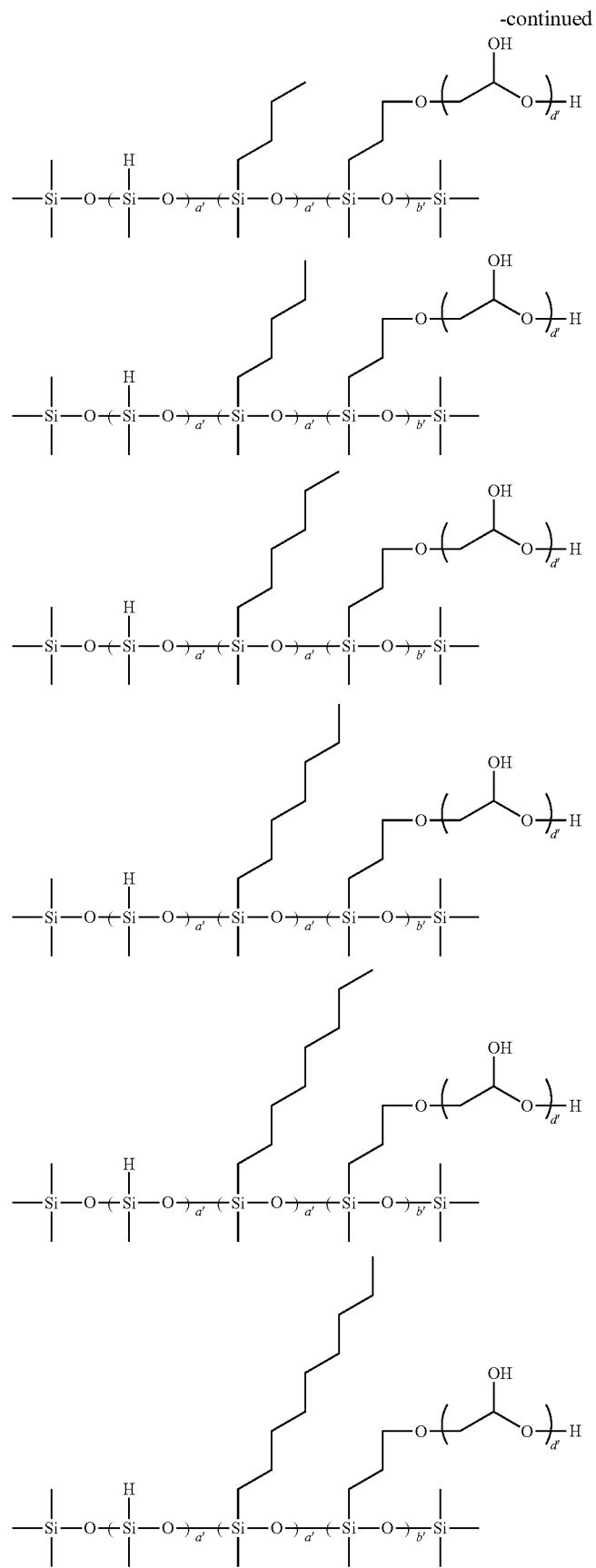

-continued
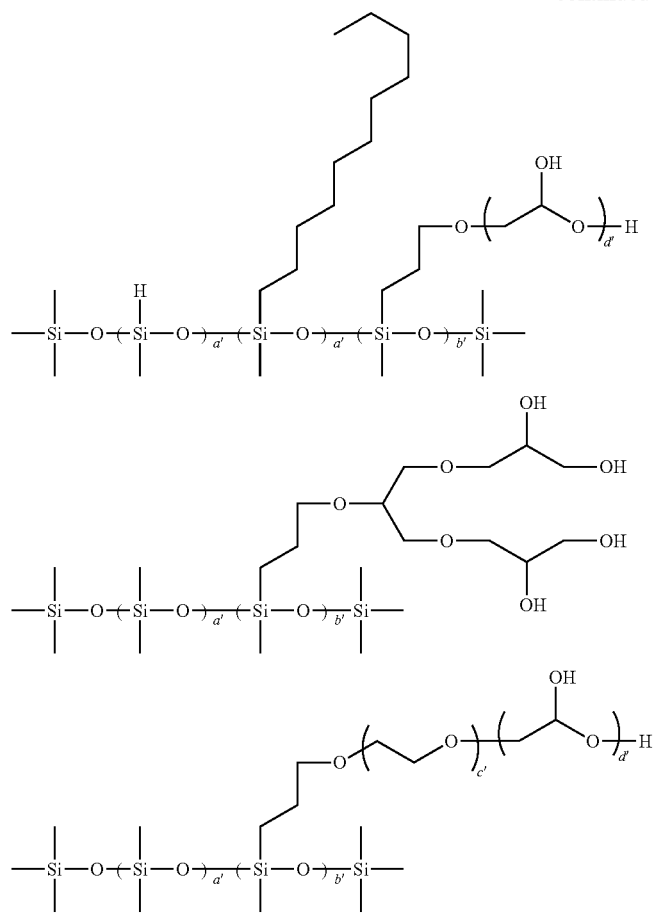
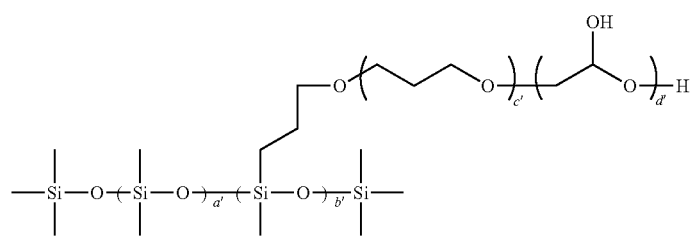
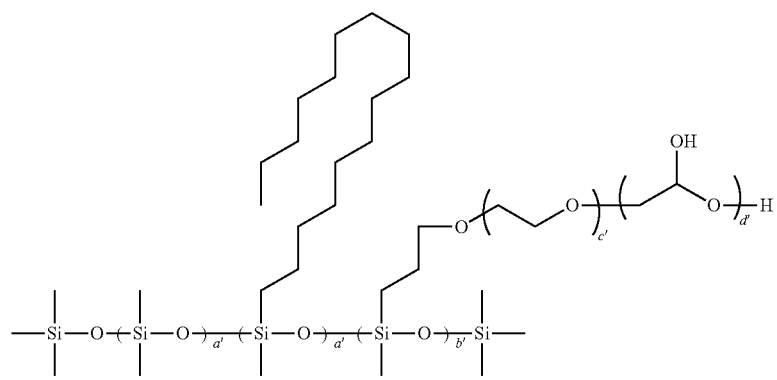

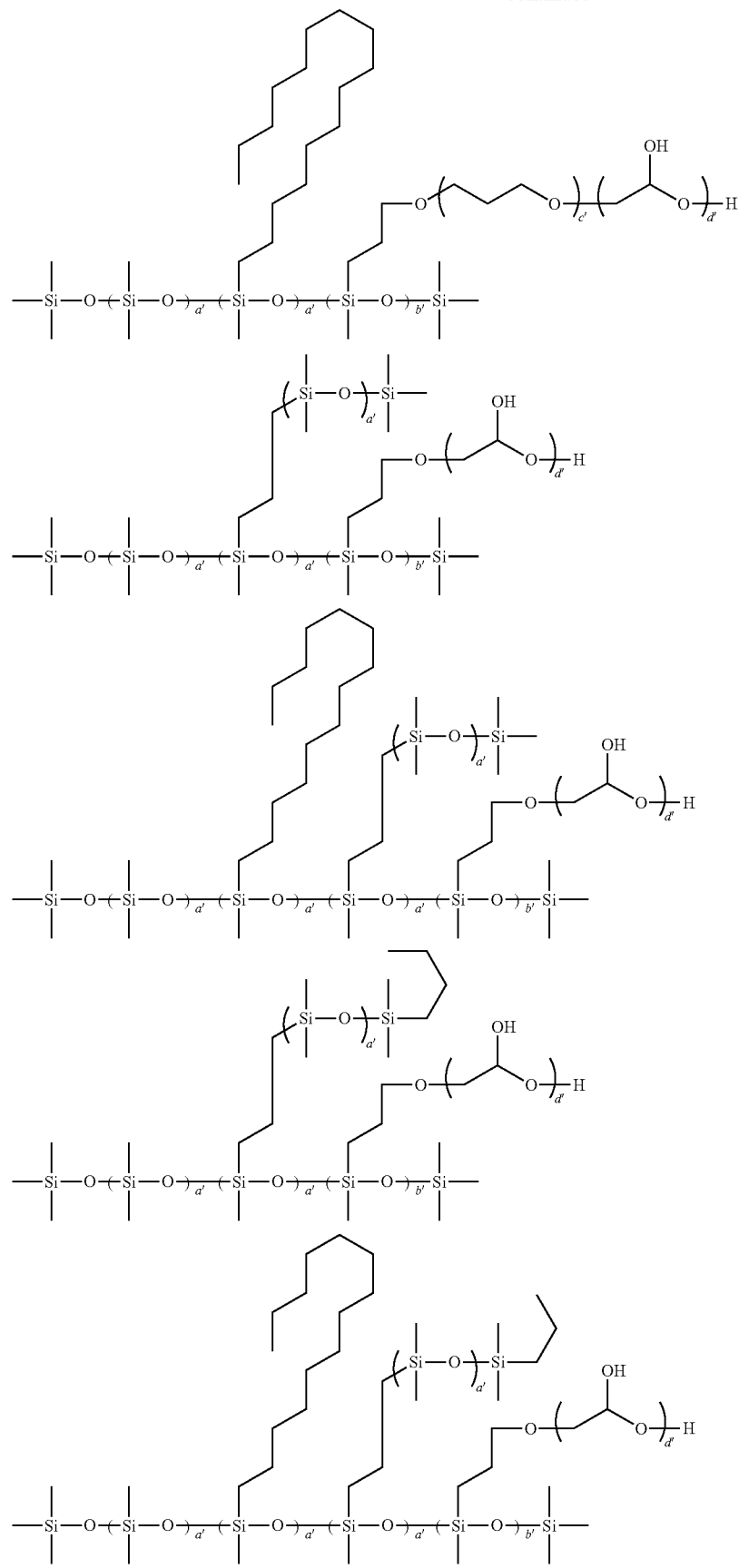

-continued
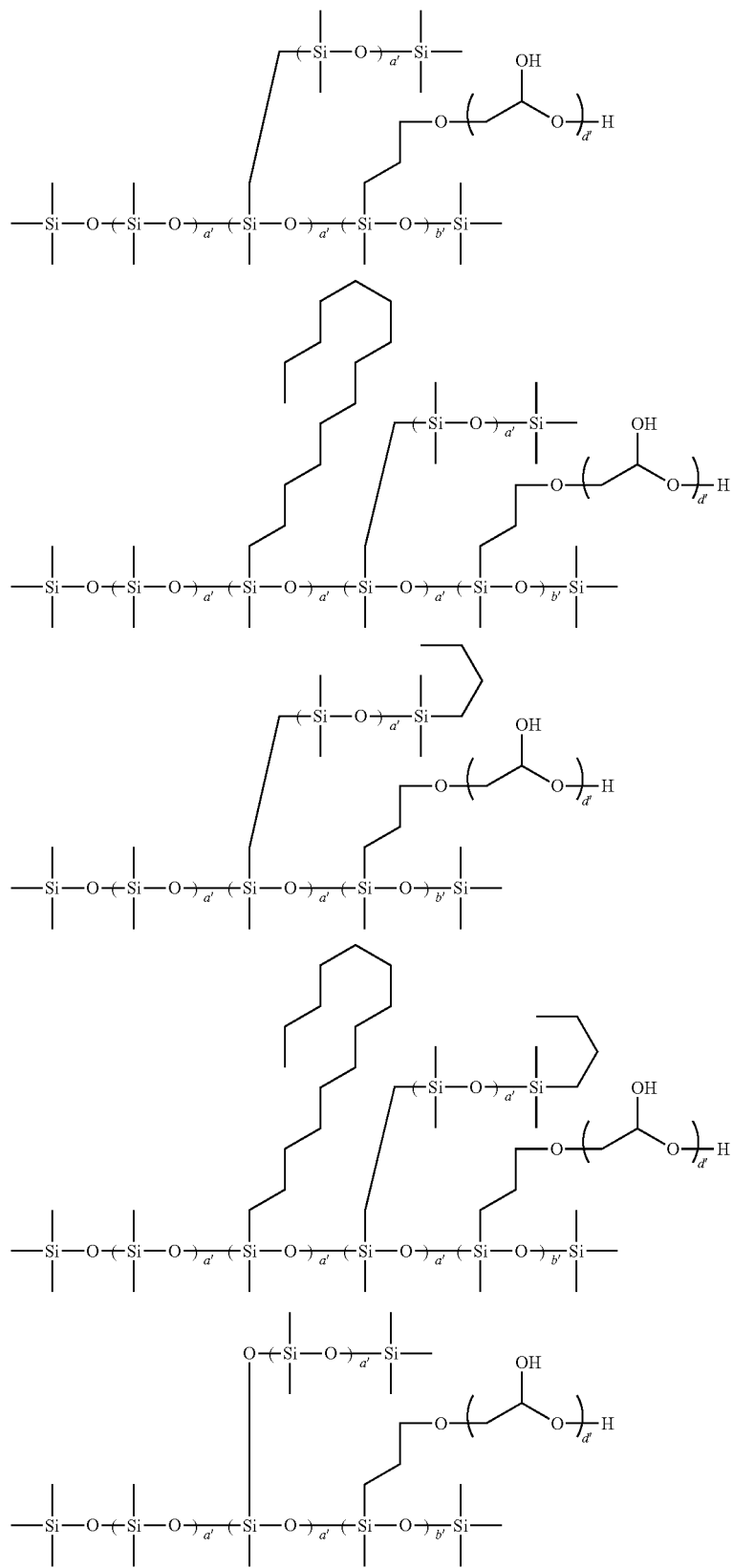

-continued
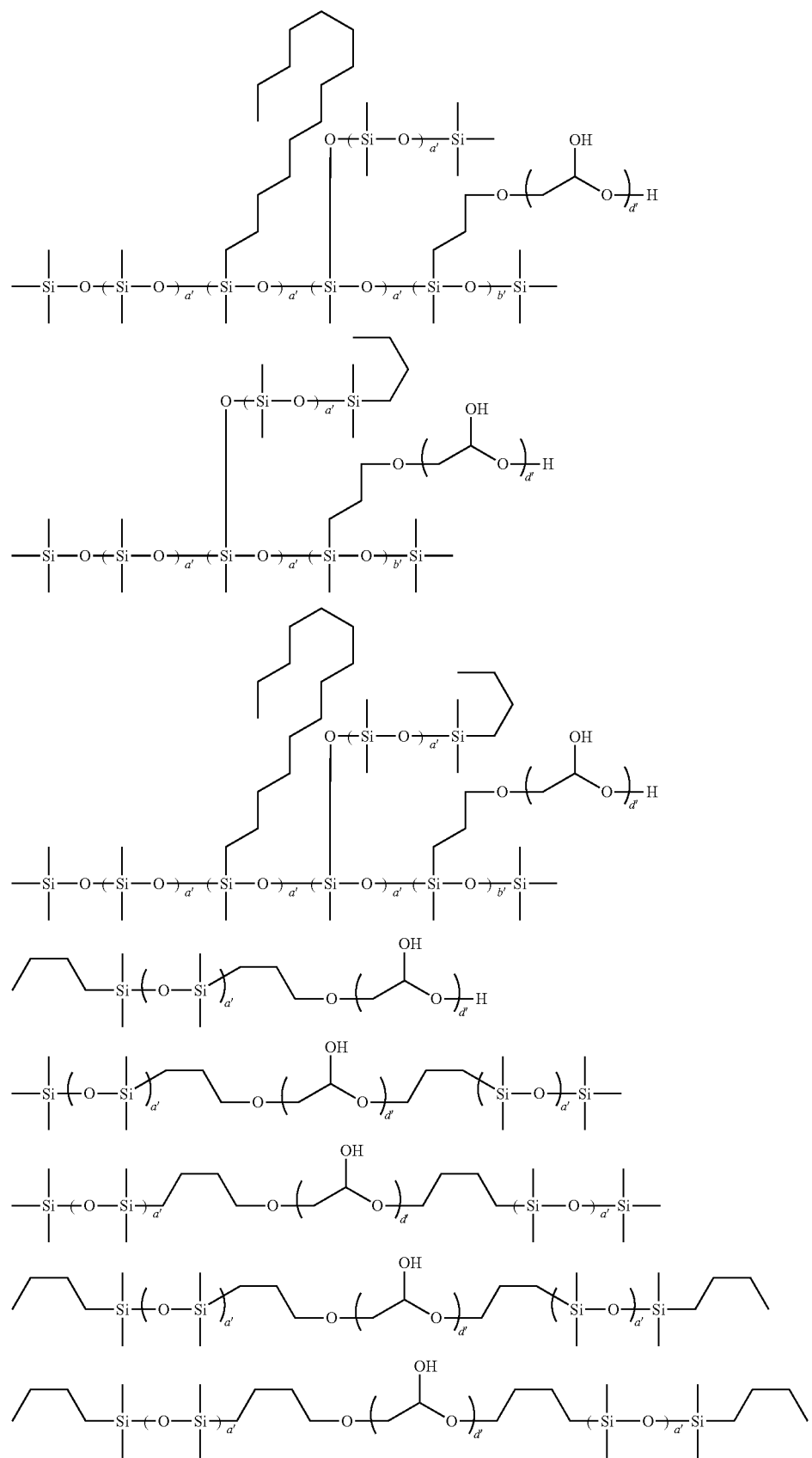

-continued

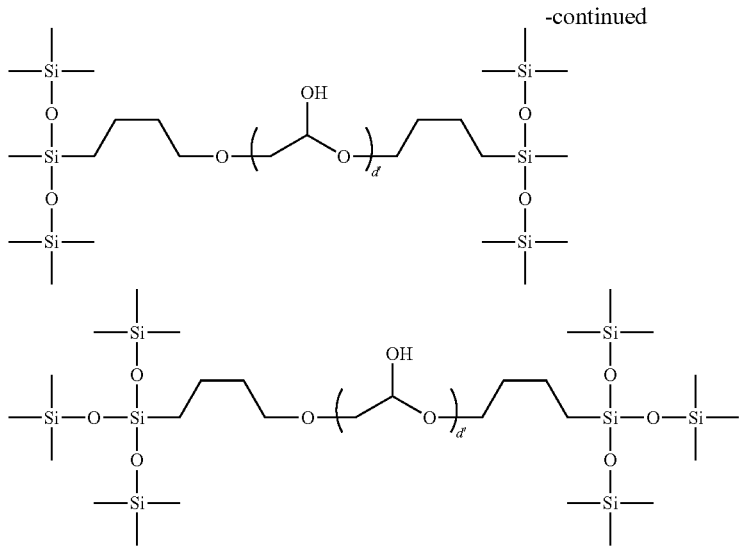

In the formulae, a', b', c', and d' are as defined above.

When such a silicone compound having a polyglycerin structure is incorporated, the resulting bio-electrode composition is capable of forming a living body contact layer that can exhibit more excellent moisture-holding property and consequently exhibit more excellent sensitivity to ions released from skin.

As has been described above, the inventive bio-electrode composition makes it possible to form a living body contact layer for a bio-electrode that is capable of efficiently conducting electric signals from skin to a device (i.e., excellent in electric conductivity), free from a risk of causing allergies even when the bio-electrode is attached to skin for a long period (i.e., excellent in biocompatibility), light-weight, manufacturable at low cost, and free from significant reduction in the electric conductivity even when the bio-electrode is wetted with water or dried. Moreover, it is possible to further enhance the electric conductivity by adding electro-conductive powder (carbon powder, metal powder), and it is possible to manufacture a bio-electrode with particularly high adhesive strength and high stretchability by combining the inventive bio-electrode composition with a resin having adhesion and stretchability. Further, the stretchability and adhesion to skin can be enhanced with an additive and so forth. The stretchability and adhesion can also be controlled by appropriately adjusting the composition of the resin and the thickness of the living body contact layer.

<Bio-Electrode>

The present invention also provides a bio-electrode including an electro-conductive base material and a living body contact layer formed on the electro-conductive base material, the living body contact layer being a cured product of the inventive bio-electrode composition described above.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is formed from a cured product of the inventive bio-electrode composition. The living body contact layer 3 is constituted of ionic particles 4 that are the particles having an N-carbonyl sulfonamide salt on the surfaces (e.g., the silicon material particles modified with an N-carbonyl sulfonamide salt). The living body contact layer 3 can further contain an adhesive resin 6 and an ionic polymer 5 other than the ionic particles 4. Hereinbelow, with reference to FIGS. 1 and 2, the living body contact layer 3 is described as a layer in which the ionic particles 4 and the ionic polymer 5 are dispersed in the adhesive resin 6. Nevertheless, the inventive bio-electrode is not limited to this embodiment.

When the bio-electrode 1 as shown in FIG. 1 is used, the living body contact layer 3 (i.e., the layer in which the ionic particles 4 and the ionic polymer 5 are dispersed in the adhesive resin 6) is brought into contact with a living body 7 as shown in FIG. 2. Electric signals are picked from the living body 7 through the ionic particles 4 and the ionic polymer 5, and then conducted to a sensor device or the like (not shown) via the electro-conductive base material 2. As described above, the inventive bio-electrode is capable of coping with both electric conductivity and biocompatibility by using the ionic particles 4 described above, and obtaining electric signals from skin stably in high sensitivity because the contact area with the skin is kept constant due to the adhesion thereof.

Hereinafter, each component of the inventive bio-electrode will be described more specifically.

[Electro-Conductive Base Material]

The inventive bio-electrode has an electro-conductive base material. This electro-conductive base material is usually connected electrically with a sensor device etc., and conducts electrical signals picked from a living body through the living body contact layer to the sensor device etc.

The electro-conductive base material is not particularly limited, as long as it has electric conductivity. The electro-conductive base material preferably contains one or more selected from the group consisting of gold, silver, silver chloride, platinum, aluminum, magnesium, tin, tungsten, iron, copper, nickel, stainless steel, chromium, titanium, carbon, and electro-conductive polymer, for example.

The electro-conductive base material may be a hard electro-conductive substrate, an electro-conductive film having flexibility, a cloth with the surface being coated with electro-conductive paste, a cloth into which electro-conductive polymer is kneaded, or the like without being limited to particular substrates. The electro-conductive base material may be flat, uneven, or mesh-form of woven metal wires, which can be appropriately selected in accordance with the use of the bio-electrode, and so forth.

[Living Body Contact Layer]

The inventive bio-electrode has a living body contact layer formed on the electro-conductive base material. This living body contact layer is a part to be actually in contact with a living body when using the bio-electrode. The living body contact layer has electric conductivity and adhesion. The living body contact layer is a cured product of the inventive bio-electrode composition described above; that is, an adherent resin layer formed from a cured composition containing: the component (A); and as necessary the component (B), the component (C), the component (D), the component (E), and the other component(s) (F).

The living body contact layer preferably has an adhesive strength in a range of 0.5 N/25 mm or more and 20 N/25 mm or less. The adhesive strength is commonly measured by the method described in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and the energy is as low as that of Teflon (registered trademark). Human skin is hard to adhere.

The living body contact layer of the bio-electrode has a thickness of preferably 1 μm or more and 5 mm or less, more preferably 2 μm or more and 3 mm or less. As the living body contact layer is thinner, the adhesive strength lowers, but the flexibility is improved, the weight decreases and the compatibility with skin is improved. The thickness of the living body contact layer can be selected based on the balance of adhesion and texture to the skin.

The inventive bio-electrode may be additionally provided with an adherent film on the living body contact layer as in conventional bio-electrodes (e.g., the bio-electrode described in JP 2004-033468A) in order to prevent peeling off of the bio-electrode from a living body during the use. When the adherent film is provided separately, the adherent film may be formed by using a raw material for the adherent film such as an acrylic type, a urethane type, and a silicone type. Particularly, the silicone type is suitable because of: the high oxygen permeability, which enables dermal respiration while the electrode is attached to the skin; the high water repellency, which suppresses lowering of adhesion due to perspiration; and the low irritation to skin. It is to be noted that the inventive bio-electrode does not necessarily require this adherent film that is provided separately, because peeling off from a living body can be prevented by adding a tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to employ ones described in JP 2004-033468A.

As described above, since the inventive bio-electrode includes the living body contact layer formed from the cured product of the aforementioned inventive bio-electrode composition, the inventive bio-electrode is capable of efficiently conducting electric signals from skin to a device (i.e., excellent in electric conductivity), does not cause allergies even after long-period attachment to skin (i.e., excellent in biocompatibility), is light-weight and manufacturable at low cost, and prevents significant reduction in the electric conductivity even when wetted with water or dried. In addition, it is possible to further improve the electric conductivity by adding an electro-conductive powder, and it is possible to manufacture a bio-electrode with particularly high adhesive strength and high stretchability by combining the inventive bio-electrode composition with a resin having adhesion and stretchability. Further, the stretchability and adhesion to skin can be improved with an additive and so forth. The stretchability and adhesion can also be controlled by appropriately adjusting the composition of the resin and the thickness of the living body contact layer. Accordingly, the inventive bio-electrode as described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, the method including:

applying the inventive bio-electrode composition onto the electro-conductive base material; and curing the bio-electrode composition to form the living body contact layer.

Note that the electro-conductive base material etc. used in the inventive method for manufacturing a bio-electrode may be the same as those described above.

The method for applying the bio-electrode composition onto the electro-conductive base material is not particularly limited. Examples of the suitable method include dip coating, spray coating, spin coating, roll coating, flow coating, doctor coating, screen printing, flexographic printing, gravure printing, inkjet printing, etc.

The method for curing the resin is not particularly limited and can be appropriately selected based on the kind of the components (A) and (B) used for the bio-electrode composition. For example, the bio-electrode composition is preferably cured by either or both of heat and light. The foregoing bio-electrode composition can also be cured by adding a catalyst in advance to generate acid or base to the bio-electrode composition, which causes a crosslinking reaction.

The heating temperature is not particularly limited and may be appropriately selected based on the kind of the components (A) and (B) used for the bio-electrode composition, but is preferably about 50 to 250° C., for example.

When the heating and light irradiation are combined, it is possible to perform the heating and the light irradiation simultaneously, to perform the light irradiation and then the heating, or to perform the heating and then the light irradiation. It is also possible to perform air-drying to evaporate the solvent before heating the coating film.

Water droplets may be attached to the surface of the cured film; alternatively, the film surface may be sprayed with water vapor or mist. These treatments improve the compatibility with skin, and enable quick collection of biological signals. Water mixed with alcohol can be used to reduce size of water vapor or mist. The film surface may be wetted by bringing an absorbent cotton or cloth containing water into contact therewith.

The water for making the surface of the cured film wet may contain a salt. The water-soluble salt mixed with the water is selected from the group consisting of sodium salts, potassium salts, calcium salts, magnesium salts, and betaines.

Specifically, the water-soluble salt can be a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines. It should be noted that the components (A) and (C) described above are excluded from the water-soluble salt.

More specific examples of the water-soluble salt include, besides the aforementioned examples, sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl sethionate, sodium lauroyl methylalanine, sodium methyl cocoyl taurate, sodium cocoyl glutamate, sodium cocoyl sarcosinate, sodium lauroyl methyl taurate, lauramidopropyl betaine, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, and calcium methanesulfonate. The term betaines is a general term for inner salts. Specific examples thereof include amino acid compounds in each of which three methyl groups are added to an amino group. More specific examples include trimethylglycine, carnitine, and proline betaines.

The water for wetting the surface of the cured film can further contain a monohydric alcohol or polyhydric alcohol having 1 to 4 carbon atoms. The alcohol is preferably selected from the group consisting of ethanol, isopropyl alcohol, ethylene glycol, diethylene glycol, triethylene glycol, glycerin, polyethylene glycol, polypropylene glycol, polyglycerin, diglycerin, and a silicone compound having a polyglycerin structure. More preferably, the silicone compound having a polyglycerin structure is shown by the general formula (4) or (5).

In the pretreatment methods with the aqueous solution containing the water-soluble salt, the cured bio-electrode film can be wetted by a spraying method, a droplet-dispensing method, etc. The bio-electrode film can also be wetted under a high-temperature, high-humidity condition like sauna. To prevent drying after the wetting, a protective film can be further stacked on the permeated layer to cover the surface. Since the protective film needs to be removed immediately before the bio-electrode is attached to skin, the protective film may be coated with a release agent, or a peelable Teflon(registered trademark) film may be used as the protective film. For long-time storage, the dry electrode covered with the peelable film is preferably sealed in a bag that is covered with aluminum etc. To prevent drying in the bag covered with aluminum, it is preferable to include water therein, too.

Before the inventive bio-electrode is attached to skin, the skin may be moisturized with water, alcohol, etc., or the skin may be wiped with a cloth or absorbent cotton containing water, alcohol, etc. The water and the alcohol may contain the above-described salts.

As has been described above, the inventive method for manufacturing a bio-electrode makes it possible to manufacture the inventive bio-electrode easily and at low cost, with the bio-electrode being excellent in electric conductivity and biocompatibility, light-weight, and capable of preventing significant reduction in the electric conductivity even when wetted with water or dried.

EXAMPLE

Hereinafter, the present invention will be specifically described with reference to Examples and Comparative Examples, but the present invention is not limited thereto. Incidentally, "Me" represents a methyl group, and "Vi" represents a vinyl group.

Synthesis Examples 1 to 5

N-carbonyl sulfonamide salt-trialkoxysilane compounds 1 to 5 in each of which a trialkoxysilane was bonded to an N-carbonyl sulfonamide salt were synthesized by mixing an N-carbonyl sulfonamide salt having a double bond, a trialkoxysilane compound having an SiH group, and a platinum catalyst in a mixed solvent containing toluene and PGMEA in 1:1, followed by heating at 60° C. for 2 hours.

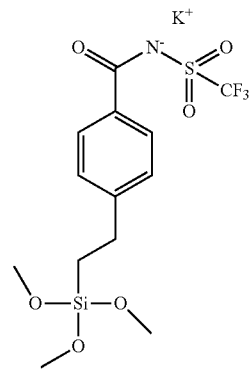

N-carbonyl sulfonamide salt-trialkoxysilane compound 1

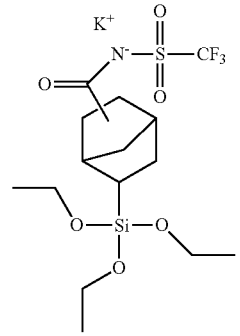

N-carbonyl sulfonamide salt-trialkoxysilane compound 2

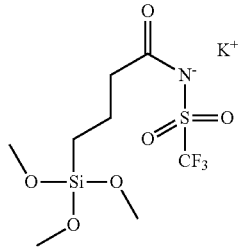

N-carbonyl sulfonamide salt-trialkoxysilane compound 3

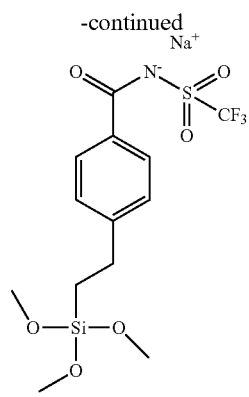

N-carbonyl sulfonamide salt-trialkoxysilane compound 4

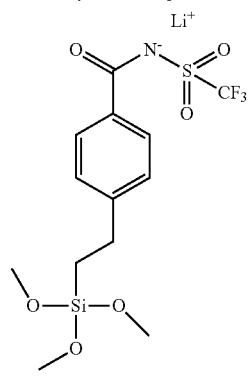

N-carbonyl sulfonamide salt-trialkoxysilane compound 5

Synthesis Example 6

Into 100 g of methyl isobutyl ketone (MIBK) dried with a molecular sieve, 5 g of dry silica (manufactured by SIGMA-Aldrich Co., LLC., size: 5 to 20 nm) was added and stirred for 1 day. Into the resultant, 15 g of a diethylene glycol dimethyl ether solution containing N-carbonyl sulfonamide salt-trialkoxysilane compound 1 at a concentration of 35 weight % was added dropwise and stirred at room temperature for 20 hours. Thus, N-carbonyl sulfonamide salt-silica 1 having N-carbonyl sulfonamide salt 1 in a pendant form was synthesized.

Synthesis Example 7

N-carbonyl sulfonamide salt-silica 2 having N-carbonyl sulfonamide salt 2 in a pendant form was synthesized as in Synthesis Example 6, except that N-carbonyl sulfonamide salt-trialkoxysilane compound 2 was used instead of N-carbonyl sulfonamide salt-trialkoxysilane compound 1.

Synthesis Example 8

N-carbonyl sulfonamide salt-silica 3 having N-carbonyl sulfonamide salt 3 in a pendant form was synthesized as in Synthesis Example 6, except that N-carbonyl sulfonamide salt-trialkoxysilane compound 3 was used instead of N-carbonyl sulfonamide salt-trialkoxysilane compound 1.

Synthesis Example 9

N-carbonyl sulfonamide salt-silica 4 having N-carbonyl sulfonamide salt 4 in a pendant form was synthesized as in Synthesis Example 6, except that N-carbonyl sulfonamide salt-trialkoxysilane compound 4 was used instead of N-carbonyl sulfonamide salt-trialkoxysilane compound 1.

Synthesis Example 10

N-carbonyl sulfonamide salt-silica 5 having N-carbonyl sulfonamide salt 5 in a pendant form was synthesized as in Synthesis Example 6, except that N-carbonyl sulfonamide salt-trialkoxysilane compound 5 was used instead of N-carbonyl sulfonamide salt-trialkoxysilane compound 1.

Synthesis Example 11

Into 100 g of methyl isobutyl ketone (MIBK) dried with a molecular sieve, 5 g of dry silica (manufactured by SIGMA-Aldrich Co., LLC., size: 5 to 20 nm) was added and stirred for 1 day. Into the resultant, 8 g of a diethylene glycol dimethyl ether solution containing N-carbonyl sulfonamide salt-trialkoxysilane compound 1 at a concentration of 35 weight % and 5 g of 35 weight % n-butyltrimethoxysilane were added dropwise and stirred at room temperature for 20 hours. Thus, N-carbonyl sulfonamide salt-silica 6 having N-carbonyl sulfonamide salt 1 in a pendant form was synthesized.

Synthesis Example 12

Into 100 g of methyl isobutyl ketone (MIBK) dried with a molecular sieve, 5 g of silicon powder (manufactured by Sigma-Aldrich Co., LLC., size: 100 nm or less) was added and stirred for 1 day. Into the resultant, 15 g of a diethylene glycol dimethyl ether solution containing N-carbonyl sulfonamide salt-trialkoxysilane compound 5 at a concentration of 35 weight % was added dropwise and stirred at room temperature for 20 hours. Thus, N-carbonyl sulfonamide salt-silicon powder 1 having N-carbonyl sulfonamide salt 5 in a pendant form was synthesized.

Synthesis Example 13

Into 100 g of methyl isobutyl ketone (MIBK) dried with a molecular sieve, 5 g of silicon monoxide powder (manufactured by Sigma-Aldrich Co., LLC., size: 440 nm or less) was added and stirred for 1 day. Into the resultant, 15 g of a diethylene glycol dimethyl ether solution containing N-carbonyl sulfonamide salt-trialkoxysilane compound 5 at a concentration of 35 weight % was added dropwise and stirred at room temperature for 20 hours. Thus, N-carbonyl sulfonamide salt-silicon monoxide powder 1 having N-carbonyl sulfonamide salt 5 in a pendant form was synthesized.

Synthesis Example 14

Into 100 g of methyl isobutyl ketone (MIBK) dried with a molecular sieve, 5 g of aluminum oxide powder (manufactured by Sigma-Aldrich Co., LLC., size: 50 nm or less) was added and stirred for 1 day. Into the resultant, 15 g of a diethylene glycol dimethyl ether solution containing N-carbonyl sulfonamide salt-trialkoxysilane compound 1 at a concentration of 35 weight % was added dropwise and stirred at room temperature for 20 hours. Thus, N-carbonyl sulfonamide salt-alumina powder 1 having N-carbonyl sulfonamide salt 1 in a pendant form was synthesized.

Synthesis Example 15

Into 100 g of methyl isobutyl ketone (MIBK) dried with a molecular sieve, 5 g of titanium oxide powder (manufactured by Sigma-Aldrich Co., LLC., size: 100 nm or less) was added and stirred for 1 day. Into the resultant, 15 g of a diethylene glycol dimethyl ether solution containing N-carbonyl sulfonamide salt-trialkoxysilane compound 1 at a concentration of 35 weight % was added dropwise and stirred at room temperature for 20 hours. Thus, N-carbonyl sulfonamide salt-titania powder 1 having N-carbonyl sulfonamide salt 1 in a pendant form was synthesized.

Synthesis Example 16

Into 100 g of methyl isobutyl ketone (MIBK) dried with a molecular sieve, 5 g of zirconium oxide powder (manufactured by Sigma-Aldrich Co., LLC., size: 100 nm or less) was added and stirred for 1 day. Into the resultant, 15 g of a diethylene glycol dimethyl ether solution containing N-carbonyl sulfonamide salt-trialkoxysilane compound 1 at a concentration of 35 weight % was added dropwise and stirred at room temperature for 20 hours. Thus, N-carbonyl sulfonamide salt-zirconia powder 1 having N-carbonyl sulfonamide salt 1 in a pendant form was synthesized.

Synthesis Example 17

Into 100 g of methyl isobutyl ketone (MIBK) dried with a molecular sieve, 5 g of lithium titanate powder (manufactured by Sigma-Aldrich Co., LLC., size: 200 nm or less) was added and stirred for 1 day. Into the resultant, 15 g of a diethylene glycol dimethyl ether solution containing N-carbonyl sulfonamide salt-trialkoxysilane compound 5 at a concentration of 35 weight % was added dropwise and stirred at room temperature for 20 hours. Thus, N-carbonyl sulfonamide salt-lithium titanate powder 1 having N-carbonyl sulfonamide salt 5 in a pendant form was synthesized.

Synthesis Examples 18 to 30

Ionic polymers 1 to 13, which were blended as ionic material (conductive material) (which may be also referred to as Ion Polymers) to bio-electrode composition solutions, were synthesized as follows. First, 30 mass % solutions of corresponding monomers in cyclopentanone were introduced into a reaction vessel and mixed. The reaction vessel was cooled to −70° C. under a nitrogen atmosphere, and subjected to vacuum degassing and nitrogen blowing, which were repeated three times. After raising the temperature to room temperature, azobisisobutyronitrile (AIBN) was added thereto as a polymerization initiator in an amount of 0.01 moles per 1 mole of the whole monomers. This was warmed to 60° C. and then allowed to react for 15 hours. After drying the solvent, the composition of the resulting polymer was identified by 1H-NMR. The molecular weight (Mw) and the dispersity (Mw/Mn) of the obtained polymer were determined by gel permeation chromatography (GPC) using tetrahydrofuran (THF) as a solvent. Thus synthesized Ionic polymers 1 to 13 are shown below.

Synthesis Example 18

Ionic polymer 1
Mw=38, 100
Mw/Mn=1.91

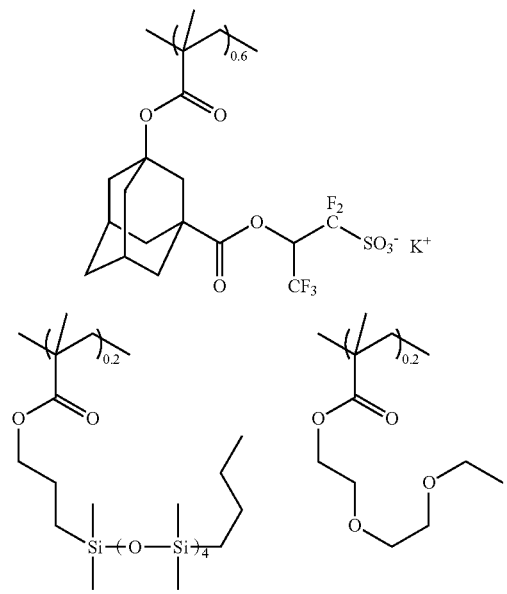

The repeating number in each formula shows the average value.

Synthesis Example 19

Ionic polymer 2
Mw=36, 100
Mw/Mn=1.93

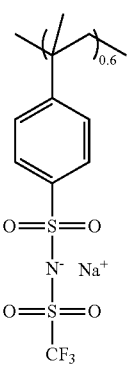

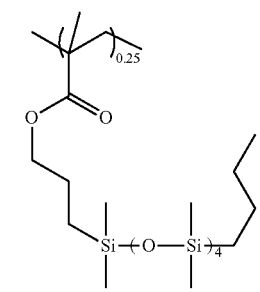

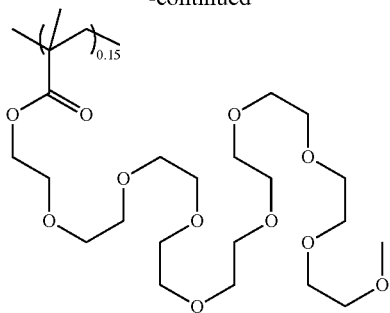

The repeating number in each formula shows the average value.

Synthesis Example 20

Ionic polymer 3
Mw=150,600
Mw/Mn=1.85

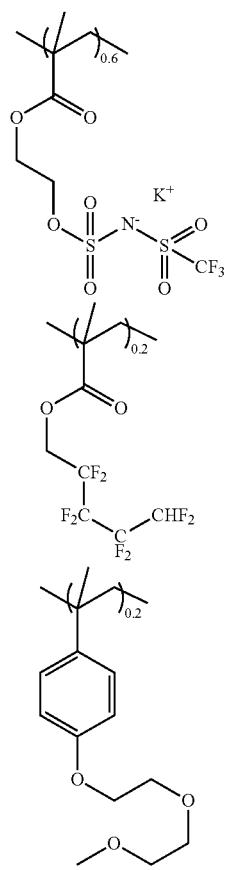

Synthesis Example 21

Ionic polymer 4
Mw=44,400
Mw/Mn=1.94

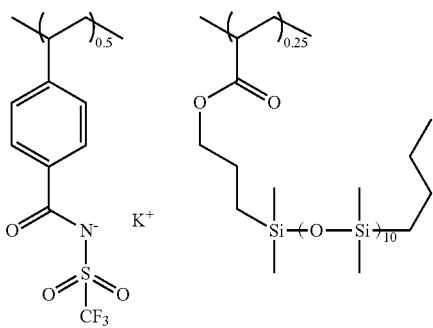

The repeating number in each formula shows the average value.

Synthesis Example 22

Ionic polymer 5
Mw=43,100
Mw/Mn=1.88

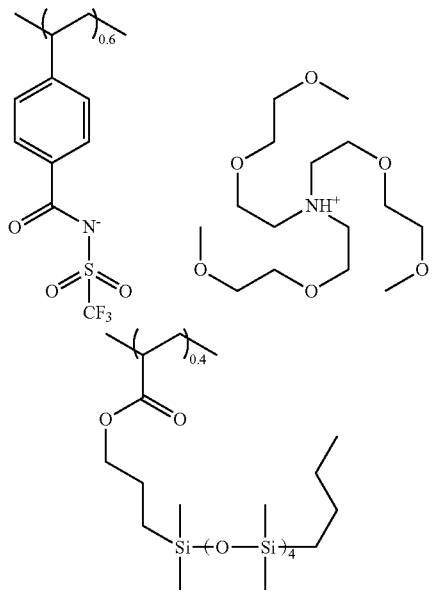

The repeating number in each formula shows the average value.

Synthesis Example 23

Ionic polymer 6
Mw=41,200
Mw/Mn=1.72

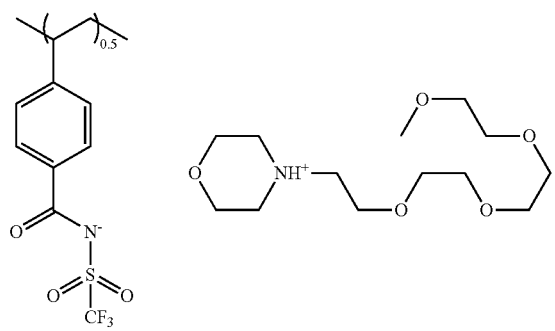
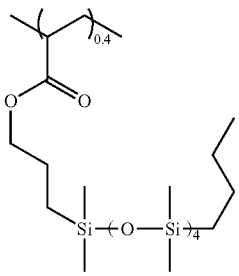
The repeating number in each formula shows the average value.
Synthesis Example 24
Ionic polymer 7
Mw=43, 600
Mw/Mn=1.93
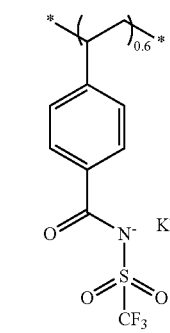
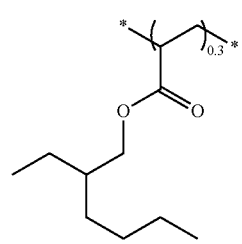
Synthesis Example 25
Ionic polymer 8
Mw=31, 600
Mw/Mn=2.10
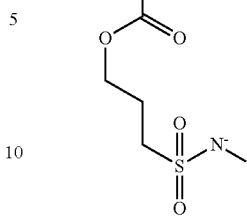
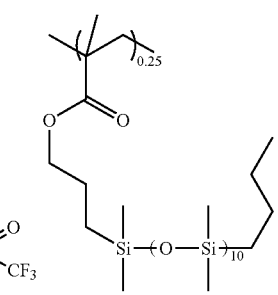
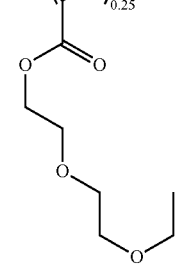
The repeating number in each formula shows the average value.
Synthesis Example 26
Ionic polymer 9
Mw=55, 100
Mw/Mn=22.02
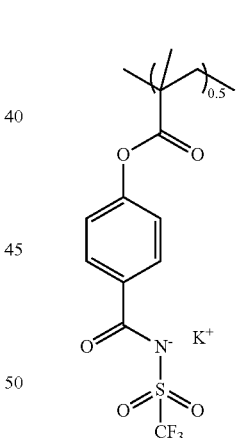
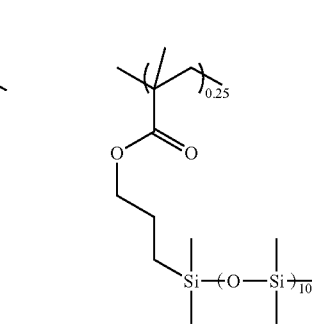
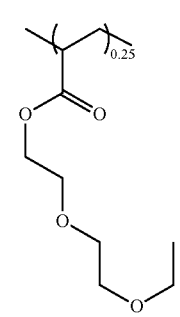
The repeating number in each formula shows the average value.

Synthesis Example 27

Ionic polymer 10
Mw=87,500
Mw/Mn=2.01

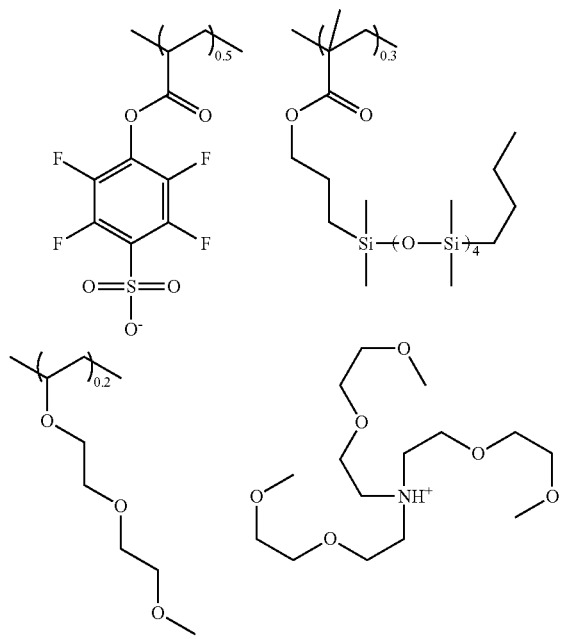

The repeating number in each formula shows the average value.

Synthesis Example 28

Ionic polymer 11
Mw=43,600
Mw/Mn=1.91

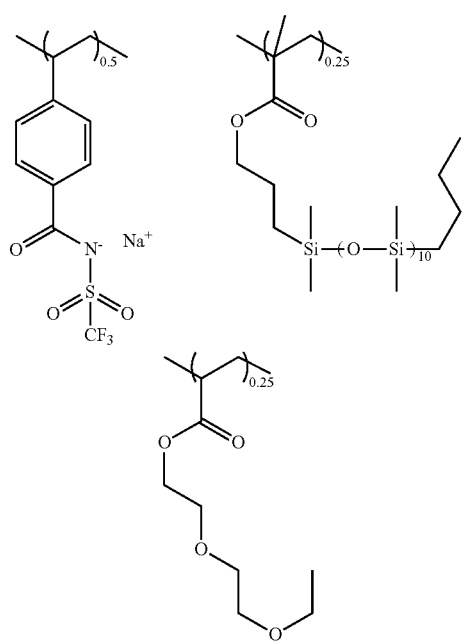

The repeating number in each formula shows the average value.

Synthesis Example 29

Ionic polymer 12
Mw=97,100
Mw/Mn=22.20

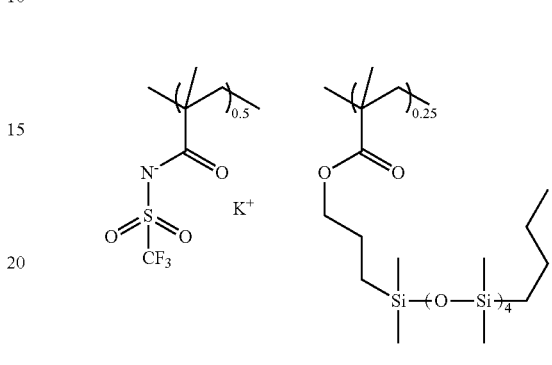

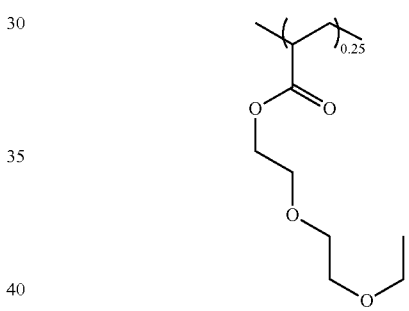

The repeating number in each formula shows the average value.

Synthesis Example 301

Ionic polymer 13
Mw=98,300
Mw/Mn=2.05

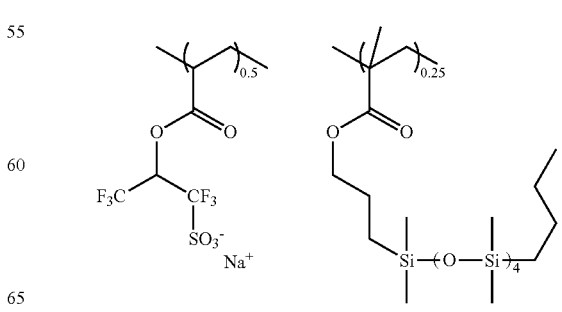

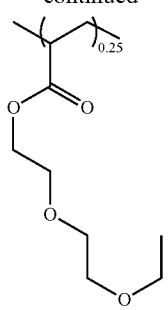
The repeating number in each formula shows the average value.
Polyglycerin-silicone compounds 1 to 8 are shown below.
Polyglycerin-silicone compound 1
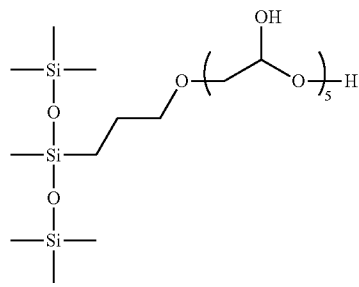
Polyglycerin-silicone compound 2
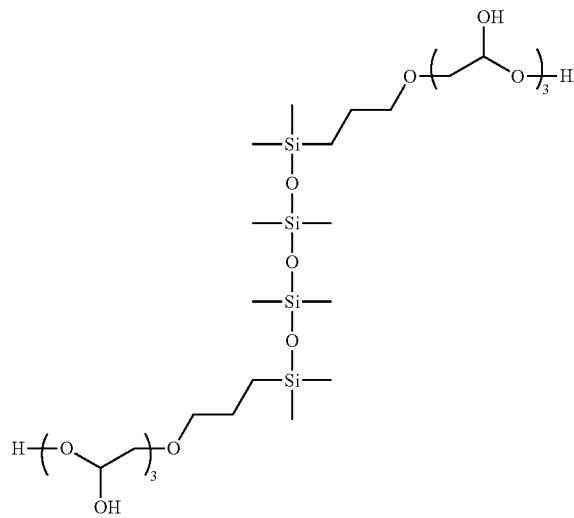
Polyglycerin-silicone compound 3
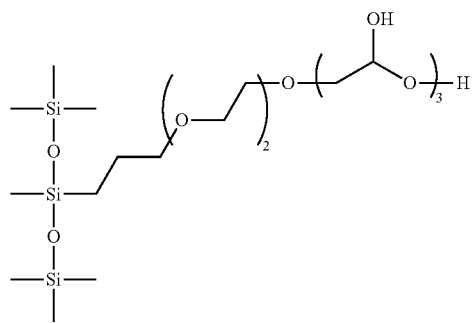
Polyglycerin-silicone compound 4
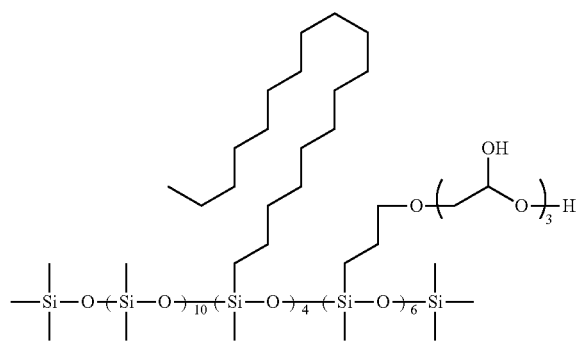
Polyglycerin-silicone compound 5
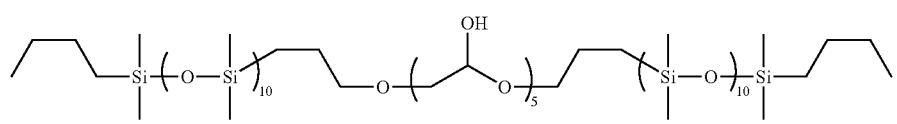

-continued

Polyglycerin-silicone compound 6

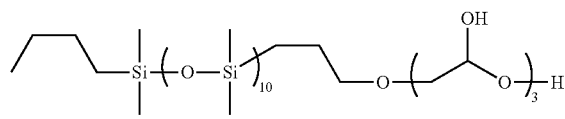

Polyglycerin-silicone compound 7

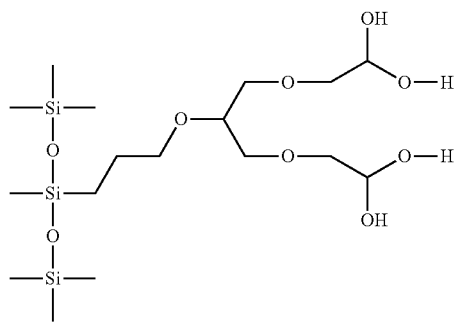

Polyglycerin-silicone compound 8

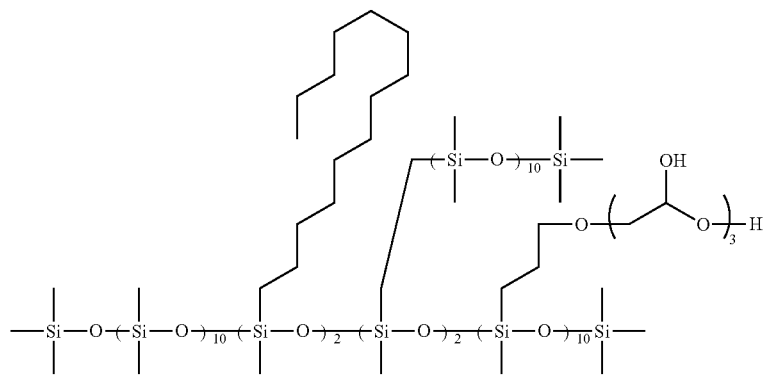

Siloxane compounds 1 to 4, which were blended as silicone-based resin to the bio-electrode composition solutions, are shown below.

(Siloxane Compound 1)

Siloxane compound 1 was vinyl group-containing polydimethylsiloxane having an alkenyl group-content of 0.007 mol/100 g in which the terminals of molecular chain were capped with $SiMe_2Vi$ groups, with the 30% solution in toluene having a viscosity of 27,000 mPa s.

(Siloxane Compound 2)

Siloxane compound 2 was a 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene.

(Siloxane Compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were capped with OH, with the 30% solution in toluene having a viscosity of 42,000 mPa-s; 100 parts by mass of 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene; and 26.7 parts by mass of toluene) with refluxing for 4 hours, followed by cooling.

(Siloxane Compound 4)

As methylhydrogensilicone oil, KF-99 manufactured by Shin-Etsu Chemical Co., Ltd. was used.

Acrylic polymer blended as acrylic-based resin to the bio-electrode composition solutions is shown below.

Acrylic polymer 1
Mw=108,000
Mw/Mn=2.32

Arcylic polymer 1

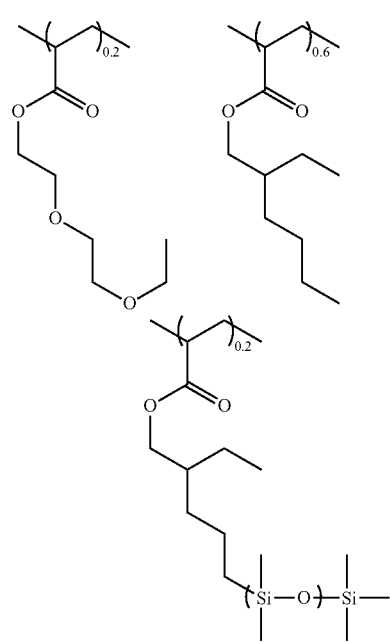

10 in average

The repeating number in each formula shows the average value.

Silicone urethane acrylates 1, 2, which were blended to the bio-electrode composition solutions as silicone-based, acrylic-based, or urethane-based resin, are shown below.

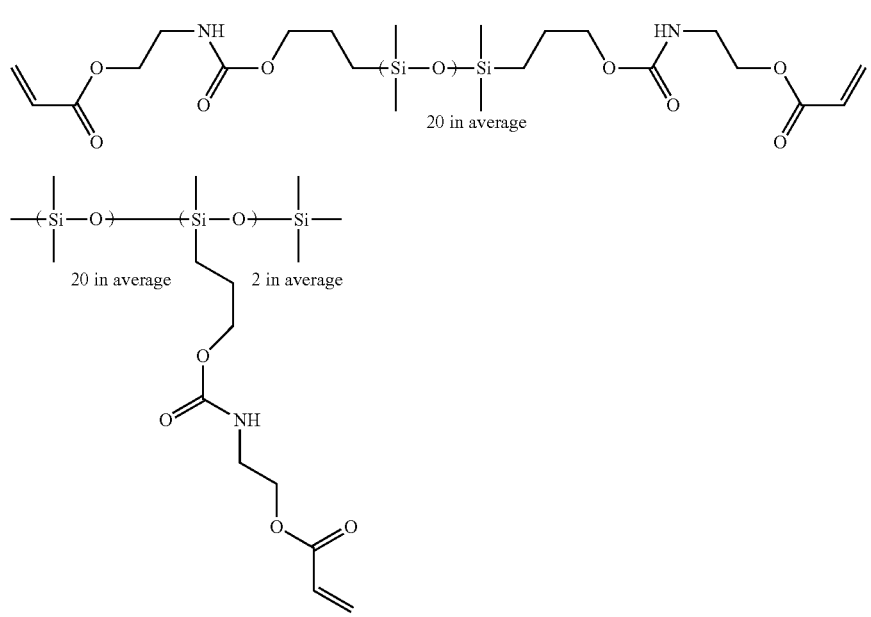

Silicone urethane acrylate 1

Silicone urethane acrylate 2

The repeating number in each formula shows the average value.

Organic solvents blended to the bio-electrode composition solutions are shown below.
EDE: diethylene glycol diethyl ether
ISOPAR G: isoparaffin base solvent manufactured by Standard Sekiyu CO., LTD.
ISOPAR M: isoparaffin base solvent manufactured by Standard Sekiyu CO., LTD.

Metal powders, radical generator, platinum catalyst, electric conductivity improver (carbon black, carbon nanotube, metal powder, lithium titanate), and silicone-based resin, which were blended as additives to the bio-electrode composition solutions, are shown below.

Metal Powders:
silver powder: silver flake with the diameter of 10 μm manufactured by Sigma-Aldrich Co., LLC.
gold powder: gold flake with the diameter of 10 μm or less manufactured by Sigma-Aldrich Co., LLC.
Photoradical generator: IRGACURE TPO manufactured by BASF SE
Platinum catalyst: CAT-PL-50T manufactured by Shin-Etsu Chemical Co., Ltd.
Carbon black: DENKA BLACK Li-400 manufactured by Denka Co., Ltd.
Multilayer carbon nanotube: with the diameter of 110 to 170 nm and length of 5 to 9 μm manufactured by Sigma-Aldrich Co., LLC.
Lithium titanate powder, spinel: with the size of 200 nm or less manufactured by Sigma-Aldrich Co., LLC.

As the silicone-based resin, KF-353 manufactured by Shin-Etsu Chemical Co., Ltd. was used, which is polyether type silicone oil with the side chain being modified with polyether.

Dry silica (manufactured by SIGMA-Aldrich Co., LLC., size: 5 to 20 nm) was used as silica in Comparative Example.

Examples 1 to 24, Comparative Examples 1 to 3

According to the compositions shown in Tables 1 and 2, the ionic materials (salts), resins, organic solvents, and additives (radical generator, platinum catalyst, electric conductivity improver) were blended to prepare bio-electrode composition solutions (Bio-electrode solutions 1 to 24, Comparative bio-electrode solutions 1 to 3).

TABLE 1

| Bio-electrode solution | Particle material (parts by mass) | Resin (parts by mass) | Ion polymer (parts by mass) | Organic solvent (parts by mass) | Additive (parts by mass) |
|---|---|---|---|---|---|
| Bio-electrode solution 1 | N-carbonyl sulfonamide salt-silica 1 (20) | Siloxane compound 1 (40) Siloxane compound 2 (100) Siloxane compound 4 (3) | — | ISOPAR G (60) cyclopentanone (70) | CAT-PL-50T (1.5) carbon black (14) |
| Bio-electrode solution 2 | N-carbonyl sulfonamide salt-silica 1 (20) | Siloxane compound 1 (40) Siloxane compound 2 (100) Siloxane compound 4 (3) | — | ISOPAR G (60) cyclopentanone (70) | CAT-PL-50T (1.5) carbon nanotube (3) silver flake (5) |
| Bio-electrode solution 3 | N-carbonyl sulfonamide salt-silica 1 (20) | Siloxane compound 1 (40) Siloxane compound 2 (100) Siloxane compound 4 (3) | — | ISOPAR G (60) cyclopentanone (70) | CAT-PL-50T (1.5) carbon black (15) gold flake (1) |
| Bio-electrode solution 4 | N-carbonyl sulfonamide salt-silica 5 (20) | Siloxane compound 1 (40) Siloxane compound 2 (100) Siloxane compound 4 (3) | — | ISOPAR G (60) cyclopentanone (70) | CAT-PL-50T (1.5) lithium titanate (12) |

TABLE 1-continued

| Bio-electrode solution | Particle material (parts by mass) | Resin (parts by mass) | Ion polymer (parts by mass) | Organic solvent (parts by mass) | Additive (parts by mass) |
|---|---|---|---|---|---|
| Bio-electrode solution 5 | N-carbonyl sulfonamide salt-silica 1 (10) | Siloxane compound 3 (126) Siloxane compound 4 (3) | Ion polymer 1 (20) | ISOPAR M (60) cyclopentanone (70) | CAT-PL-50T (1.5) |
| Bio-electrode solution 6 | N-carbonyl sulfonamide salt-silica 2 (12) | Siloxane compound 1 (40) Siloxane compound 2 (100) Siloxane compound 4 (3) | Ion polymer 2 (20) | ISOPAR G (60) cyclopentanone (70) | CAT-PL-50T (1.5) Polyglycerin silicone 1 (5.0) |
| Bio-electrode solution 7 | N-carbonyl sulfonamide salt-silica 3 (15) | Siloxane compound 1 (40) Siloxane compound 2 (100) Siloxane compound 4 (3) | Ion polymer 3 (20) | ISOPAR G (60) cyclopentanone (70) | CAT-PL-50T (1.5) Polyglycerin silicone 2 (5.0) |
| Bio-electrode solution 8 | N-carbonyl sulfonamide salt-silica 4 (14) | Siloxane compound 3 (126) Siloxane compound 4 (3) | Ion polymer 4 (20) | n-octane (60) cyclopentanone (70) | CAT-PL-50T (1.5) Polyglycerin silicone 3 (5.0) |
| Bio-electrode solution 9 | N-carbonyl sulfonamide salt-silica 5 (10) | Siloxane compound 3 (126) Siloxane compound 4 (3) | Ion polymer 7 (20) | n-nonane (60) 2-heptanone (14) | CAT-PL-50T (1.5) Polyglycerin silicone 4 (5.0) |
| Bio-electrode solution 10 | N-carbonyl sulfonamide salt-silica 6 (10) | Siloxane compound 3 (126) Siloxane compound 4 (3) | Ion polymer 7 (20) | n-nonane (60) 2-heptanone (14) | CAT-PL-50T (1.5) Polyglycerin silicone 4 (5.0) |
| Bio-electrode solution 11 | N-carbonyl sulfonamide salt-silica 1 (10) | Siloxane compound 3 (126) Siloxane compound 4 (3) | Ion polymer 8 (20) | ISOPAR G (60) cyclopentanone (60) | CAT-PL-50T (1.5) Polyglycerin silicone 5 (5.0) |
| Bio-electrode solution 12 | N-carbonyl sulfonamide salt-silica 1 (10) | Siloxane compound 3 (126) Siloxane compound 4 (3) | Ion polymer 9 (20) | n-decane (30) n-octane (30) 2-heptanone (14) | CAT-PL-50T (1.5) Polyglycerin silicone 6 (5.0) |
| Bio-electrode solution 13 | N-carbonyl sulfonamide salt-silica 1 (10) | Siloxane compound 3 (126) Siloxane compound 4 (3) | Ion polymer 10 (20) | ISOPAR G (60) cyclopentanone (70) | CAT-PL-50T (1.5) Polyglycerin silicone 7 (5.0) |
| Bio-electrode solution 14 | N-carbonyl sulfonamide salt-silica 1 (10) | Siloxane compound 3 (126) Siloxane compound 4 (3) | Ion polymer 11 (20) | n-decane (30) n-octane (30) 2-heptanone (14) | CAT-PL-50T (1.5) Polyglycerin silicone 6 (5.0) |
| Bio-electrode solution 15 | N-carbonyl sulfonamide salt-silica 1 (10) | Siloxane compound 3 (126) Siloxane compound 4 (3) | Ion polymer 12 (20) | ISOPAR G (60) cyclopentanone (70) | CAT-PL-50T (1.5) Polyglycerin silicone 7 (5.0) |

TABLE 2

| Bio-electrode solution | Particle material (parts by mass) | Resin (parts by mass) | Ion polymer (parts by mass) | Organic solvent (parts by mass) | Additive (parts by mass) |
|---|---|---|---|---|---|
| Bio-electrode solution 16 | N-carbonyl sulfonamide salt-silica 1 (10) | Silicone urethane acrylate 1 (80) | Ion polymer 5 (20) | EDE (60) cyclopentanone (70) | IRGACURE TPO (1) KF-353 (5) Polyglycerin silicone 8 (4.0) |
| Bio-electrode solution 17 | N-carbonyl sulfonamide salt-silica 1 (10) | Silicone urethane acrylate 2 (80) | Ion polymer 6 (20) | EDE (60) cyclopentanone (70) | IRGACURE TPO (1) Polyglycerin silicone 8 (4.0) |
| Bio-electrode solution 18 | N-carbonyl sulfonamide salt-silica 1 (10) | Acrylic polymer 1 (35) Silicone urethane acrylate 1 (45) | Ion polymer 13 (20) | EDE (60) cyclopentanone (70) | IRGACURE TPO (1) Polyglycerin silicone 8 (4.0) |
| Bio-electrode solution 19 | N-carbonyl sulfonamide salt-silicon powder 1 (20) | Siloxane compound 1 (40) Siloxane compound 2 (100) Siloxane compound 4 (3) | — | ISOPAR G (60) cyclopentanone (70) | CAT-PL-50T (0.7) lithium titanate powder (12) silver flake (8) |
| Bio-electrode solution 20 | N-carbonyl sulfonamide salt-silicon monoxide powder 1 (25) | Siloxane compound 3 (126) Siloxane compound 4 (3) | — | n-octane (40) n-decane (20) cyclopentanone (70) | CAT-PL-50T (1.5) carbon black (5) |
| Bio-electrode solution 21 | N-carbonyl sulfonamide salt-alumina powder 1 (30) | Siloxane compound 3 (126) Siloxane compound 4 (3) | — | n-nonane (60) 2-heptanone (14) | CAT-PL-50T (1.5) carbon black (5) |
| Bio-electrode solution 22 | N-carbonyl sulfonamide salt-titania powder 1 (25) | Siloxane compound 3 (126) Siloxane compound 4 (3) | — | ISOPAR G (60) cyclopentanone (60) | CAT-PL-50T (1.5) carbon black (6) |
| Bio-electrode solution 23 | N-carbonyl sulfonamide salt-zirconia powder 1 (10) | Siloxane compound 3 (126) Siloxane compound 4 (3) | — | n-decane (30) n-octane (30) 2-heptanone (14) | CAT-PL-50T (1.5) carbon black (6) |

TABLE 2-continued

| Bio-electrode solution | Particle material (parts by mass) | Resin (parts by mass) | Ion polymer (parts by mass) | Organic solvent (parts by mass) | Additive (parts by mass) |
|---|---|---|---|---|---|
| Bio-electrode solution 24 | N-carbonyl sulfonamide salt-lithium titanate powder 1 (10) | Siloxane compound 3 (126) Siloxane compound 4 (3) | Ion polymer 1 (10) | ISOPAR G (60) cyclopentanone (70) | CAT-PL-50T (1.5) carbon black (6) |
| Comparative bio-electrode solution 1 | — | Siloxane compound 1 (40) Siloxane compound 2 (100) Siloxane compound 4 (3) | — | ISOPAR G (60) cyclopentanone (70) | CAT-PL-50T (1.5) carbon black (14) |
| Comparative bio-electrode solution 2 | — | Siloxane compound 1 (40) Siloxane compound 2 (100) Siloxane compound 4 (3) | Ion polymer 1 (20) | ISOPAR G (60) cyclopentanone (70) | CAT-PL-50T (1.5) carbon black (14) |
| Comparative bio-electrode solution 3 | silica (20) | Siloxane compound 1 (40) Siloxane compound 2 (100) Siloxane compound 4 (3) | — | ISOPAR G (60) cyclopentanone (70) | CAT-PL-50T (1.5) carbon black (14) |

(Preparation of Bio-Electrodes)

As shown in FIG. 3, a thermoplastic urethane (TPU) film ST-604 (manufactured by Bemis Associates Inc.) designated by 20 was coated with an electro-conductive paste DOTITE FA-333 (manufactured by Fujikura Kasei Co., Ltd.) by screen printing. The coating film was baked in an oven at 120° C. for 10 minutes to print a keyhole-shaped electro-conductive pattern 2 including a circular portion with a diameter of 2 cm. Then, one of the bio-electrode solutions shown in Tables 1 and 2 was applied onto the circular portion by screen printing. After air-dried at room temperature for 10 minutes, the coating film was baked using an oven at 125° C. for 10 minutes to evaporate the solvent and form a living body contact layer 3 by curing. In this manner, bio-electrodes 1 were prepared (hereinafter, Bio-Electrodes 1 to 24, Comparative Bio-Electrodes 1 to 3 in accordance with Examples 1 to 24 and Comparative Examples 1 to 3). Bio-Electrodes 16 to 18 were further cured by irradiation with a xenon lamp at 200 mJ/cm² under a nitrogen atmosphere. Next, as shown in FIG. 4, the thermoplastic urethane film 20 having the bio-electrode 1 printed thereon was cut out and pasted on a double-sided tape 21. In this manner, three bio-electrode samples 10 were prepared for each of the composition solutions.

(Thickness Measurement of Living Body Contact Layer)

The thickness of the bio-electrode layer (living body contact layer) of each bio-electrode sample prepared as described above was measured with a micrometer. Table 3 shows the result.

(Biological Signal Measurement)

The electro-conductive wiring pattern formed from the electro-conductive paste of each bio-electrode sample was connected to a portable electrocardiograph HCG-901 (manufactured by OMRON HEALTHCARE Co., Ltd.) through an electro-conductive wire. A positive electrode of the electrocardiograph was attached to a location LA in FIG. 5 on a human body, a negative electrode was attached to a location LL, and an earth was attached to a location RA. Immediately after the attachments, the electrocardiogram measurement was started to measure the time until an electrocardiogram waveform (ECG signal) including P, Q, R, S, and T waves appeared as shown in FIG. 6. Table 3 shows the result.

TABLE 3

| Example | Living body contact, adhesive solution | Resin thickness (μm) | Time (min.) until ECG signal appeared |
|---|---|---|---|
| Example 1 | Bio-electrode solution 1 | 17 | 3 |
| Example 2 | Bio-electrode solution 2 | 18 | 2 |
| Example 3 | Bio-electrode solution 3 | 19 | 2 |
| Example 4 | Bio-electrode solution 4 | 21 | 2 |
| Example 5 | Bio-electrode solution 5 | 27 | 2 |
| Example 6 | Bio-electrode solution 6 | 32 | 1 |
| Example 7 | Bio-electrode solution 7 | 31 | 1 |
| Example 8 | Bio-electrode solution 8 | 33 | 0.8 |
| Example 9 | Bio-electrode solution 9 | 29 | 0.5 |
| Example 10 | Bio-electrode solution 10 | 31 | 0.8 |
| Example 11 | Bio-electrode solution 11 | 33 | 1 |
| Example 12 | Bio-electrode solution 12 | 39 | 1.5 |
| Example 13 | Bio-electrode solution 13 | 35 | 1 |
| Example 14 | Bio-electrode solution 14 | 35 | 1.2 |
| Example 15 | Bio-electrode solution 15 | 34 | 1.3 |
| Example 16 | Bio-electrode solution 16 | 25 | 1 |
| Example 17 | Bio-electrode solution 17 | 24 | 1 |
| Example 18 | Bio-electrode solution 18 | 26 | 1 |
| Example 19 | Bio-electrode solution 19 | 37 | 1.6 |
| Example 20 | Bio-electrode solution 20 | 31 | 1.2 |
| Example 21 | Bio-electrode solution 21 | 34 | 3.5 |
| Example 22 | Bio-electrode solution 22 | 35 | 3.6 |
| Example 23 | Bio-electrode solution 23 | 31 | 2.8 |
| Example 24 | Bio-electrode solution 24 | 39 | 2.5 |
| Comparative Example 1 | Comparative bio-electrode solution 1 | 25 | N/A |
| Comparative Example 2 | Comparative bio-electrode solution 2 | 26 | 40 |
| Comparative Example 3 | Comparative bio-electrode solution 3 | 22 | N/A |

As shown in Table 3, biological signals were detected immediately after the attachment to the skin in Examples 1 to 24, in which the living body contact layers were each formed using the inventive bio-electrode composition including particles having an N-carbonyl sulfonamide salt and a resin(s).

In contrast, no biological signals were detected in Comparative Example 1 not containing particles having an N-carbonyl sulfonamide salt and in Comparative Example 3 containing silica not modified with an N-carbonyl sulfonamide salt as in conventional techniques. In Comparative Example 2 containing an ion polymer, a biological signal was detected, but it took longer time for the signal to appear after the attachment to the skin.

From the foregoing, the bio-electrode including the living body contact layer formed from the inventive bio-electrode composition is excellent in electric conductivity, biocompatibility, and adhesion to the electro-conductive base material, and the ionic conductivity is so high that biological signals can be obtained immediately after the attachment to skin.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A bio-electrode composition comprising
   (A) particles having surfaces with an N-carbonyl sulfonamide salt, wherein the particles have diameters of 2 nm to 50 μm, and
   the N-carbonyl sulfonamide salt is shown by the following general formula (1),

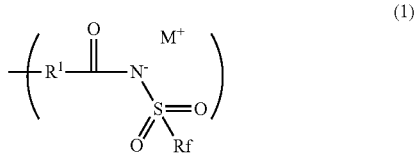

(1)

wherein $R^1$ represents a linear, branched, or cyclic alkylene group having 1 to 20 carbon atoms and optionally having an aromatic group, an ether group, or an ester group, or an arylene group having 6 to 10 carbon atoms; Rf represents a linear, branched, or cyclic alkyl group having 1 to 4 carbon atoms, or an aryl group having 6 to 10 carbon atoms, and optionally has a fluorine atom; and $M^+$ represents an ion selected from the group consisting of a lithium ion, a sodium ion, a potassium ion, and a silver ion.

2. The bio-electrode composition according to claim 1, wherein the particles are any of silicon material particles, alumina particles, titania particles, zirconia particles, lithium titanate particles, hafnium oxide particles, zinc oxide particles, germanium particles, germanium oxide particles, tin particles, tin oxide particles, antimony oxide particles, strontium oxide particles, tungsten oxide particles, bismuth oxide particles, yttrium oxide particles, ytterbium oxide particles, gadolium oxide particles, indium oxide particles, molybdenum oxide particles, and scandium oxide particles.

3. The bio-electrode composition according to claim 1, wherein
   the component (A) comprises a reaction product between an alkoxysilane compound shown by the following general formula (2) and silicon material particles selected from the group consisting of silica particles, Si particles, SiO particles, SiC particles, and composites thereof,

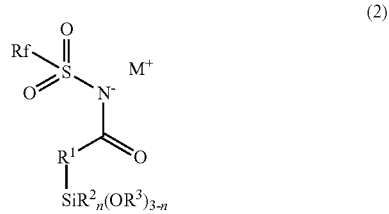

(2)

wherein $R^1$, Rf, and $M^+$ are as defined above; $R^2$ and $R^3$ are identical to or different from each other and each represent a hydrogen atom, or a linear, branched, or cyclic alkyl group having 1 to 10 carbon atoms; and "n" represents 0 or 1.

4. The bio-electrode composition according to claim 3, wherein the component (A) is a reaction product between 100 parts by mass of the silicon material particles and 5 parts by mass or more of the alkoxysilane compound shown by the general formula (2).

5. The bio-electrode composition according to claim 1, further comprising a component (B) which is an adhesive resin.

6. The bio-electrode composition according to claim 5, wherein the component (B) is one or more selected from the group consisting of a silicone resin, a (meth)acrylate resin, and a urethane resin.

7. The bio-electrode composition according to claim 5, wherein the component (B) comprises diorganosiloxane having an alkenyl group, and organohydrogenpolysiloxane having an SiH group.

8. The bio-electrode composition according to claim 7, wherein
   the component (B) further comprises a silicone resin having an $SiO_2$ unit and an $R_xSiO_{(4-x)/2}$ unit, wherein R represents a substituted or unsubstituted monovalent hydrocarbon group having 1 to 10 carbon atoms, and "X" represents a number in a range of 2.5 to 3.5.

9. The bio-electrode composition according to claim 1, further comprising a component (C) which is a polymer compound having an ionic repeating unit.

10. The bio-electrode composition according to claim 9, wherein the ionic repeating unit comprises a repeating unit-c having a structure selected from the group consisting of salts of ammonium, sodium, potassium, and silver formed with any of fluorosulfonic acid, fluorosulfonimide, and N-carbonyl-fluorosulfonamide.

11. The bio-electrode composition according to claim 9, wherein the ionic repeating unit has a structure shown by any of the following general formulae (3)-1 to (3)-4,

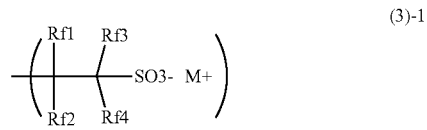

(3)-1

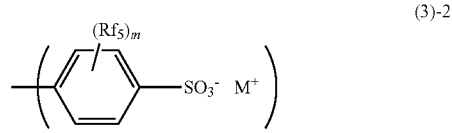

(3)-2

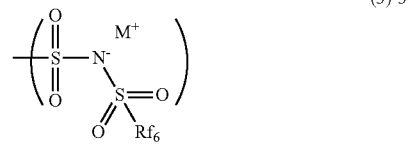

(3)-3

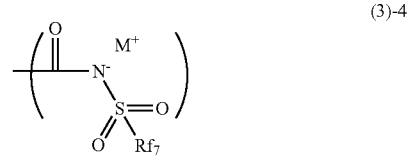

(3)-4 wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, and have at least one fluorine atom; $M^+$ represents an ion selected from the group consisting of an ammonium ion, a sodium ion, a potassium ion, and a silver ion; and "m" represents an integer of 1 to 4.

12. The bio-electrode composition according to claim 9, wherein the ionic repeating unit comprises at least one repeating unit selected from the group consisting of repeating units shown by the following general formula (3),

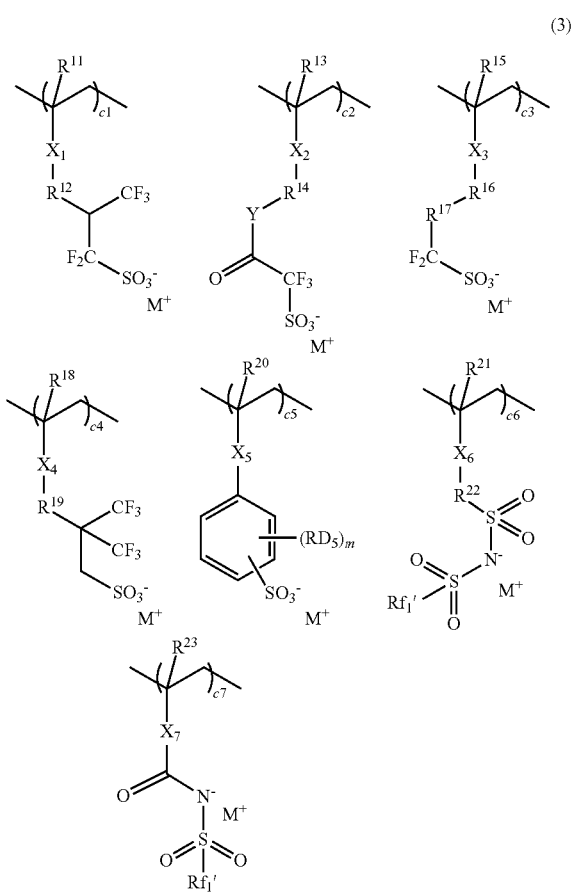

wherein $R^{11}$, $R^{13}$, $R^{15}$, $R^{18}$, $R^{20}$, $R^{21}$, and $R^{23}$ each independently represent a hydrogen atom or a methyl group; $R^{12}$, $R^{14}$, $R^{16}$, $R^{19}$, and $R^{22}$ each independently represent a single bond, or a linear, branched, or cyclic hydrocarbon group having 1 to 12 carbon atoms, the hydrocarbon group optionally having either or both of an ester group and an ether group; $R^{17}$ represents a linear or branched alkylene group having 1 to 4 carbon atoms, and one or two hydrogen atoms in $R^1$ are optionally substituted with a fluorine atom; $X_1$, $X_2$, $X_3$, $X_4$, $X_6$, and $X_7$ each independently represent any of a single bond, a phenylene group, a naphthylene group, an ether group, an ester group, and an amide group; $X_5$ represents any of a single bond, an ether group, and an ester group; Y represents an oxygen atom or a $-NR^{29}-$ group; $R^{29}$ represents a hydrogen atom, or a linear or branched alkyl group having 1 to 4 carbon atoms; $Rf_1'$ represents a fluorine atom or a trifluoromethyl group; $Rf_5$ represents a fluorine atom, or a linear or branched alkyl group having 1 to 4 carbon atoms and at least one fluorine atom; "m" represents an integer of 1 to 4; c1, c2, c3, c4, c5, c6, and c7 satisfy $0 \leq c1 \leq 1.0$, $0 \leq c2 \leq 1.0$, $0 \leq c3 \leq 1.0$, $0 \leq c4 \leq 1.0$, $0 \leq c5 \leq 1.0$, $0 \leq c6 \leq 1.0$, $0 \leq c7 \leq 1.0$, and $0 < c1+c2+c3+c4+c5+c6+c7 \leq 1.0$; and $M^+$ represents an ion selected from the group consisting of an ammonium ion, a sodium ion, a potassium ion, and a silver ion.

13. The bio-electrode composition according to claim 1, further comprising a component (D) which is a carbon powder and/or a metal powder.

14. The bio-electrode composition according to claim 13, wherein the carbon powder is one or both of carbon black and carbon nanotube.

15. The bio-electrode composition according to claim 13, wherein the metal powder is a powder of a metal selected from the group consisting of gold, silver, platinum, copper, tin, titanium, nickel, aluminum, tungsten, molybdenum, ruthenium, chromium, and indium.

16. The bio-electrode composition according to claim 15, wherein the metal powder is a silver powder.

17. The bio-electrode composition according to claim 1, further comprising a component (E) which is an organic solvent.

18. A bio-electrode comprising an electro-conductive base material and a living body contact layer formed on the electro-conductive base material, wherein
the living body contact layer is a cured product of the bio-electrode composition according to claim 1.

19. The bio-electrode according to claim 18, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

20. A method for manufacturing a bio-electrode having an electro-conductive base material and a living body contact layer formed on the electro-conductive base material, comprising:
applying the bio-electrode composition according to claim 1 onto the electro-conductive base material; and
curing the bio-electrode composition to form the living body contact layer.

21. The method for manufacturing a bio-electrode according to claim 20, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

22. A silicon material particle comprising an N-carbonyl sulfonamide salt shown by the following general formula (1) on a surface of the silicon material particle, the particle having diameters of 2 nm to 50 µm,

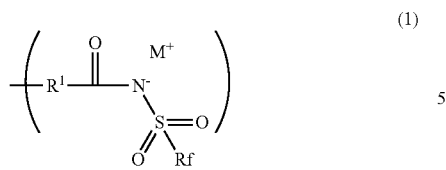
(1)

wherein $R^1$ represents a linear, branched, or cyclic alkylene group having 1 to 20 carbon atoms and optionally having an aromatic group, an ether group, or an ester group, or an arylene group having 6 to 10 carbon atoms; Rf represents a linear, branched, or cyclic alkyl group having 1 to 4 carbon atoms, or an aryl group having 6 to 10 carbon atoms, and optionally has a fluorine atom; and $M^+$ represents an ion selected from the group consisting of a lithium ion, a sodium ion, a potassium ion, and a silver ion.

23. The silicon material particle according to claim 22, wherein the silicon material particle is selected from the group consisting of silica particles, Si particles, SiO particles, SiC particles, and composites thereof.

* * * * *